(12) United States Patent
Chang et al.

(10) Patent No.: US 12,240,890 B2
(45) Date of Patent: Mar. 4, 2025

(54) COMPOSITIONS AND METHODS FOR TREATING AND/OR PREVENTING PATHOGENIC FUNGAL INFECTION AND FOR MAINTENANCE OF MICROBIOME COMMENSALISM

(71) Applicant: The University of Chicago, Chicago, IL (US)

(72) Inventors: Eugene B. Chang, Chicago, IL (US); Joseph F. Pierre, Chicago, IL (US); Katharine A. Harris, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/611,128

(22) PCT Filed: May 16, 2018

(86) PCT No.: PCT/US2018/032997
§ 371 (c)(1),
(2) Date: Nov. 5, 2019

(87) PCT Pub. No.: WO2018/213468
PCT Pub. Date: Nov. 22, 2018

(65) Prior Publication Data
US 2020/0062823 A1 Feb. 27, 2020

Related U.S. Application Data

(60) Provisional application No. 62/581,358, filed on Nov. 3, 2017, provisional application No. 62/506,902, filed on May 16, 2017.

(51) Int. Cl.
| | | |
|---|---|---|
| C07K 14/72 | (2006.01) | |
| A61K 38/17 | (2006.01) | |
| A61K 45/06 | (2006.01) | |
| A61P 31/10 | (2006.01) | |

(52) U.S. Cl.
CPC .......... *C07K 14/72* (2013.01); *A61K 38/1796* (2013.01); *A61K 45/06* (2013.01); *A61P 31/10* (2018.01)

(58) Field of Classification Search
None
See application file for complete search history.

(56) References Cited

U.S. PATENT DOCUMENTS

| | | | |
|---|---|---|---|
| 5,359,030 A | 10/1994 | Ekwuribe | |
| 5,681,811 A | 10/1997 | Ekwuribe | |
| 6,552,167 B1 | 4/2003 | Rose | |
| 7,157,426 B2 * | 1/2007 | Quay | ..................... A61K 45/06 |
| | | | 514/21.3 |
| 2006/0211610 A1 * | 9/2006 | Dong | .................. A61P 3/00 |
| | | | 514/4.9 |

FOREIGN PATENT DOCUMENTS

| | | | | |
|---|---|---|---|---|
| EP | 2329839 | * | 9/2015 | |
| WO | WO-03026591 A2 | * | 4/2003 | ............. A61K 38/17 |
| WO | WO 2003/057235 | | 7/2003 | |
| WO | WO 2005/080433 | | 9/2005 | |
| WO | WO 2006/066024 | * | 6/2006 | |

OTHER PUBLICATIONS

Tan et al. (Drugs Aging 2004; 21 (2): 101-112) (Year: 2004).*
Grundemar et al. (Br. J. Pharmacol. (1990), 100, 190-192) (Year: 1990).*
Kitamura et al. (Biochem Biophys Res Commun. Jun. 29, 1990;169(3):1164-71) (Year: 1990).*
Allmendinger et al., Fluoroolefin Dipeptide Isoteres-I: The synthesis of Glyψ (CF=CH) Gly and racemic Pheψy (CF=CH) Gly. Tetrahydron Lett. 1990;31: 7297-7300.
Batterham et al., PYY modulation of cortical and hypothalamic brain areas predicts feeding behaviour in humans. Nature. 2007;450(7166):106-9.
Chorev et la., A Dozen Years of Retro-Inverso Peptidomimetics. Acc. Chem. Res. 1993;26:266-73.
Clevers et al., Paneth cells: maestros of the small intestinal crypts. Annu Rev Physiol. 2013;75:289-311.
Conlon, The origin and evolution of peptide YY (PYY) and pancreatic polypeptide (PP). Peptides. 2002;23(2):269-78.
Delgado et al., The uses and properties of PEG-linked proteins. Crit Rev Ther Drug Carrier Syst. 1992;9(3-4):249-304.
Francis et al., PEGylation of cytokines and other therapeutic proteins and peptides: the importance of biological optimisation of coupling techniques. Int J Hematol. Jul. 1998;68(1):1-18.
Glavas et al., Characterization of brainstem peptide YY (PYY) neurons. J Comp Neurol. 2008;506(2):194-210.
Gombotz et al., Biodegradable polymers for protein and peptide drug delivery. Bioconjug Chem. Jul.-Aug. 1995;6(4):332-51.
Gunawardene et al., Classification and functions of enteroendocrine cells of the lower gastrointestinal tract. Int J Exp Pathol. 2011;92(4):219-31.
Hill et al., Characterization of the diurnal rhythm of peptide YY and its association with energy balance parameters in normal-weight premenopausal women. Am J Physiol Endocrinol Metab. 2011;301(2):E409-15.
Hoffman et al., The Stereoselective Synthesis of 2-Alkyl .gamma.-Keto Acid and Heterocyclic Ketomethylene Peptide Isostere Core Units Using Chiral Alkylation by 2-Triflyloxy Esters. J. Org. Chem. 1995;60(16):5107-13.
Holzer et al., Neuropeptide Y, peptide YY and pancreatic polypeptide in the gut-brain axis. Neuropeptides. 2012;46(6):261-74.
Lambert et al., Langerhans cell expression of neuropeptide Y and peptide YY. Neuropeptides. 2002;36(4):246-51.

(Continued)

*Primary Examiner* — Sergio Coffa
(74) *Attorney, Agent, or Firm* — David W. Staple; Casimir Jones, S.C.

(57) ABSTRACT

Provided herein are compositions and methods for treating and/or preventing pathogenic fungal infection and for maintenance of microbiome commensalism. In particular, provided herein are compositions comprising modified peptide YY (PYY) peptides and therapeutic and/or prophylactic methods of use thereof.

11 Claims, 23 Drawing Sheets

Specification includes a Sequence Listing.

(56) References Cited

OTHER PUBLICATIONS

Lavielle et al., Importance of the leucine side-chain to the spasmogenic activity and binding of substance P analogues. Int J Pept Protein Res. Sep. 1993;42(3):270-7.

Luisi et al., ψ(SO2—NH) transition state isosteres of peptides. Synthesis of the glutathione disulfide analogue. Tetrahedron Letters. Apr. 2, 1993;34(14):2391-2.

Ostresh et al., "Libraries from libraries": chemical transformation of combinatorial libraries to extend the range and repertoire of chemical diversity. Proc Natl Acad Sci U S A. Nov. 8, 1994;91(23):11138-42.

Pierre et al., Model for Paneth cell (PC) PYY action and regulation of fungal commensalisms and potential frole in the pathogenesis of ileal Crhon's Disease (iCD). bioRxiv preprint Aug. 11, 2020. 33 pages. Retrived from https://doi.org/10.1101/2020.05.15.096875.

Saski et al., Protection of ψ(CH2NH) Peptide Bond with 2,4-Dimethoxybenzyl Group in Solid-Phase Peptide Synthesis. Chem. Pharm. Bull. Jan. 1997;45(1):13-7.

Schmidt et al., Structure-activity relationships of dermorphin analogues containing N-substituted amino acids in the 2-position of the peptide sequence. Intl. J. Peptide and Protein Res. Jul. 1995;46(1):47-55.

Sherman et al., Compatibility of thioamides with reverse turn features: synthesis and conformational analysis of two model cyclic pseudopeptides containing thioamides as backbone modifications. J. Am. Chem. Soc. 1990;112(1):433-441.

Spatola, Synthesis of Pseudopeptides, Methods Neurosci, 1993, 13:19-42.

Tatemoto, Isolation and characterization of peptide YY (PYY), a candidate gut hormone that inhibits pancreatic exocrine secretion. Proc Natl Acad Sci U S A. 1982;79(8):2514-8.

Uniprot Accession No. G3TTU6. PYY *Loxodonta africana* (African elephant). May 10, 2017. 2 pages.

Vouldoukis et al., Broad spectrum antibiotic activity of the skin-PYY. FEBS Lett. 1996;380(3):237-40.

Zalipsky, Functionalized poly(ethylene glycol) for preparation of biologically relevant conjugates. Bioconjug Chem. Mar.-Apr. 1995;6(2):150-65.

International Search Report for PCT/US2018/032997, mailed Oct. 15, 2018, 15 pages.

Partial Search Report of EP18801716.4, mailed Nov. 23, 2020, 17 pages.

\* cited by examiner a.

b.

| | |
|---|---|
| PYY 1-36 | :YPIKPEAPGEDASPEELNRYYASLRHYLNLVTRQRY |
| PYY 1-36 Modified | :YPIKPEAPGEDASPEELNAYYASLAHYLNLVTAQAY |
| PYY 1-13 | :YPIKPEAPGEDAS |
| PYY 14-36 | :              PEELNRYYASLRHYLNLVTRQRY |
| PYY 14-36 Modified | :              PEELNAYYASLAHYLNLVTAQAY | c.

FIG. 15

```
NPY Query   1   YPSKPDNPGEDA PAEDMARYYSALRHYINLITRQRY   36
PYY Sbjct   1   YP KP+ PGED   E++ RYI++LRHY+NL+TRQRY       36
                YPIKPEAPGEDASPEELNRYYASLRHYLNLVTRQRY SkinPYY Query 1 YPPKPESPGEDA SPEDMNRYL QALRHYINLVTRQRY  36
PYY Sbjct   1   YP KP++PGED  SPEE+N+Y  +LRHY+NLVTRQRY      36
                YPIKPEAPGEDASPEELNRYYASLRHYLNLVTRQRY
```

COMPOSITIONS AND METHODS FOR TREATING AND/OR PREVENTING PATHOGENIC FUNGAL INFECTION AND FOR MAINTENANCE OF MICROBIOME COMMENSALISM

CROSS-REFERENCE TO RELATED APPLICATION

The present application is a § 371 National Entry Application of PCT/US2018/32997, filed May 16, 2018, which claims priority to U.S. Provisional Patent Application Ser. No. 62/506,902 filed May 16, 2017, and U.S. Provisional Patent Application Ser. No. 62/581,358 filed Nov. 3, 2017, each of which are hereby incorporated by reference in their entireties.

STATEMENT REGARDING FEDERAL FUNDING

This invention was made with government support under DK042086, DK113788, and DK105728 awarded by The National Institutes of Health. The government has certain rights in the invention.

SEQUENCE LISTING

The text of the computer readable sequence listing filed herewith, titled "35185-253_SEQUENCE_LISTING_ST25", created Nov. 12, 2021, having a file size of 21,623 bytes, is hereby incorporated by reference in its entirety.

FIELD

Provided herein are compositions and methods for treating and/or preventing pathogenic fungal infection and for maintenance of microbiome commensalism. In particular, provided herein are compositions comprising modified peptide YY (PYY) peptides and therapeutic and/or prophylactic methods of use thereof.

BACKGROUND

The healthy human intestinal microflora contains commensal eukaryotic fungal species. However, these same commensal fungi have the capacity to cause serious disease in their hosts. For example, *Candida albicans* colonizes up to 70% of human adults, and this colonization does not usually have any adverse consequences. However, these same *C. albicans* species can transition from growth in the harmless yeast form to a virulent, hyphal form that is invasive and overgrows to produce high fungal burdens that result in disease. Candidiasis is a serious problem in immunocompromised patients and diabetics, and can occur at mucosal sites where *Candida* colonization normally occurs or invasive sites when *Candida* species escape their normal niches and replicate in other organ systems. Candidemia, or *Candida* infections of the bloodstream, are especially serious, with mortality rates of 30-40%.

PYY is a highly conserved 36-residue peptide produced in vertebrate species from cartilaginous fish to humans (Ref. 1; incorporated by reference in its entirety). Since its discovery in porcine intestine and brain in 1982, diverse regulatory roles have been identified for PYY, including control of energy homeostasis and food intake, sympathetic vascular tone, digestion, circadian rhythms, and endocrine as well as autonomic functions (Refs 2-6; incorporated by reference in their entireties). The classically understood regulatory functions of PYY are mediated by receptor binding of the $PYY_{1-36}$ and a cleaved form, $PYY_{3-36}$, to various receptors in respective organ tissues. PYY is predominantly produced by a subset of enteroendocrine cells, L-cells, which are most abundant in the distal ileum and colon and release PYY basolaterally into systemic circulation in response to feeding (Ref. 7; incorporated by reference in its entirety). PYY expression is also described in the brain stem, pancreatic islets, and epidermal dendritic cells (Ref. 5,8; incorporated by reference in their entireties).

SUMMARY

Provided herein are compositions and methods for treating and/or preventing pathogenic fungal infection and for maintenance of microbiome commensalism. In particular, provided herein are compositions comprising modified peptide YY (PYY) peptides and therapeutic and/or prophylactic methods of use thereof.

In some embodiments, provided herein are compositions comprising a peptide having 5 or fewer (e.g., 5, 4, 3, 2, 1, 0) substitutions relative to one or more of SEQ ID NOs: 3, and 39-46, and less than 100% (e.g., <95%, <90%) sequence identity with SEQ ID NOs: 1, 2, and/or 6. In some embodiments, peptide comprise 100% sequence identity with SEQ ID NO: one or more of SEQ ID NOs: 3, and 39-46. In some embodiments, a peptide is provided in which an amino acid at a position corresponding to position 2 of SEQ ID NO: 3 is E or D, position 13 of SEQ ID NO: 3 is R or K, position 17 of SEQ ID NO: 3 is A, position 22 of SEQ ID NO: 3 is L, and/or position 23 of SEQ ID NO: 3 is A or R. In some embodiments, a peptide comprises 70% or greater (e.g., >75%, >80%, >85%, >90%, >95%) sequence identity with one or more of SEQ ID NOs: 4, 5, 15-17, 26, 29, 31, and/or 34-38. In some embodiments, peptides comprise 100% sequence identity with one of SEQ ID NOs: 4, 5, 15-17, 26, 29, 31, and/or 34-38. In some embodiments, (i) one or more of the amino acid residues in the peptide are D-enantiomers, (ii) the peptide comprises an N-terminally acetyl group, (iii) the peptide comprises a deamidated C-terminal group, (iv) the peptide comprises one or more unnatural amino acids, (v) the peptide comprises one or more amino acid analogs, and/or (vi) the peptide comprises one or more peptoid amino acids. In some embodiments, the peptide or an amino acid therein comprises a modification selected from the group consisting of phosphorylation, glycosylation, ubiquitination, S-nitrosylation, methylation, N-acetylation, lipidation, lipoylation, deimination, eliminylation, disulfide bridging, isoaspartate formation, racemization, glycation; carbamylation, carbonylation, isopeptide bond formation, sulfation, succinylation, S-sulfonylation, S-sulfinylation, S-sulfenylation, S-glutathionylation, pyroglutamate formation, propionylation, adenylylation, nucleotide addition, iodination, hydroxylation, malonylation, butyrylation, amidation, deamidation, alkylation, acylation, biotinylation, carbamylation, oxidation, and pegylation. In some embodiments, the peptide exhibits enhanced stability relative to one of SEQ ID NOs: 1, 2, and 6. In some embodiments, the peptide exhibits enhanced anti-fungal-virulence activity relative to one of SEQ ID NOs: 1, 2, and 6.

In some embodiments, provided herein are pharmaceutical compositions comprising: (i) a PYY peptide described in the preceding paragraph or elsewhere described herein and (ii) one a pharmaceutically-acceptable carrier. In some embodiments, a pharmaceutical composition further comprises one or more additional therapeutic agents. In some embodiments, the one or more additional therapeutic agents are selected from the group consisting of an antibiotic agent, an antiparasitic agent, and antiviral agent, an antimycotic agent, and commensal microbes. In some embodiments, the pharmaceutical composition is formulated for oral, intravenous, or rectal administration.

In some embodiments, provided herein are methods for maintaining or inducing healthy commensal microflora of a subject comprising administering a pharmaceutical composition described herein to the subject. In some embodiments, healthy commensal microflora is induced or maintained on the skin, in the gut, in the oral cavity, or in the vaginal cavity. In some embodiments, provided herein are methods of treating or preventing a pathogenic infection in a subject comprising administering a pharmaceutical composition described herein to the subject. Provided herein are methods of treating or preventing an inflammatory disease or condition of the gastrointestinal tract in a subject comprising administering a pharmaceutical composition of described herein to the subject. In some embodiments, the disease or condition is ulcerative colitis or Crohn's disease.

In some embodiments, provided herein are devices comprising one or more surfaces coated with a composition comprising a PYY peptide described herein.

In some embodiments, provided herein is the use of a composition described herein for the treatment or preventing a pathogenic infection in a subject. In some embodiments, provided herein is the use of a composition described herein the manufacture of a medicament for the treatment or prevention a pathogenic infection in a subject. In some embodiments, provided herein is the use of a composition described herein for preventing biofilm formation (e.g., on a surface or device).

In some embodiments, provided herein are compositions comprising a peptide corresponding to a portion of PYY (SEQ ID NO: 1), such as positions 10-36 (e.g., any suitable peptides beginning at position 10, 11, 12, 13, 14, 15, or 16 and ending at position 33, 34, 35, or (e.g., 14-36, 13-36, etc.)), and having 8 or fewer (e.g., 1, 2, 3, 4, 5, or ranges therebetween) substitutions relative to said portion of PYY. Examples of peptides within the scope herein include peptides comprising or consisting of the sequences of SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46. In some embodiments, provided herein are peptides having enhanced characteristics (e.g., antifungal activity, inhibition of biofilm formation, expression, stability, biostability, biocompatibility, etc.) relative to a PYY sequence (e.g., SEQ ID NO: 1, SEQ ID NO: 2, SEQ ID NO: 6, etc.). In some embodiments, a peptide comprises substitutions relative to SEQ ID NO: 6 at one or more positions selected from positions 13, 15, 26, 29, 30, 35, and 36 (position numbers are based on SEQ ID NO:1). In some embodiments, a peptide comprises substitutions relative to SEQ ID NO: 6 at one or more positions selected from positions 16, 17, 19, 20, 21, 22, 23, 24, and 34. In some embodiments, a peptide comprises substitutions relative to SEQ ID NO: 6 at one or more positions selected from positions 14, 18, 26, 27, 28, 29, 31, 32, and 33. In some embodiments, a peptide comprises a substitution relative to SEQ ID NO: 6 selected from S13L, S13Y, E15D, E16Q, L17Y, L17M, R19K, A22L, Y21L, L24S, L24Y, H26K, N29R, Y20L, Y21L, A22T, A22L, S23A, Y27L, L28I, L30H, L30A, Q34A, R35L, R35Y, R35V, R35L, Y36A, and Y36R, or combinations thereof. In some embodiments, a peptide comprises one or more non-natural amino acids, amino acid analogs, and/or peptide amino acids.

In some embodiments, provided herein are compositions comprising a peptide having 5 or fewer (e.g., 1, 2, 3, 4, 5, or ranges therebetween) substitutions relative to SEQ ID NO: 3, and less than 100% sequence identity with SEQ ID NO: 2. In some embodiments, the peptide comprises 70% or greater (e.g., >70%, >75%, >80%, >85%, >90%, >95%, 100%) sequence identity with SEQ ID NO: 3, and less than 100% sequence identity with SEQ ID NO: 2. In some embodiments, position 2 of SEQ ID NO: 3 is D, position 13 of SEQ ID NO: 3 is K, position 17 of SEQ ID NO: 3 is A, position 22 of SEQ ID NO: 3 is L, and/or position 23 of SEQ ID NO: 3 is A or R. In some embodiments, the peptide comprises 70% or greater (e.g., >70%, >75%, >80%, >85%, >90%, >95%, 100%) sequence identity with SEQ ID NO: 4 or 5, and less than 100% sequence identity with SEQ ID NO: 2. In some embodiments, the peptide comprises 70% or greater (e.g., >70%, >75%, >80%, >85%, >90%, >95%, 100%) sequence identity with SEQ ID NO: 9, SEQ ID NO: 10, or SEQ ID NO: 11, and less than 100% sequence identity with SEQ ID NO: 2. In some embodiments, the peptide comprises 70% or greater (e.g., >70%, >75%, >80%, >85%, >90%, >95%, 100%) sequence similarity (e.g., conservative or semi-conservative) with SEQ ID NO: 4 or 5, and less than 100% sequence identity with SEQ ID NO: 2. In some embodiments, the peptide comprises 100% sequence identity with SEQ ID NO: 30, but less than 100% sequence identity with SEQ ID NO: 2. In some embodiments, a PYY peptide comprises: (i) one or more of the amino acid residues in the peptide are D-enantiomers, (ii) the peptide comprises an N-terminally acetyl group, (iii) the peptide comprises a C-terminal amide group, (iv) the peptide comprises a one or more unnatural amino acids, (v) the peptide comprises a one or more amino acid analogs, and/or (vi) the peptide comprises a one or more peptoid amino acids. In some embodiments, the peptide exhibits enhanced stability relative to SEQ ID NO: 2. In some embodiments, the peptide exhibits enhanced anti-fungal-virulence activity relative to SEQ ID NO: 2. In some embodiments, the peptide is not a naturally occurring sequence.

In some embodiments, provided herein are pharmaceutical composition comprising a modified PYY peptide described herein and a pharmaceutically-acceptable carrier. In some embodiments, a pharmaceutical composition further comprises one or more additional therapeutic agents. In some embodiments, the one or more additional therapeutic agents are selected from the group consisting of an antibiotic agent, an antiparasitic agent, an antiviral agent, an antimycotic agent, and commensal microbes (e.g., a probiotic). In some embodiments, the pharmaceutical composition is formulated for oral, topical, vaginal, rectal, or injection administration.

In some embodiments, provided herein are methods for maintaining or inducing healthy commensal microflora of a subject comprising administering a pharmaceutical composition comprising a modified PYY peptide described herein to the subject. In some embodiments, healthy commensal microflora is induced or maintained on the skin, in the gut, in the oral cavity, or in the vaginal cavity. In some embodiments, the subject is at increased risk of a pathogenic fungal infection (e.g., immunocompromised, having received antibiotic treatment, etc.).

In some embodiments, provided herein are methods of treating or preventing a pathogenic infection in a subject comprising administering a pharmaceutical composition comprising a modified PYY peptide described herein to the subject. In some embodiments, the subject is at increased risk of a pathogenic fungal infection (e.g., immunocompromised, having received antibiotic treatment, etc.). In some embodiments, the subject is suffering from a pathogenic fungal infection.

In some embodiments, provided herein are methods of treating or preventing an inflammatory disease or condition (e.g., of the gastrointestinal tract) in a subject comprising administering a pharmaceutical composition comprising a modified PYY peptide described herein to the subject. In some embodiments, the disease or condition is ulcerative colitis or Crohn's disease.

In some embodiments, provided herein are devices comprising one or more surfaces coated with a composition comprising a modified PYY peptide described herein. In some embodiments, provided herein are methods of protecting a device from fungal growth or biofilm formation comprising administering a modified PYY peptide described herein to the device.

In some embodiments, provided herein is the use of a pharmaceutical composition or kit comprising a modified PYY peptide described herein for the treatment or prevention of a pathogenic fungal infection or inflammatory disease or condition. In some embodiments, provided herein is the use of a pharmaceutical composition or kit comprising a modified PYY peptide described herein in the manufacture of a medicament for the treatment or prevention of a pathogenic fungal infection or inflammatory disease or condition.

In some embodiments, provided herein is the use of a pharmaceutical composition or kit comprising a modified PYY peptide described herein for the establishment of maintenance of normal or healthy microbiota (e.g., on the skin, in the gut, in the mouth, in the blood, in the vagina). In some embodiments, provided herein is the use of a pharmaceutical composition or kit comprising a modified PYY peptide described herein in the manufacture of a medicament for the establishment of maintenance of normal or healthy microbiota (e.g., on the skin, in the gut, in the mouth, in the blood, in the vagina).

BRIEF DESCRIPTION OF THE DRAWINGS

FIG. 15. Sequence comparison of PYY (Homo sapiens) with neuropeptide Y (Homo sapiens) (top) and Amphibian skinPYY (Phyllomedusa bicolor) (bottom).

DEFINITIONS

Figure 1:
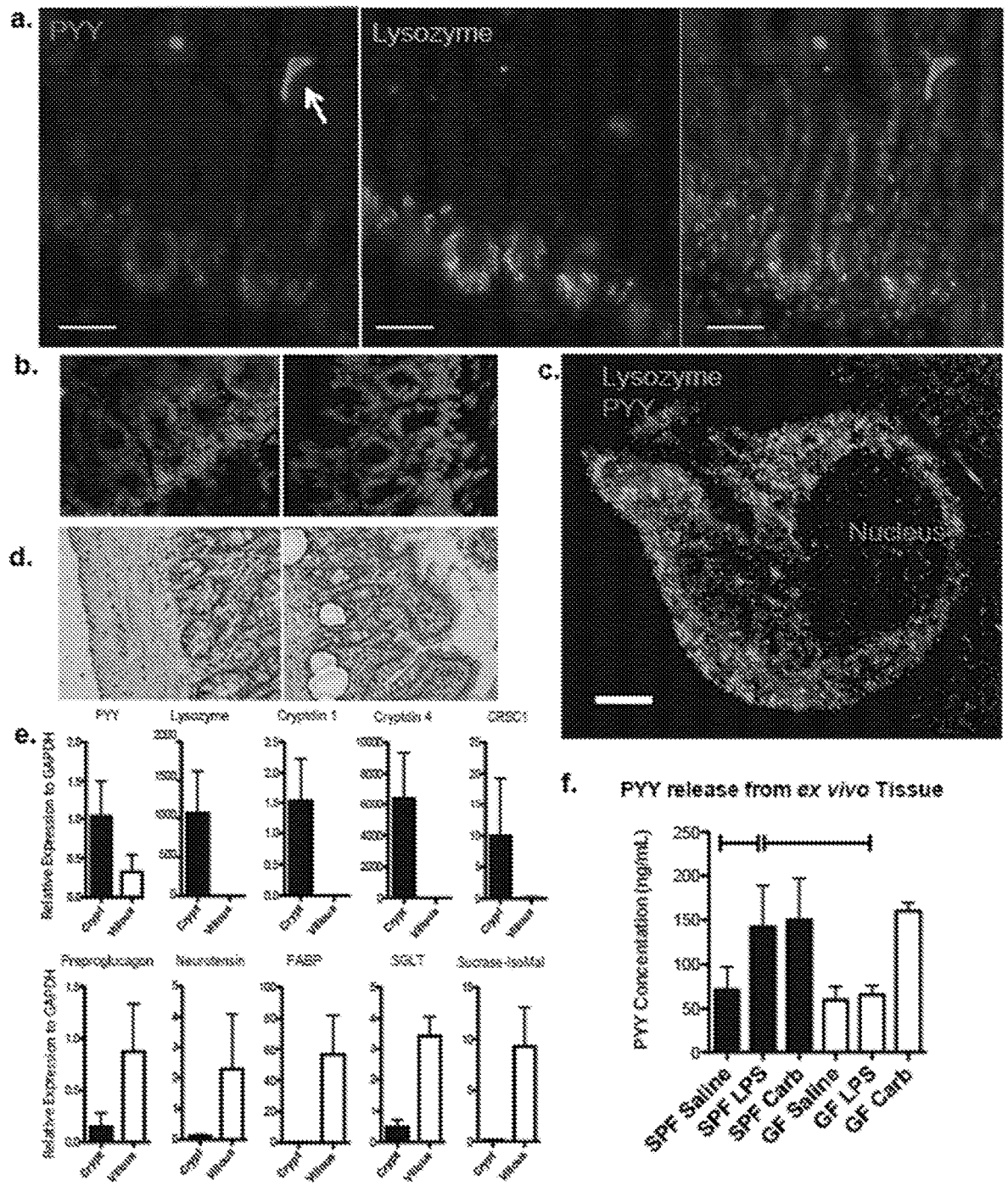
FIG. 1. Overview of evidence for PYY in Paneth cells in the small bowel. (A) PYY and Lysozyme immunofluorescence staining and merged image with DAPI nuclear staining. Scale bar=20 uM. (B) Paneth cell PYY staining before (left) and after (right) recombinant PYY quenching of primary PYY antibody. (C) Super resolution microscopy of PYY and Lysozyme in Paneth cell, showing separate compartmentalization of PYY from lysozyme. Scale bar=20 nm. (D) Representative Laser Capture Microscopy (LCM) for crypt and epithelium selection. (E) Gene expression of mucosal genes from LCM crypt (black bar) and epithelium (white bar). PYY expression was more similar to Paneth cell gene products than other classical enteroendocrine cell products (proproglucagon and neurotensin), and dissimilar to brush boarder enzymes. (F) Luminal PYY release from Specific-Pathogen Free (SPF) and Germ-free (GF) tissues following exposure to saline control, LPS, or the parasympathetic agonist, Carbamoylcholine (Carb). SPF tissues released PYY in response to LPS and Carb, while GF released only in response to Carb, consistent with the release of other antimicrobial products from these tissues.
Figure 1:
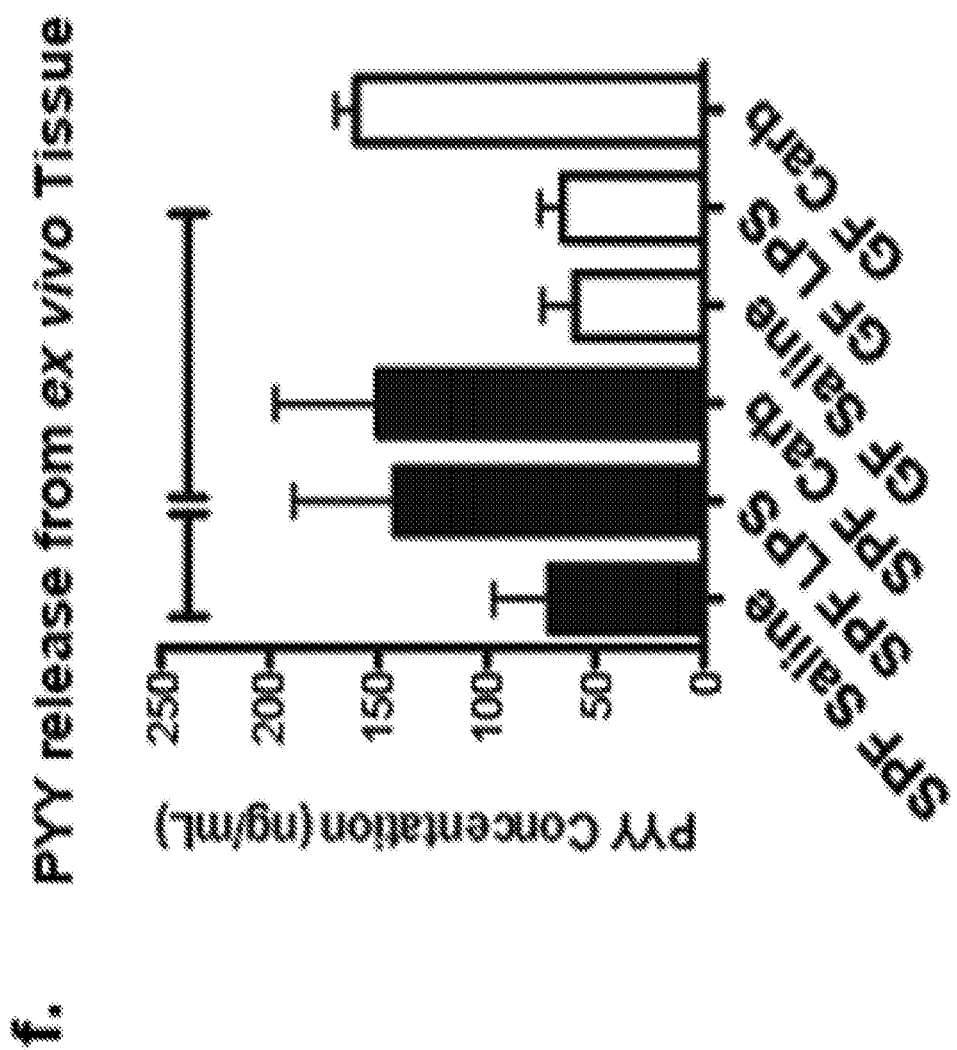

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a modified PYY peptide" is a reference to one or more modified PYY peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., aPYY peptide and a second agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "treating" refers to inhibiting a disease, disorder or condition (e.g., myocardial ischemia) in a subject. Treating the disease or condition includes ameliorating at least one symptom, reducing severity, impeding progress, and/or curing the subject of the disease or condition.

As used herein, the term "preventing" refers to prophylactic steps taken to reduce the likelihood of a subject (e.g., an at-risk subject) from contracting or suffering from a particular disease, disorder or condition (e.g., myocardial infarction). The likelihood of the disease, disorder or condition occurring in the subject need not be reduced to zero for the preventing to occur; rather, if the steps reduce the risk of a disease, disorder or condition across a population, then the steps prevent the disease, disorder or condition within the scope and meaning herein.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are typically of about 50 amino acids or less in length (e.g., 50, 45, 40, 35, 30, 25, 20, 15, 10, or less, or ranges therebetween (e.g., 10-30)). A peptide may comprise natural amino acids, non-natural amino acids, amino acid analogs, and/or modified amino acids. A peptide may be a subsequence of naturally occurring protein or a non-natural (artificial) sequence.

As used herein, the term "peptoid" refers to a class of peptidomimetics where the side chains are functionalized on the nitrogen atom of the peptide backbone rather than to the α-carbon.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine(S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine(S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO:Z" may have up to X substitutions relative to SEQ ID NO:Z, and may therefore also be expressed as "having X or fewer substitutions relative to SEQ ID NO:Z."

As used herein, the term "wild-type," refers to a gene or gene product (e.g., protein) that has the characteristics (e.g., sequence) of that gene or gene product isolated from a naturally occurring source, and is most frequently observed in a population. In contrast, the term "mutant" refers to a gene or gene product that displays modifications in sequence when compared to the wild-type gene or gene product. It is noted that "naturally-occurring mutants" are genes or gene products that occur in nature, but have altered sequences when compared to the wild-type gene or gene product; they are not the most commonly occurring sequence. "Synthetic" mutants are genes or gene products that have altered sequences when compared to the wild-type gene or gene product and do not occur in nature. Mutant genes or gene products may be naturally occurring sequences that are present in nature, but not the most common variant of the gene or gene product, or "synthetic," produced by human or experimental intervention.

As used herein, the term "PYY peptide" refers to the wild-type PYY sequence (SEQ ID NO: 1), naturally-occurring mutant versions thereof, and synthetic or modified (i.e., non-naturally occurring) versions thereof.

As used herein, the term "antimicrobial agent" is used to describe a therapeutic compound or bioactive agent which treats a microbial infection, for example, an infection caused by a bacteria, virus, protozoa or fungus. The antimicrobial agent may be an antibiotic, an antifungal agent, an antiviral or an antiprotozoal or antiparasitic agent (which may also be used to treat multicellular parasites).

As used herein, the terms "antibiotic" and "antibacterial agent" refer to a chemical agent which is active against bacteria. In common usage, an antibiotic is a substance or compound that kills or inhibits the growth of bacteria. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (e.g., penicillins, cephalosporins, cephems), or cell membrane (e.g., polymixins), or interfere with essential bacterial enzymes (e.g., quinolones, sulfonamides) usually are bactericidal in nature. Those which target protein synthesis such as the aminoglycosides, macrolides and tetracyclines are usually bacteriostatic. Three newer classes of antibiotics include: cyclic lipopeptides (e.g., daptomycin), glycylcyclines (e.g., tigecycline), and oxazolidinones (e.g., linezolid). Tigecycline is a broad-spectrum antibiotic, while the two others are useful for Gram-positive infections.

As used herein, the term "antiviral agent" refers to a chemical agent which is used to treat a viral infection. Antiviral drugs are a class of medication used specifically for treating viral infections, specific antivirals are useful for treating infection by specific viruses. Antivirals typically only inhibit virus development.

As used herein, the term "antifungal agent" refers to a therapeutic compound or bioactive agent which may be used to treat a fungal infection in a patient. An antifungal drug is a medication used inhibit the growth of or destroy fungi. Antifungal agents include, for example, polyene antifungals, imidazole, triazole and thiazole antifungals, allylamines, echinocandins, griseofulvin, flycystosine, undecylenic acid, among others.

As used herein, the term "antiparasitic agent" refers to a therapeutic compound or bioactive agent that is used to treat parasitic diseases including nematodes, cestodes, trematodes, infectious protozoa, and amoebas. Exemplary antiparasitic agents include: antinematodes (e.g., mebendazole, pyrantel pamoate, thiabendazole, diethycarbazine), anticestodes (e.g., niclosamide, praziquantel), antitrematodes (e.g., praziquantel), antiamoebics (e.g., rifampin and amphotericin B), antiprotozoals (e.g., melarsoprol, eflornithine, metronidazole and tinidazole), among others.

As used herein, the term "microbiota" refers to an assemblage of microorganisms localized to a distinct environment. Microbiota may include, for example, populations of various bacteria, eukaryotes (e.g., fungi), and/or archaea that inhabit a particular environment. For example, "gut microbiota," "vaginal microbiota," and "oral microbiota" refer to an assemblage of one or more species of microorganisms that are localized to, or found in, the gut, vagina, or mouth, respectively.

"Normal microbiota" refers to a population of microorganisms that localize in a particular environment in a normal, non-pathological, non-virulent state. A "normal microbiota" has normal membership and normal relative abundance.

"Abnormal microbiota" refers to a population of various microorganisms (or forms of microorganisms) that localize in a particular environment in a subject suffering from or at risk of a pathological condition. Abnormal microbiota differs from normal microbiota in terms of identity (e.g., membership), absolute amount, or relative amount (e.g., relative abundance) of the various microbes.

As used herein, the terms "commensal microbe" or "commensal form" refer to a microorganism (e.g., fungus) or form thereof (e.g., hyphae form) that is non-pathogenic to a host and is part of the normal microbiota of the host.

As used herein, the terms "microbial agent," "commensal microbial agent," and "probiotic" refer to compositions comprising a microbe or population of multiple different microbes for administration to a subject.

DETAILED DESCRIPTION

Provided herein are compositions and methods for treating and/or preventing pathogenic fungal infection and for maintenance of microbiome commensalism. In particular, provided herein are compositions comprising modified peptide YY (PYY) peptides and therapeutic and/or prophylactic methods of use thereof. In some embodiments, provided herein are modified PYY peptides that exhibit one or more of enhanced antifungal activity, enhanced biostability, enhanced bioavailability, altered antimicrobial characteristics, etc.

Experiments conducted during development of embodiments herein demonstrate that PYY is also found in discrete dense core granules of human and murine Paneth cells. Paneth cells are the major producers of intestinal antimicrobial peptides (AMPs), including lysozyme, sPLA2-IIA, and defensins (and murine cryptdins) (Ref. 9; incorporated by reference in its entirety), which are released apically into the gut lumen. Upon innate immune and cholinergic stimulation, PYY is released into the intestinal lumen, consistent with a role as an anti-microbial peptide (AMP).

Structurally, PYY resembles a class of AMPs, comprising two anti-parallel helices, an N-terminal polyproline helix extending 14 residues, and an amphipathic C-terminal polycationic α-helix extending the final 22 residues. The α-helix fragment resembles other cationic antimicrobial compounds, including the amphibian magainin-2 and mammalian cathelicidin (FIG. 11).

In contrast to other AMPs, PYY has little anti-bacterial activity and minimal effects on the commensal yeast form. However, experiments conducted during development of embodiments herein demonstrate that PYY instead targets the virulent form of polyphenic fungi (e.g., *Candida albicans*), impairing cell integrity by permeabilizing the terminal hyphal cells and inhibiting virulence gene expression and biofilm formation.

Experiments conducted during development of embodiments herein also demonstrate that chronic *C. albicans* colonization is greater in PYY-deficient mice (PYY$^{-/-}$ mice) but blocked by administration of PYY, and that PYY is an evolutionarily conserved antimicrobial peptide which that role in controlling virulence of polyphenic fungi (e.g., *C. albicans*) and maintaining fungal commensalism in the gut. PYY permeabilizes *Candida* hyphal tips while allowing yeast forms of *Candida* to continue growing unchecked is an elegant system for the containment of commensal fungi. In contrast to other known antimicrobial peptides, which act by non-specifically targeting bacteria for elimination, PYY discriminates between commensal and virulent forms of the same strain. This allows PYY to target a species based on its functional/phenotypic state, not its genomic identity. The terminal hyphal cells of *C. albicans* are distinct in the composition of their cell wall when compared to other *C. albicans* cells. It is from the tip of the hyphae that *C. albicans* secrete proteases that lead to biofilm formation. Additionally, hyphal tips exhibit thigmatotropism and it is from the hyphal tip that growth of the hyphae occurs. The fibers of chitin and glucan chains that comprise the cell wall of the terminal hyphal tip are not crosslinked as those in the rest of the cell wall are.

Some embodiments herein are described in connection with *Candida albicans*; however, embodiments herein are not so limited. Rather, the embodiments described herein may find use in the treatment or prevention of infection and/or pathogenesis by fungi more broadly, including dimorphic or other polymorphic fungi (e.g., fungi capable of adopting a hyphae form), such as, but not limited to *Candida auris, Cryptococcus neoformans, Crypotococcus laurentii, Cryptococcus albidus, Cryptococcus gattii, Pneumocystis jirovecii, Stachybotry chartarum, Coccidioides immitis, Paracoccidioides brasiliensis, Ustilago maydis, Blastomyces dermatitidis, Histoplasma capsulatum, Sporothrix schenckii*, and *Emmonsia* sp. In some embodiments, the fungi are resistant to one or more antifungal compounds including but not limited to clotrimazole, econazole, ketoconazole, itraconazole, fluconazole, posaconazole, voriconazole, miconazole, tioconazole, terbinafine, and amorolfine. Embodiments described herein as relating specifically to *C. albicans* should be understood to apply more broadly to embodiments encompassing polymorphic fungi, dimorphic fungi, and/or pathogenic fungi in general. By way of example, more detail in *C. albicans* is provided below.

*Candida albicans* is an opportunistic fungal pathogen that is responsible for candidiasis in human hosts. *C. albicans* grow in several different morphological forms, ranging from unicellular budding yeast to true hyphae with parallel-side wall. *C. albicans* live as harmless commensals in the gastrointestinal and genitourinary tract. However, overgrowth of these organisms, expression of various virulence factors, or conversion to virulent forms, leads to disease. Pathogenesis most frequently occurs in immunocompromised individuals, such as HIV-infected victims, transplant recipients, chemotherapy patients, and infants (e.g., low birth-weight infants). The three major forms of *C. albicans*-caused disease are oropharyngeal candidiasis, vulvovaginal candidiasis, and invasive candidiasis. For oropharyngeal candidiasis, infection occurs in the mouth or throat, and is identified by white plaque growth on oral mucous membranes. Vulvovaginal candidiasis or a "yeast infection" is the overgrowth of *C. albicans* in the vagina, and results in rash, itchiness, and discharge from the genital region. Lastly, invasive candidiasis occurs when the fungal pathogen enters the bloodstream and can easily spread to organs throughout the body. Pathogenic *C. albicans* infection typically begins with the commensal population of *C. albicans* in the normal microflora. Candidiasis is caused by the abnormal growth in *C. albicans*, which may be due to a change in the environment (e.g., gut) or an imbalance of the microbiota. Events that can spark an imbalance include antibiotic use (e.g., decrease in the amount of *lactobacillus* bacteria, other infections, impaired immune system, changes to diet, and other diseases or conditions.

*Candida albicans* is a polymorphic fungus that can grow in several different forms, primarily yeast, pseudohyphae, and hyphae. The hyphae form is more prevalent for an infection (e.g., more virulent, more pathogenic), while the yeast form is more common in the passing of *C. albicans* between individuals. Several factors can cause a change in morphology, such as pH differences, temperature changes, carbon dioxide levels, starvation, and quorum-sensing molecules (farnesol, tyrosol, and dodecanol).

*Candida albicans* have special sets of glycosylphosphatidylinositol (GPI)-linked cell surface glycoproteins that allow it to adhere to the surfaces of microorganisms. Adhesion genes are upregulated during an infection of oral and vaginal epithelial cells, and can also be involved with the invasion of *C. albicans* into host epithelial and endothelial cells. Invasion genes mediate binding to host ligands, such as E-cadherin on epithelial cells and N-cadherin on endothelial cells, and it induces host cells to engulf the fungal pathogen. Another method of invasion is the active penetration of *C. albicans* hyphae into host cells.

*Candida albicans* form biofilms on living and non-living surfaces, such as mucosal membranes and medical devices (e.g., catheters, surgical instruments, implants, stents, medical tubing, etc.). After the adherence of yeast cells to the surface, hyphae cells develop on the biofilm surface.

*Candida albicans* secrete 3 main classes of hydrolases: proteases, phospholipases and lipases, which facilitate the pathogen's active penetration into host cells and the uptake of extracellular nutrients from the environment.

*Candida albicans* are usually found in the gastrointestinal microbiome of healthy individuals, and in this environment, nutrient levels are relatively high. However, during niche changes in the course of an infection, available nutrient levels also change. Consequently, the fungus quickly undergoes metabolic adaption, such as their glycolysis, gluconeogenesis, and starvation responses. *C. albicans* can infect almost every organ in a human host through the bloodstream, providing candidemia's higher mortality rate.

The compositions (e.g., PYY peptides), methods of treatment and prevention or infection, and methods of maintaining or establishing healthy/normal microbiota (e.g., in the gut, in the vagina, in the mouth, on the skin, in the blood, etc.) find use with, for example, infectious fungal microorganisms of any of a variety of yeasts, such as, *Candida* species fungi (e.g., *Candida albicans, Candida tropicalis, Candida parapsilosis, Candida glabrata, Candida krusei, Candida pseudotropicalis, Candida lusitaniae, Candida auris,* or *Candida guilliermondi*), *Cryptococcus* species fungi (e.g., *Cryptococcus neoformans*), or the hyphae phases of dimorphic or polymorphic fungi. Dimorphic and polymorphic fungi include, *Candida* species, *Histoplasma capsulatum, Blastomyces dermatitidis, Paracoccidioides brasiliensis, Coccidioides immitis, Sporothrix schenckii,* etc. In some embodiments, the fungi are resistant to one or more antifungal compounds including but not limited to clotrimazole, econazole, ketoconazole, itraconazole, fluconazole, posaconazole, voriconazole, miconazole, tioconazole, terbinafine, and amorolfine. In some embodiments, monomorphic fungal infections are treated/prevented with the methods and compositions herein.

In some embodiments, provided herein are PYY peptides (e.g., modified PYY peptides (e.g., having less than 100% sequence identity with SEQ ID NO: 1, SEQ ID NO: 2, and/or SEQ ID NO: 6)), and methods of use thereof for: (i) the treatment of a pathogenic infection (e.g., fungal infection, polymorphic fungal infection, *C. albicans* pathogenic infection, etc.), (ii) prevention of a pathogenic infection (e.g., in a healthy subject, in a subject at risk for fungal infection, etc.), (iii) maintenance of healthy/normal microbiota in a subject (e.g., allowing colonization by non-virulent forms of fungi, while preventing the formation and/or spread of virulent forms (e.g., hyphae)), and/or (iv) establishing/re-establishing healthy/normal microbiota in a subject.

In some embodiments, a PYY peptide comprises at least 70% (e.g., >70%, >75%, >80%, <85%, >90%, >95%) sequence identity to SEQ ID NO: 3, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%) sequence similarity (e.g., conservative or semi-conservative) to SEQ ID NO: 3, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 3.

In some embodiments, a PYY peptide comprises at least 70% (e.g., >70%, >75%, >80%, <85%, >90%, >95%) sequence identity to SEQ ID NO: 4, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%) sequence similarity (e.g., conservative or semi-conservative) to SEQ ID NO: 4, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 4.

In some embodiments, a PYY peptide comprises at least 70% (e.g., >70%, >75%, >80%, <85%, >90%, >95%) sequence identity to SEQ ID NO: 5, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%) sequence similarity (e.g., conservative or semi-conservative) to SEQ ID NO: 5, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 5.

In some embodiments, an amino acid of a PYY peptide at a position relative to $X_1$ of SEQ ID NO: 3 is not E. In some embodiments, an amino acid of a PYY peptide at a position relative to $X_2$ of SEQ ID NO: 3 is not H. In some embodiments, an amino acid of a PYY peptide at a position relative to $X_3$ of SEQ ID NO: 3 is not L. In some embodiments, an amino acid of a PYY peptide at a position relative to $X_4$ of SEQ ID NO: 3 is not R. In some embodiments, an amino acid of a PYY peptide at a position relative to $X_5$ of SEQ ID NO: 3 is not Y.

In some embodiments, an amino acid of a PYY peptide at a position relative to position 2 ($X_1$) of SEQ ID NO: 3 is D. In some embodiments, an amino acid of a PYY peptide at a position relative to position 13 ($X_2$) of SEQ ID NO: 3 is K. In some embodiments, an amino acid of a PYY peptide at a position relative to position 17 ($X_3$) of SEQ ID NO: 3 is A. In some embodiments, an amino acid of a PYY peptide at a position relative to position 22 ($X_4$) of SEQ ID NO: 3 is L. In some embodiments, an amino acid of a PYY peptide at a position relative to position 23 ($X_5$) of SEQ ID NO: 3 is A or R.

In some embodiments, a PYY peptide comprises at least 70% (e.g., >70%, >75%, >80%, <85%, >90%, >95%, 100%) sequence identity to SEQ ID NO: 9, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 9, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 9.

In some embodiments, a PYY peptide comprises at least 70% (e.g., >70%, >75%, >80%, <85%, >90%, >95%, 100%) sequence identity to SEQ ID NO: 10, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 10, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 10.

In some embodiments, a PYY peptide comprises at least 70% (e.g., >70%, >75%, >80%, <85%, >90%, >95%, 100%) sequence identity to SEQ ID NO: 11, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 11, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 11.

In some embodiments, a PYY peptide comprises at least 70% (e.g., >70%, >75%, >80%, <85%, >90%, >95%, 100%) sequence identity to SEQ ID NO: 26, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 26, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 26.

In some embodiments, a PYY peptide comprises at least 70% (e.g., >70%, >75%, >80%, <85%, >90%, >95%, 100%) sequence identity to SEQ ID NO: 29, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 29, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 29.

In some embodiments, a PYY peptide comprises at least 70% (e.g., >70%, >75%, >80%, <85%, >90%, >95%, 100%) sequence identity to SEQ ID NO: 31, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 31, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 31.

In some embodiments, a PYY peptide comprises at least 70% (e.g., >70%, >75%, >80%, <85%, >90%, >95%, 100%) sequence identity to SEQ ID NO: 34, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 34, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 34.

In some embodiments, a PYY peptide comprises at least 70% (e.g., >70%, >75%, >80%, <85%, >90%, >95%, 100%) sequence identity to SEQ ID NO: 35, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 35, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 35.

In some embodiments, a PYY peptide comprises at least 70% (e.g., >70%, >75%, >80%, <85%, >90%, >95%, 100%) sequence identity to SEQ ID NO: 36, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 36, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 36.

In some embodiments, a PYY peptide comprises at least 70% (e.g., >70%, >75%, >80%, <85%, >90%, >95%, 100%) sequence identity to SEQ ID NO: 37, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 37, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 37.

In some embodiments, a PYY peptide comprises at least 70% (e.g., >70%, >75%, >80%, <85%, >90%, >95%, 100%) sequence identity to SEQ ID NO: 38, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 38, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 38.

In some embodiments, a PYY peptide comprises at least 70% (e.g., >70%, >75%, >80%, <85%, >90%, >95%, 100%) sequence identity to one of SEQ ID NOS: 24-38, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to one of SEQ ID NOS: 24-38, but less than 100% sequence identity to SEQ ID NO: 1, SEQ ID NO: 2, and/or SEQ ID NO: 6. In some embodiments, a PYY peptide comprises 1-7 substitutions relative to one of SEQ ID NOS: 24-38.

In some embodiments, a PYY peptide comprises at least 70% (e.g., >70%, >75%, >80%, <85%, >90%, >95%, 100%) sequence identity to SEQ ID NO: 39, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 39, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 39. In some embodiments, each "X" residue in SEQ ID NO: 39 is independently selected from any amino acid (e.g., natural amino acid, unnatural amino acid, amino acid analog, modified amino acid, etc.). In some embodiments, one or more "X" residues of SEQ ID NO: 39 are selected from a particular group or class of amino acid residues (e.g., non-polar, charged, etc.). In some embodiments, an amino acid of a PYY peptide at a position relative to $X_1$ of SEQ ID NO: 39 is not S. In some embodiments, an amino acid of a PYY peptide at a position relative to $X_2$ of SEQ ID NO: 39 is not E. In some embodiments, an amino acid of a PYY peptide at a position relative to $X_3$ of SEQ ID NO: 39 is not H. In some embodiments, an amino acid of a PYY peptide at a position relative to $X_4$ of SEQ ID NO: 39 is not N. In some embodiments, an amino acid of a PYY peptide at a position relative to $X_5$ of SEQ ID NO: 39 is not L. In some embodiments, an amino acid of a PYY peptide at a position relative to $X_6$ of SEQ ID NO: 39 is not R. In some embodiments, an amino acid of a PYY peptide at a position relative to $X_7$ of SEQ ID NO: 39 is not Y.

In some embodiments, a PYY peptide comprises at least 70% (e.g., >70%, >75%, >80%, <85%, >90%, >95%, 100%) sequence identity to SEQ ID NO: 40, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 40, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 40. In some embodiments, each "X" residue in SEQ ID NO: 40 is independently selected from any amino acid (e.g., natural amino acid, unnatural amino acid, amino acid analog, modified amino acid, etc.). In some embodiments, one or more "X" residues of SEQ ID NO: 40 are selected from a particular group or class of amino acid residues (e.g., non-polar, charged, etc.). In some embodiments, an amino acid of a PYY peptide at a position relative to $X_1$ of SEQ ID NO: 40 is not S. In some embodiments, an amino acid of a PYY peptide at a position relative to $X_2$ of SEQ ID NO: 40 is not E. In some embodiments, an amino acid of a PYY peptide at a position relative to $X_3$ of SEQ ID NO: 40 is not Y. In some embodiments, an amino acid of a PYY peptide at a position relative to $X_4$ of SEQ ID NO: 40 is not Y. In some embodiments, an amino acid of a PYY peptide at a position relative to $X_5$ of SEQ ID NO: 40 is not A. In some embodiments, an amino acid of a PYY peptide at a position relative to $X_6$ of SEQ ID NO: 40 is not S. In some embodiments, an amino acid of a PYY peptide at a position relative to $X_7$ of SEQ ID NO: 40 is not H. In some embodiments, an amino acid of a PYY peptide at a position relative to $X_x$ of SEQ ID NO: 40 is not Y. In some embodiments, an amino acid of a PYY peptide at a position relative to $X_9$ of SEQ ID NO: 40 is not L. In some embodiments, an amino acid of a PYY peptide at a position relative to $X_{10}$ of SEQ ID NO: 40 is not R.

In some embodiments, a PYY peptide comprises at least 70% (e.g., >70%, >75%, >80%, <85%, >90%, >95%, 100%) sequence identity to SEQ ID NO: 41, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 41, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 41. In some embodiments, each "X" residue in SEQ ID NO: 41 is independently selected from any amino acid (e.g., natural amino acid, unnatural amino acid, amino acid analog, modified amino acid, etc.). In some embodiments, one or more "X" residues of SEQ ID NO: 41 are selected from a particular group or class of amino acid residues (e.g., non-polar, charged, etc.). In some embodiments, an amino acid of a PYY peptide at a position relative to $X_1$ of SEQ ID NO: 41 is not S. In some embodiments, an amino acid of a PYY peptide at a position relative to $X_2$ of SEQ ID NO: 41 is not E. In some embodiments, an amino acid of a PYY peptide at a position relative to $X_3$ of SEQ ID NO: 41 is not Y. In some embodiments, an amino acid of a PYY peptide at a position relative to $X_4$ of SEQ ID NO: 41 is not Y. In some embodiments, an amino acid of a PYY peptide at a position relative to $X_5$ of SEQ ID NO: 41 is not A. In some embodiments, an amino acid of a PYY peptide at a position relative to $X_6$ of SEQ ID NO: 41 is not S. In some embodiments, an amino acid of a PYY peptide at a position relative to $X_7$ of SEQ ID NO: 41 is not H. In some embodiments, an amino acid of a PYY peptide at a position relative to Xx of SEQ ID NO: 41 is not Y. In some embodiments, an amino acid of a PYY peptide at a position relative to $X_9$ of SEQ ID NO: 41 is not L.

In some embodiments, a PYY peptide comprises at least 70% (e.g., >70%, >75%, >80%, <85%, >90%, >95%, 100%) sequence identity to SEQ ID NO: 42, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 42, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 42.

In some embodiments, a PYY peptide comprises at least 70% (e.g., >70%, >75%, >80%, <85%, >90%, >95%, 100%) sequence identity to SEQ ID NO: 43, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 43, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 43. In some embodiments, each "X" residue in SEQ ID NO: 43 is independently selected from any amino acid (e.g., natural amino acid, unnatural amino acid, amino acid analog, modified amino acid, etc.). In some embodiments, one or more "X" residues of SEQ ID NO: 43 are selected from a particular group or class of amino acid residues (e.g., non-polar, charged, etc.). In some embodiments, a PYY peptide comprises at least 70% (e.g., >70%, >75%, >80%, <85%, >90%, >95%, 100%) sequence identity to SEQ ID NO: 44, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 44, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 44. In some embodiments, each "X" residue in SEQ ID NO: 44 is independently selected from any amino acid (e.g., natural amino acid, unnatural amino acid, amino acid analog, modified amino acid, etc.). In some embodiments, one or more "X" residues of SEQ ID NO: 44 are selected from a particular group or class of amino acid residues (e.g., non-polar, charged, etc.).

In some embodiments, a PYY peptide comprises at least 70% (e.g., >70%, >75%, >80%, <85%, >90%, >95%, 100%) sequence identity to SEQ ID NO: 45, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 45, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 45. In some embodiments, each "X" residue in SEQ ID NO: 45 is independently selected from any amino acid (e.g., natural amino acid, unnatural amino acid, amino acid analog, modified amino acid, etc.). In some embodiments, one or more "X" residues of SEQ ID NO: 45 are selected from a particular group or class of amino acid residues (e.g., non-polar, charged, etc.).

In some embodiments, a PYY peptide comprises at least 70% (e.g., >70%, >75%, >80%, <85%, >90%, >95%, 100%) sequence identity to SEQ ID NO: 46, but less than 100% sequence identity to SEQ ID NO: 1, SEQ ID NO: 2, and/or SEQ ID NO: 6. In some embodiments, a PYY peptide comprises at least 70% (e.g., >70%, >75%, >80%, <85%, >90%, >95%, 100%) sequence similarity (e.g., conservative or semi-conservative) to SEQ ID NO: 46, but less than 100% sequence identity to SEQ ID NO: 1, SEQ ID NO: 2, and/or SEQ ID NO: 6. In some embodiments, a PYY peptide comprises 1-7 substitutions relative to SEQ ID NO: 46.

In some embodiments, any substitution relative to one of SEQ NOS: 3-46 is independently a conservative, semi-conservative, or non-conservative substitution. In some embodiments, all substitutions relative to one of SEQ NOS: 3-46 are conservative or semi-conservative substitutions.

In some embodiments, one or more positions of a PYY peptide are identical or a conserved substitution relative to evolutionarily conserved sequences between PYY and Amphibian skinPYY (SEQ ID NO: 43) neuropeptide Y (NPY) (SEQ ID NO: 44), or both (SEQ ID NO: 45).

In some embodiments, a PYY peptide is 10-50 amino acids in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and any ranges therein). In some embodiments, a PYY peptide comprises at least 1 mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, and any ranges therein) from the wild-type or a natural PYY peptide sequence over the length of the peptide. In some embodiments, a PYY peptide comprises at least 1 non-conservative mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or more, and any ranges therein) from the wild-type or a natural PYY peptide sequence over the length of the peptide. In some embodiments, a PYY peptide comprises at least 1 conservative mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, and any ranges therein) from the wild-type or a natural PYY peptide sequence over the length of the peptide. In some embodiments, a PYY peptide comprises at least 1 semi-conservative mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, and any ranges therein) from the wild-type or a PYY peptide sequence over the length of the peptide.

In some embodiments, all amino acids within a PYY peptide are natural amino acids. In some embodiments, a PYY peptide comprises a combination of natural amino acids, unnatural amino acids, amino acid analogs, D-amino acids, and/or peptoid amino acids. In some embodiments, a PYY peptide comprises one or more modifications, such as acetylation, conjugation to palmitic acid, amidation, cyclization, phosphorylation, PEGylation, lipidization, esterification, glycosylation, etc.

PYY has been studied as a gut peptide hormone. Gut hormones are frequently amidated at their C-terminus, with the traditional carboxyl group being replaced by an amide. Indeed, PYY was first identified in a search for C-terminally amidated peptides (Tatemoto and Mutt, Nature. 1980; 285 (5764): 417-8; herein incorporated by reference in its entirety). Amidation of gut hormones such as PYY that are produced by L-cells in the small intestine is accomplished by peptidylglycine α-amidating monooxygenase (PAM). The C-terminal amidation of gut hormones by PAM is frequently required for their hormonal function. However, experiments conducted during development of embodiments herein demonstrate that C-terminal amidation of a PYY peptide decreases the antifungal activity.

In some embodiments, a PYY peptide comprises one or more modifications (e.g., post-translational modifications, post-synthesis modification, incorporation of amino acids comprising a modification, etc.). Exemplary modifications (e.g., in vivo or in vitro) include, but are not limited to: phosphorylation (e.g., reversible phosphorylation, phosphorylation of serine, threonine, tyrosine, etc.); glycosylation (e.g., aspargine-linked (N-linked), serine/threonine-linked (O-linked), etc.), such as N-glycosylation, O-glycosylation, glypiation, C-glycosylation, phosphoglycosylation, etc.; ubiquitination (e.g., of lysine); S-nitrosylation (e.g., of free cysteine residues to form S-nitrothiols (SNOs)); methylation (e.g., (N-methylation, O-methylation, etc.); N-acetylation (e.g., at an N-terminal methionine, at the ε-$NH_2$ of lysine, etc.), lipidation (e.g., C-terminal glycosyl phosphatidylinositol (GPI) anchor, N-terminal myristoylation, S-myristoylation, S-prenylation, S-palmitoylation, etc.); lipoylation, deimination (e.g., of arginine to citrulline), deamidation (e.g., conversion of glutamine to glutamic acid, conversion of asparagine to aspartic acid, replacement of a C-terminal amide group with a C-terminal carboxy group, etc.); eliminylation (e.g., conversion to an alkene by beta-elimination of phosphothreonine and phosphoserine, dehydration of threonine and serine, etc.); disulfide bridging; proteolytic cleavage; isoaspartate formation (e.g., via the cyclisation of asparagine or aspartic acid amino-acid residues); racemization (e.g., of serine, of alanine, of methionine, etc.); protein splicing (e.g., self-catalytic removal of inteins); glycation; carbamylation (e.g., the addition of isocyanic acid to the N-terminus or a lysine side chain); carbonylation; isopeptide bond formation; sulfation (e.g., the addition of a sulfate group to a tyrosine); succinylation (e.g., addition of a succinyl group to lysine); S-sulfonylation (e.g., covalent addition of three oxygen atoms to the thiol group of a cysteine residue); S-sulfinylation (e.g., covalent addition of two oxygen atoms to the thiol group of a cysteine residue); S-sulfenylation (e.g., covalent addition of one oxygen atom to the thiol group of a cysteine residue); S-glutathionylation; pyroglutamate formation; propionylation; adenylylation (e.g., addition of an adenylyl moiety (e.g., to tyrosine (O-linked), or histidine and lysine (N-linked), etc.)); nucleotide addition (e.g., ADP-ribosylation, etc.); iodination (e.g., addition of an iodine atom to the aromatic ring of a tyrosine residue); hydroxylation (e.g., addition of an oxygen atom to the side-chain of a Pro or Lys residue); malonylation; butyrylation; amidation (e.g., C-terminal); alkylation (e.g., addition of an ethyl group); acylation (e.g. O-acylation (esters), N-acylation (amides), S-acylation (thioesters), etc.); biotinylation; carbamylation; oxidation (e.g., addition of one or more oxygen atoms to a susceptible side-chain (e.g., Met, Trp, His or Cys residues); pegylation; etc.

In some embodiments, one or more (e.g., 1, 2, 3, 4, etc.) of the serine and/or threonine residues of the PYY peptide comprise O-linked glycosylations.

C-terminally amidated PYY peptides exhibited significant decrease in efficacy as assessed by biofilm assay. In some embodiments, the peptides described herein are deamidated at the C-terminus.

In some embodiments, the amino and/or carboxy termini of the PYY peptides described herein are modified. Terminal modifications are useful, for example, to reduce susceptibility to proteinase digestion, and therefore can serve to prolong half-life of the peptides in solution, particularly in biological fluids where proteases may be present.

Amino terminus modifications include methylation (e.g., —$NHCH_3$ or —$N(CH_3)_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—$SO_2$—, where R is selected from the group consisting of alkyl, aryl, heteroaryl, alkyl aryl, and the like, and similar groups. In some embodiments, a desamino acid is added at the N-terminus (replacing the N-terminal amino group) to decrease susceptibility to proteases or to restrict the conformation of the peptide. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. In some embodiments, peptides described herein are cyclized. In some embodiments, a desamino or descarboxy residue is added or incorporated at the termini of the peptide (e.g., replacing the terminal carboxyl group) to decrease susceptibility to proteases or to restrict the conformation of the peptide. Methods of circular peptide synthesis are known in the art, for example, in U.S. patent application No. 20090035814; Muralidharan and Muir, 2006, Nat Methods, 3:429-38; and Lockless and Muir, 2009, Proc Natl Acad Sci USA. June 18, Epub; incorporated by reference in their entireties. C-terminal functional groups of the PYY peptides described herein include amide, amide lower alkyl, amide di(lower alkyl), lower alkoxy, hydroxy, and carboxy, and the lower ester derivatives thereof, and the pharmaceutically acceptable salts thereof.

In some embodiments, one or more amino acid side chains of a PYY peptide are modified with groups such a branched or linear $alkyl_{1-6}$ chain, cyclic 4-, 5-, 6-, to 7-membered alkyl, amide, alkoxy, hydroxy, carboxy, ester, 4-, 5-, 6-, to 7-membered heterocycles, etc. In particular embodiments, prolines are modified to exhibit ring sizes of 4, 6, or 7 members (e.g., selected from C, N, O, and S). In some embodiments, cyclic groups are saturated or unsaturated, and if unsaturated, are aromatic or non-aromatic. Heterocyclic groups may contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. In some embodiments, these heterocyclic groups are substituted or unsubstituted. In some embodiments, when a group is substituted, if not otherwise specified, the substituent is selected from alkyl, halogen, $CF_3$, OH, SH, $NH_2$, CN, substituted or unsubstituted phenyl, or other common organic groups. Other methods of peptide modification are described, for example, in Hruby, et al. (1990) Biochem J. 268:249-262; incorporated by reference in its entirety.

In some embodiments, a modified PYY peptide exhibits enhanced characteristics relative to wild-type PYY. In some embodiments, a modified PYY peptide exhibits enhanced solubility, bioavailability, antifungal activity (e.g., anti-C.

*albicans* activity), activity against the hyphal form of a fungus (e.g., *C. albicans*), structural stability, biostability, bioavailability, etc.

As discussed herein, in some embodiments, PYY peptides are provided having variations from natural PYY and/or from the sequences described herein. Embodiments are not limited by specific sequences and/or substitutions described herein. In some embodiments, peptides meeting limitations described herein (e.g., anti-fungal-virulence activity, anti-microbial activity, anti-fungal activity, etc.) and having substitutions not explicitly described are within the scope of embodiments herein. In some embodiments, the PYY peptides described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize active conformations). In some embodiments, the PYY peptides described herein may be modified by conservative or semi conservative residue substitutions. In some embodiments, such substitutions provide subtle changes while preserving the local environment of the residue. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is $C_1$-$C_4$ alkyl. Furthermore, one or more side groups, or terminal groups, may be protected by protective groups known to the ordinarily-skilled peptide chemist. The α-carbon of an amino acid may be mono- or dimethylated.

In some embodiments, any embodiments described herein may comprise peptidomimetics corresponding to the PYY peptides described herein with various modifications that are understood in the field. In some embodiments, residues in the PYY peptides sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties. In some embodiments, residues having a side chain that is positively charged under physiological conditions, or residues where a positively-charged side chain is desired, are substituted with a residue including, but not limited to: lysine, homolysine, 8-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methyl-arginine), E-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methylhistidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges. In some embodiments, residues having a side chain that is neutral/polar under physiological conditions, or residues where a neutral side chain is desired, are substituted with a reside including, but not limited to: asparagine, cysteine, glutamine, serine, threonine, tyrosine, citrulline, N-methylserine, homoserine, allo-threonine and 3,5-dinitro-tyrosine, and β-homoserine. Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, PYY peptides are isolated and/or purified (or substantially isolated and/or substantially purified). Accordingly, in such embodiments, PYY peptides are provided in substantially isolated form. In some embodiments, PYY peptides are isolated from other peptides and/or polypeptides as a result of solid phase peptide synthesis, for example. Alternatively, PYY peptides can be substantially isolated from other proteins after cell lysis from recombinant production. Standard methods of protein purification (e.g., HPLC) can be employed to substantially purify PYY peptides.

In some embodiments, PYY peptides may be formulated in a number of different formulations, depending on the desired use. For example, where the peptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, PYY peptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46,47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In various embodiments, the PYY peptides disclosed herein are derivatized by conjugation to one or more polymers or small molecule substituents.

In certain of these embodiments, the PYY peptides described herein are derivatized by coupling to polyethylene glycol (PEG). Coupling may be performed using known processes. See, Int. J. Hematology, 68:1 (1998); Bioconjugate Chem., 6:150 (1995); and Crit. Rev. Therap. Drug Carrier Sys., 9:249 (1992) all of which are incorporated herein by reference in their entirety. Those skilled in the art, therefore, will be able to utilize such well-known techniques for linking one or more polyethylene glycol polymers to the PYY peptides described herein. Suitable polyethylene glycol polymers typically are commercially available or may be made by techniques well known to those skilled in the art. The polyethylene glycol polymers preferably have molecular weights between 500 and 20,000 and may be branched or straight chain polymers.

The attachment of a PEG to a PYY peptide described herein can be accomplished by coupling to amino, carboxyl or thiol groups. These groups will typically be the N- and C-termini and on the side chains of such naturally occurring amino acids as lysine, aspartic acid, glutamic acid and cysteine. Since the PYY peptides of the present disclosure can be prepared by solid phase peptide chemistry techniques, a variety of moieties containing diamino and dicarboxylic groups with orthogonal protecting groups can be introduced for conjugation to PEG.

The present disclosure also provides for conjugation of the PYY peptides described herein to one or more polymers other than polyethylene glycol.

In some embodiments, the PYY peptides described herein are derivatized by conjugation or linkage to, or attachment of, polyamino acids (e.g., poly-his, poly-arg, poly-lys, etc.) and/or fatty acid chains of various lengths to the N- or C-terminus or amino acid residue side chains. In certain embodiments, the PYY peptides described herein are derivatized by the addition of polyamide chains, particularly polyamide chains of precise lengths, as described in U.S. Pat. No. 6,552,167, which is incorporated by reference in its entirety. In yet other embodiments, the peptides and polypeptides are modified by the addition of alkylPEG moieties as described in U.S. Pat. Nos. 5,359,030 and 5,681,811, which are incorporated by reference in their entireties.

In certain embodiments, the PYY peptides disclosed herein are derivatized by conjugation to polymers that include albumin and gelatin. See, Gombotz and Pettit, Bioconjugate Chem., 6:332-351, 1995, which is incorporated herein by reference in its entirety.

In further embodiments, the PYY peptides disclosed herein are conjugated or fused to immunoglobulins or immunoglobulin fragments, such as antibody Fc regions.

In various embodiments, the PYY peptides described herein are derivatized by attaching small molecule substituents, including short chain alkyls and constrained alkyls (e.g., branched, cyclic, fused, adamantyl groups), and aromatic groups.

In certain embodiments, the PYY peptides described herein comprise an alkylglycine amino acid analog comprising a C5-C9 straight or branched alkyl side chain, or a cycloalkyl group. In one embodiment, the PYY peptides comprises an alkylglycine comprising a C6-C8 straight or branched alkyl side chain. In another embodiment, a PYY peptide comprises an octylglycine comprising a C8 straight alkyl side chain (octyl-glycine).

The PYY peptides described herein may be prepared as salts with various inorganic and organic acids and bases. Such salts include salts prepared with organic and inorganic acids, for example, with HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, alkali earth salts, e.g. calcium and magnesium salts, and zinc salts. The salts may be formed by conventional means, such as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

In some embodiments, PYY peptides are treated or conditioned prior to use. For example, PYY peptides may be incubated with a delivery vehicle, such as lipoproteins, nanoparticles, liposomes, etc., prior to use.

In some embodiments, provided herein are pharmaceutical preparations comprising: (a) a PYY peptide described herein; (b) a physiologically acceptable buffer or carrier. In some embodiments, pharmaceutical preparations further comprise an additional therapeutic agent (e.g., antibiotic, antifungal, probiotic, etc.).

In some embodiments, provided herein are fusion peptides or polypeptides comprising: (a) a PYY peptide described herein, and (ii) a functional peptide or polypeptide segment. In some embodiments, the functional peptide or polypeptide segment comprises a signaling moiety, therapeutic moiety (e.g., antibiotic or antifungal small molecule), localization moiety (e.g., cellular import signal, nuclear localization signal, etc.), detectable moiety (e.g., fluorescent moiety, contrast agent), or isolation/purification moiety (e.g., streptavidin, $His_6$, etc.). Such fusions may be expressed from a recombinant DNA which encodes the PYY peptides and the additional peptide/polypeptide or may be formed by chemical synthesis. For instance, the fusion may comprise a PYY peptides and an enzyme of interest, a luciferase, RNasin or RNase, and/or a channel protein (e.g., ion channel protein), a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, selectable marker protein, nucleic acid binding protein, extracellular matrix protein, secreted protein, receptor ligand, serum protein, a protein with reactive cysteines, a transporter protein, a targeting sequence (e.g., a myristylation sequence), a mitochondrial localization sequence, or a nuclear localization sequence. The additional peptide/polypeptide may be fused to the N-terminus and/or the C-terminus of the PYY peptides. In one embodiment, the fusion protein comprises a first peptide/polypeptide at the N-terminus and another (different) peptide/polypeptide at the C-terminus of the PYY peptides. Optionally, the elements in the fusion are separated by a connector sequence, e.g., preferably one having at least 2 amino acid residues, such as one having 13 and up to 40 or 50 amino acid residues. In some embodiments, the presence of a connector sequence in a fusion protein of the invention does not substantially alter the function of either element (e.g., PYY peptides) in the fusion relative to the function of each individual element, likely due to the connector sequence providing flexibility (autonomy) for each element in the fusion. In certain embodiments, the connector sequence is a sequence recognized by an enzyme or is photocleavable. For example, the connector sequence may include a protease recognition site.

In some embodiments, provided herein are polynucleotides encoding a PYY peptide (or PYY peptide fusion) described herein. In some embodiments, provided herein are nucleic acid vectors (e.g., plasmid, bacmid, viral vector (e.g., AAV) comprising polynucleotides encoding a PYY peptide (or PYY peptide fusion) described herein. In some embodiments, vectors further comprise a promoter and/or one or more expression elements (e.g., transcription enhancer, translational start site, internal ribosome entry site, etc.). In some embodiments, methods are provided comprising administering a polynucleotide or vector described herein to a subject or sample (e.g., for the treatment or prevention of a fungal infection or disease related to fungal virulence, for the establishment and/or maintenance of healthy/normal microbiota, etc.

In some embodiments, provided herein are methods of treating a fungal infection or disease related to fungal virulence, comprising administering a PYY peptide described herein to a subject suffering from a fungal infection or disease related to fungal virulence.

In some embodiments, provided herein are methods of preventing a fungal infection, fungal virulence, fungal hyphae formation, or a disease related to fungal virulence, comprising administering a PYY peptide described herein to a subject. In some embodiments, the subject is at increased risk (e.g., relative to a general population) of developing a fungal infection, fungal virulence, fungal hyphae, or a disease related to fungal virulence. In some embodiments, the subject is elderly, a transplant recipient, infected with HIV, receiving or having recently received antibiotics, and infant, suffering from cancer or receiving treatment for cancer, etc.

In some embodiments, provided herein are methods of establishing healthy and/or normal microbiota in a subject, comprising administering a PYY peptide described herein to a subject having an environment of microenvironment (e.g., blood, gut, vagina, mouth, skin, etc.) that comprises abnormal (e.g., pathogenic, potentially pathogenic) microbiota (e.g., microbial imbalance (e.g., imbalance healthy microbes (e.g., *Lactobacillus*) to dimorphic or other polymorphic fungi), etc.). In some embodiments, the subject is elderly, a transplant recipient, infected with HIV, receiving or having recently received antibiotics, and infant, suffering from cancer or receiving treatment for cancer, etc.

In some embodiments, provided herein are methods of maintaining healthy and/or normal microbiota in a subject, comprising administering a PYY peptide described herein to a subject with healthy and/or normal microbiota.

That PYY has activity against virulent *Candida* species and is secreted into the lumen of the gut by Paneth cells has particular implications for the pathology of ileal Crohn's Disease (iCD). iCD is a subset of Inflammatory Bowel Disease (IBD) that is characterized by inflammation of the terminal ileum of the small intestine, transmural lesions, and chronic diarrhea, abdominal pain, and weight loss. Paneth cell dysfunction has been implicated in the pathogenesis of iCD, indeed, iCD is now believed to be a Paneth cell disease. Paneth cell abnormalities in humans are associated with the presence of risk alleles for iCD as identified through genome-wide association studies, and Paneth cell dysfunction correlates with more severe disease outcomes in iCD. iCD patients are also known to have elevated fungal burdens in their gut and the presence of serum antibodies directed against the fungal protein mannan, known as ASCA antibodies, is predictive of increased disease severity in these patients. Therefore, Paneth cell dysfunction in these patients would lead to reduced luminal PYY in the small intestine leading to outgrowth of virulent fungal species and initiation or potentiation of disease. Patients with genetic susceptibility leading to Paneth cell dysfunction are less able to weather environmental insults that may trigger hyphal growth of commensal fungal forms due to their impaired production of the specific antifungal peptide PYY.

Immunocompromised patients, including individuals with HIV/AIDS and those undergoing chemotherapy or organ transplant, have a risk of 6-30% of developing candidiasis while immunocompromised. However, current therapies for treatment of candidiasis are not well suited for prophylactic treatment due to their often harsh side effects and their untargeted mechanism of action that removes both virulent and commensal forms of fungi. A prophylactic anti-fungal PYY peptide that specifically targets virulent forms of fungi finds use in this population. In some embodiments, PYY peptides are formulated (e.g., for oral delivery) as a prophylactic therapy for such subjects.

In some embodiments, provided herein are pharmaceutical compositions comprising a PYY peptide and a pharmaceutically acceptable carrier. Any carrier which can supply an active agent is a suitable carrier, and such carriers are well known in the art. In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intrasternal injection, or infusion) (e.g., as sterile injectable aqueous or non-aqueous solutions or suspensions)), nasally (including administration to the nasal membranes, such as by inhalation spray), topically (such as in the form of a cream or ointment), transdermally (such as by transdermal patch), or rectally (such as in the form of suppositories), etc. In some embodiments, pharmaceutical compositions are delivered to the patient systemically or locally.

A pharmaceutical composition may be administered in the form which is formulated with a pharmaceutically acceptable carrier and optional excipients, adjuvants, etc. in accordance with good pharmaceutical practice. The pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form in order to achieve an easy and accurate administration of the active pharmaceutical peptide or polypeptide. In general, the therapeutically effective pharmaceutical agent (e.g., PYY peptide) is present in such a dosage form at a concentration level ranging from about 0.5% to about 99% by weight of the total composition, e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. The amount of the active ingredient (e.g., PYY peptide) that may be combined with such materials to produce a single dosage form will vary depending upon various factors, as indicated above. A variety of materials can be used as carriers, adjuvants and vehicles in the composition of the invention, as available in the pharmaceutical art.

In some embodiments, pharmaceutical compositions (e.g., comprising PYY peptides) are co-administered (concurrently or in series) with one or more additional therapeutic agents. Additional therapeutic agents may comprise other antimicrobials (e.g., antibiotics, antifungals, antiparasitic, antiviral, etc.). In some embodiments, co-administered agents are co-formulated. In other embodiments, the agents are separately formulated. Co-administration may occur concurrently or sequentially. For concurrent administration, the agents may be co-formulated or separately formulated. In some embodiments, the agents are administered by the same route or by separate routes of administration. For sequential administration, any suitable time lapse may occur between administrations, for example, 1 minute, 2 minutes, 5 minutes, 10 minutes, 30 minutes, 1 hour, 2 hours, 4 hours, 6 hours, 8 hours, 12 hours, 24 hours, 48 hours, 72 hours, 1 week, 2 weeks, 4 weeks, or more, or ranges there between.

In some embodiments, pharmaceutical compositions (e.g., comprising PYY peptides) are provided as part of a kit (e.g., comprising other therapeutic agents, packaging, container(s), instructions, devices for administration, etc.).

In some embodiments, pharmaceutical compositions and/or kits for administration/co-administration comprise a PYY peptide and one or more therapeutic agents.

In some embodiments, a PYY peptide is co-administered with one or more antibiotics. In some embodiments, such formulations/co-administrations are useful in the treatment/prevention of multiple types of pathogenic infection and/or for establishing/restoring/maintaining normal microbiota. In some embodiments, the antibiotic may inhibit cell wall synthesis, protein synthesis, nucleic acid synthesis, or alter cell membrane function. Classes of antibiotics that find use in conjunction with the other embodiments herein include, but are not limited to, macrolides (i.e., erythromycin), penicillins (i.e., nafcillin), cephalosporins (i.e., cefazolin), carbepenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate). Examples of specific antibiotics that can be used include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin.

In some embodiments, a PYY peptide is co-administered with one or more beneficial and/or probiotic bacteria. In some embodiments, such formulations/co-administrations are useful in the treatment/prevention of multiple types of pathogenic infection and/or for establishing/restoring/maintaining normal microbiota. In some embodiments, beneficial and/or probiotic bacteria that find use in the embodiments herein include, but are not limited to probiotic strains of *Lactobacillus, Saccharomyces, Enterococcus, Streptococcus, Pediococcus, Leuconostoc, Bacillus, Escherichia coli*, and *Bifidobacterium*. Any beneficial and/or probiotic bacteria may find use in embodiments herein.

In some embodiments, a PYY peptide is co-administered with one or more antiviral agents or treatment. In some embodiments, such formulations/co-administrations are useful in the treatment/prevention of multiple types of pathogenic infection and/or for establishing/restoring/maintaining normal microbiota. In some embodiments, PYY peptide are co-administered with a topical antifungal, such as clotrimazole, econazole, ketoconazole, miconazole, tioconazole, terbinafine, and amorolfine. Such agents may be administered as creams, shampoos, soaps, liquids, sprays, etc. and may be co-formulated with the PYY peptides or may be separately formulated. In some embodiments, PYY peptide are co-administered with an oral antifungal, such as miconazole, nystatin, terbinafine, itraconazole, fluconazole, posaconazole, and voriconazole. Such agents may be administered oral gels, liquids, pills, capsules, tablets, etc. and may be co-formulated with the PYY peptides or may be separately formulated. In some embodiments, PYY peptide are co-administered with an antifungal injection, such as amphotericin, flucytosine, itraconazole, voriconazole, anidulafungin, caspofungin, and micafungin.

Any suitable formulations or co-formulations (with a PYY peptide) of the aforementioned agents may find use in embodiments herein. In the case of separate formulation, the PYY peptides and the other agents may be administered by the same route or by separate routes of administration.

In some embodiments, the PYY peptides described herein find use in eliminating, reducing, and/or preventing fungal growth, fungal adhesion, and/or fungal biofilm formation on non-biological surfaces, instruments, devices, etc. In some embodiments, methods are provided in which a composition comprising PYY peptides, alone or with additional agents (e.g., antifungals, antibiotics, antiseptics, detergents, cleaners, soap, alcohol, etc.) is administered to the non-biological surfaces, instruments, devices, etc. Examples of non-biological surfaces, instruments, devices, etc. for treatment with the PYY peptides described herein include medical devices, surgical instruments, catheters, medical tubing, implants, stents, valves, etc. Suitable embodiments described herein for formulation of a pharmaceutical composition and/or administration to a subject will also apply to use in non-biological contexts, when applicable.

All publications and patents listed below and/or provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

EXPERIMENTAL

Example 1

Materials and Methods

Animals and *Candida* Challenge Models

All animal protocols were approved by IACUC at the University of Chicago. Animals were either wild-type (WT) or PYY" gene-deficient mice on the C57Bl/6 background bred and housed under standard 12:12 light/dark conditions at the University of Chicago. Germ-free animals were maintained in sterile isolators in our gnotobiotic facility. For studies using *Candida* spp, animals were maintained in single BSL2 cages and administered Clindamycin (PO gavage, 25 mg) and Cefoxitin (IM, 50 mg) 2 days before oral *Candida* challenge. 1 day prior to challenge, mice were fasted and administered Clindamycin (25 mg) and Cortisone Acetate (SQ). Mice were gavaged with 200 µL of 1.0 OD600 *Candida albicans* (sc3514) in the morning and provided food 4 hours later. Clindamycin (250 mg/kg BW) was administered on days 0, 2, 4, 6, and 8 until sacrifice. In studies examining oral peptide adminstraiton, peptides (200 ug) were suspended in sterile PBS (100 uL) and gavaged on days 2, 3, 4, and 8. Fecal pellets were collected on days-2, 0, 2, 4, 6, and 8, weighed, resuspended in sterile PBS and plated in duplicate on YPD plates containing Gentamycin (0.1 mg/mL) and Vancomycin (0.01 mg/mL), to prevent bacterial growth, at 30° C. Animals were humanely euthanized and regions of small and large bowel tissues were taken for cytokine analysis.

Immunofluorescence and Epitope Blockade

Mucosal tissues were fixed in 4% formalin/PBS overnight at 4° C. Five-micron sections were cut, deparaffinized, rehydrated, and washed in PBS. Antigen retrieval was performed by boiling in sodium citrate (pH 6.0) for 10 minutes and cooled to room temperature. Sections were blocked with protein block (DAKO) for 45 minutes followed by primary antibody (1:1000 rabbit anti-PYY, #ab22663, abcam) and (1:400 goat anti-lysozyme, #C-19, Santa Cruz) incubation overnight at 4° C. Samples were washed and Alexa Fluor conjugated secondary antibody (1:1000, 555 donkey anti-rabbit, Invitrogen life science; 1:1000, 647 donkey anti-goat, Invitrogen life science) was applied for 1 hour at room temperature. Slides were counterstained with DAPI and visualized with a Leica DM2500 microscope (Leica Microsystems, Wetzlar, Germany) through a 20× lens objective using Image Pro-Plus software (Media Cybernetics, Silver Springs, MD, USA) for image capture. To confirm epitope specificity, full-length recombinant immunizing peptide was added to the primary anti-PYY antibody prior to staining followed by the remaining protocol as stated.

Super Resolution Microscopy

For super resolution microscopy, 170 um cover slips were coated with poly-L-lysine overnight. Next, five-micron tissue sections were cut and placed on slides and allowed to dry. Deparaffinization, rehydration, antigen retrieval, blocking, and primary antibody steps were performed as described above but with higher primary antibody concentrations; 1:100 rabbit anti-PYY and 1:100 donkey anti-Lysozyme in antibody diluent (DAKO). Next, slides were washed five times (5 mins) in PBS. Samples were fixed in 4% paraformaldehyde for 20 minutes at room temperature and washed in PBS three times. Secondary antibody was added for 1 hour as above and washed three times in PBS. Slides were kept in PBS and mounted immediately before imaging on a Leica Super-Resolution System (SR GSD 3D) and analyzed with thunderstorm software (Ovesny et al. Bioinformatics 30:2389-2390, 2014.: incorporated by reference in its entirety). Specifically, crypt bases were imaged to visualize individual Paneth cells, containing Lysozyme, and villus L-cells were contained, containing no Lysozyme.

Laser Capture Microdissection

To investigate whether PYY mRNA expression was present in the Paneth cell compartment, laser capture microdissection (LCM) was performed. OCT frozen tissues were cut 8 μm thick and placed on frozen PEN slides from Leica (Cat. #11505158). Slides were processed rapidly, with 30 seconds in Carnoy's solution, 1 min in 70% ethanol, and 10 dips in ddH20. Sections were stained with alcian blue for 1 minute, dipped in ddH20, and placed in nuclear fast red for 30 seconds. Slides were dipped through graded ethanols; 70%, 90%, 95%, and 100% and dried. LCM was performed on a Leica DM 6000B microscope. Regions of villous epithelium or the crypt base, as visualized by the presence of Paneth cell granules, were isolated and collected into RNAlater labeled villous and crypt RNA fractions respectively.

Peptide Modeling

To predict the structure of peptides, including PYY, Magainin2, and skin PYY, a protein homology/analogy recognition engine was used (Kelley & Sternberg. Nat Protoc 4:363-371, 2009.: incorporated by reference in its entirety).

Recombinant Peptides

Figure 5:
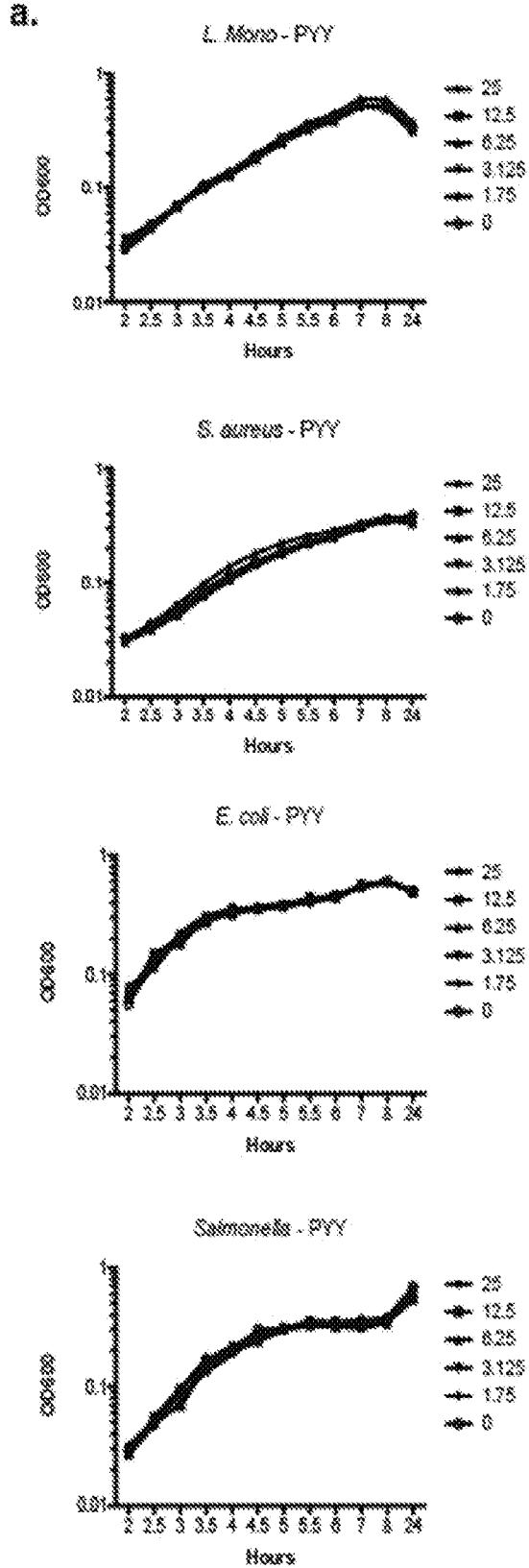
FIG. 5. Growth of L. mono, S. aureus, E. coli, and Salmonella in PYY (A) and $PYY_{13-36}$ (B) at concentrations of 1.75, 3, 6.25, 12.5, and 25 uM compared with control. Gram negative and positive species were chosen under anaerobic and aerobic growth conditions. No differences were found in any species tested.
Figure 5:
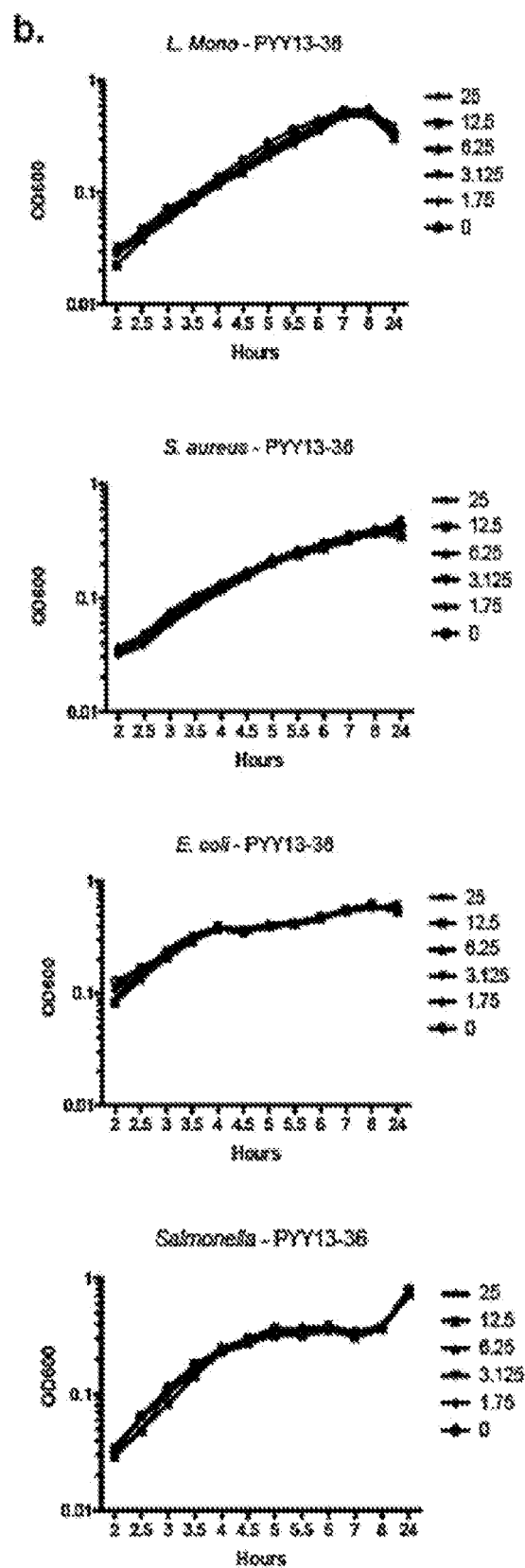

To study the effect of peptides upon *Candida* in vitro and in a murine model of chronic *Candida* challenge in vivo, peptides were obtained from GenScript (FIG. 5).

Ex Vivo Tissue Culture and ELISA

Tissues were harvested from conventional or germ-free WT mice. Three cm sections of distal ileum were dissected from the mesentery and ligated on one end. Next, Krebs buffer (pH 7.4) was inoculated with either LPS (100 ng/mL) or Carbamoylcholine (10 um) and sealed in the ileal section and incubated in Krebs at 37° C. for 30 minutes. Next, the luminal solutions were retrieved and centrifuged at 3000×g for 3 minutes to remove particulate. The resulting supernatant was diluted 1:25 and used in the PYY ELISA (EIA-PYY-1, RayBiotech), per manufacturer instructions.

Bacterial Growth Curves

Overnight cultures of *Listeria monocytogenes* EGD and *Staphylococcus aureus* Neuman, grown in BHI, with shaking (230 RPM) with at 37° C., and *Escherichia coli* (ETEC), and *Salmonella enterica* grown in LB, statically at 37° C. were passaged into 5 ml of fresh media (1/100) to prepare inocula for growth curves. PYY or PYY fragment, diluted in water, was serially diluted in appropriate medium in a 96 well plate, for a final concentration of 25, 12.5, 6.25, 3.75, and 1.76 uM. 100 ul of diluted inoculum was added to each well, in duplicate, and grown at 37° C. statically. OD600 was read using a VersaMax plate reader. Bacterial inocula were serially diluted into PBS and plated onto BHI or LB agar plates to determine CFU/well.

Fungal Cultures and In Vitro Assays

*Candida albicans* (sc3514 cited in: Romanowski et al. PLOS One 7: e30119, 2012.: incorporated by reference in its entirety) and *Candida tropicalis* (ATCC #13803) were maintained in frozen glycerol stocks at −80° C. and streaked out on yeast-peptone-dextrose (YPD) agar plates for 48 hours at 30° C. prior to use. Single colonies were selected and cultured in YPD media at 30° C. Biofilm assays were performed using crystal violet straining (Taff et al. Med Mycol 50:214-218, 2012.: incorporated by reference in its entirety) in the presence of 10-20 uM of respective peptides. To induce hyphal growth, strains were placed in YPD+5% FBS or RPMI media at 37° C. for 4 hours. To image hyphal membrane disruption, the DNA binding fluorescent dye, propidium iodide (PI), was added to wells strains in the presence of peptides and imaged under bright field and far red fluorescent conditions. To confirm the localization of PYY to the hyphal tip, fluorescently (N terminus FITC) labeled PYY was added during PI assays and imaged under 488 excitation-emission. To investigate PYY effects upon non-*Candida* species that forms hyphae using the PI assay, *Aspergillus flavus* was obtained from the University of Chicago Hospital Pathogen Laboratory, and grown in RPMI at 37 C overnight followed by treatment with PI and various concentrations of peptide. To investigate *Candida albican* virulence gene expression, 10 μL of a 1.0 OD600 culture were placed in 1 mL RPMI at 37° C. with shaking for 8 hours. Cultures were centrifuged at 3000×g for 5 minutes and RNA isolation was performed as described below.

Mouse and Yeast RNA Isolation and Quantitative PCR

Murine RNA was isolated with the Trizol (Ambion) and chloroform method. Yeast RNA was isolated with the RiboPure RNA Yeast kit (AM1924, Invitrogen Life Science), which includes DNAase treatment steps, according to manufacturer protocol. RNA concentration and quality was determined by UV spectrophotometry. RNA was reverse transcribed using anchored-oligo (dT) and random hexamer primers. Following RT (Transcriptor Reverse Transcriptase Reaction buffer 5×; Protector RNase Inhibitor 40U/ul; Deoxynucleotide Mix, 10 mM; Transcriptor Reverse Transcriptase 20U/ul), RT-PCR was performed on resulting cDNA in triplicate, using the manufacturer's protocol (Roche Applied Science), in LightCycleR capillary. The optimal concentration of cDNA and primers, as well as the maximum efficiency of amplification, were obtained through five-point, two-fold dilution curve analysis for each gene. RT-PCR amplification consisted of an initial denaturation step (95° C. for 10 min), 45 cycles of denaturation (95° C. for 10s), annealing (55° C. for 20s) and extension (60° C. for 30s), followed by a final incubation at 55° C. for 30s and cooling at 40° C. for 30s. All measurements were normalized by the expression of GAPDH gene, considered as a stable housekeeping gene. Gene expression was determined using the delta-delta Ct method: $2^{-\Delta\Delta CT}$ ($\Delta\Delta CT$=[Ct (target gene)-Ct (GAPDH)]$_{patient}$−[Ct (target gene)−Ct (GAPDH)]$_{control}$). Real-time data were analyzed using the Roche LightCycleR (Roche Applied Science).

Results

Mouse and Human Paneth Cells Produce PYY Peptide

In experiments conducted during development of embodiments herein investigating peptide production in the small intestine, immunofluorescence was performed for PYY in sections of the murine small intestine. A gradient of PYY immunostaining in enteroendocrine L-cells was observed throughout the small intestinal mucosa, which was particularly prominent in the distal ileum (FIG. 1a). However, PYY immunostaining was also observed in Paneth cells, which were identified histologically and by immunofluorescence for the antimicrobial peptide, lysozyme (Ref. 9; incorporated by reference in its entirety) (FIG. 1a). The addition of the recombinant PYY peptide to the primary antibody prior to staining blocked all subsequent Paneth cell and L-cell specific staining, but not other non-specific background (FIG. 1b), supporting epitope specific recognition of PYY in Paneth cells. In order to determine whether human Paneth cells produced PYY, healthy human ileal biopsies were obtained. Sectioning and immunofluorescence staining of these biopsies also demonstrated PYY specificity to lysozyme and sPLA$_2$ containing Paneth cells.

As PYY had only been known to be expressed by villus L-cells in the small intestine, laser capture micro-dissection was used to isolate Paneth cells from the crypt base of the distal ileum (FIG. 1d). Total RNA was extracted for qRT-PCR to determine gene expression levels of PYY and other genes encoding Paneth cell, goblet cell, brush border, or enteroendocrine specific transcripts (FIG. 1e). These findings were consistent with the immunofluorescence images, showing robust PYY transcript levels in a crypt base preparation that was highly enriched in Paneth cell markers in contrast to villus cell markers which were minimally represented. Finally, stimulated emission depletion (STED) microscopy was performed on ileal mucosa to obtain high resolution immunolocalization to determine whether PYY was packaged into secretory granules of Paneth cells. As shown in FIG. 1f, PYY was localized to intracellular small dense core secretory granules that were distinct from those containing lysozyme, indicating separate compartmentalization and possibly regulation.

A hallmark of Paneth cell biology is the vectoral secretion of secretory contents into the luminal compartment, which can be stimulated by exposure to microbial products, such as LPS or cholinergic stimulation such as carbamylcholine. Upon luminal stimulation with these agents, increased luminal secretion of PYY was observed in ex vivo intestinal loops, as determined by ELISA (FIG. 1f). Ileal loops from germ free mice only produced PYY in response to cholinergic stimuli (FIG. 1f).

PYY is an Anti-Fungal Peptide with Very Specific Targeting Properties

Figure 2:
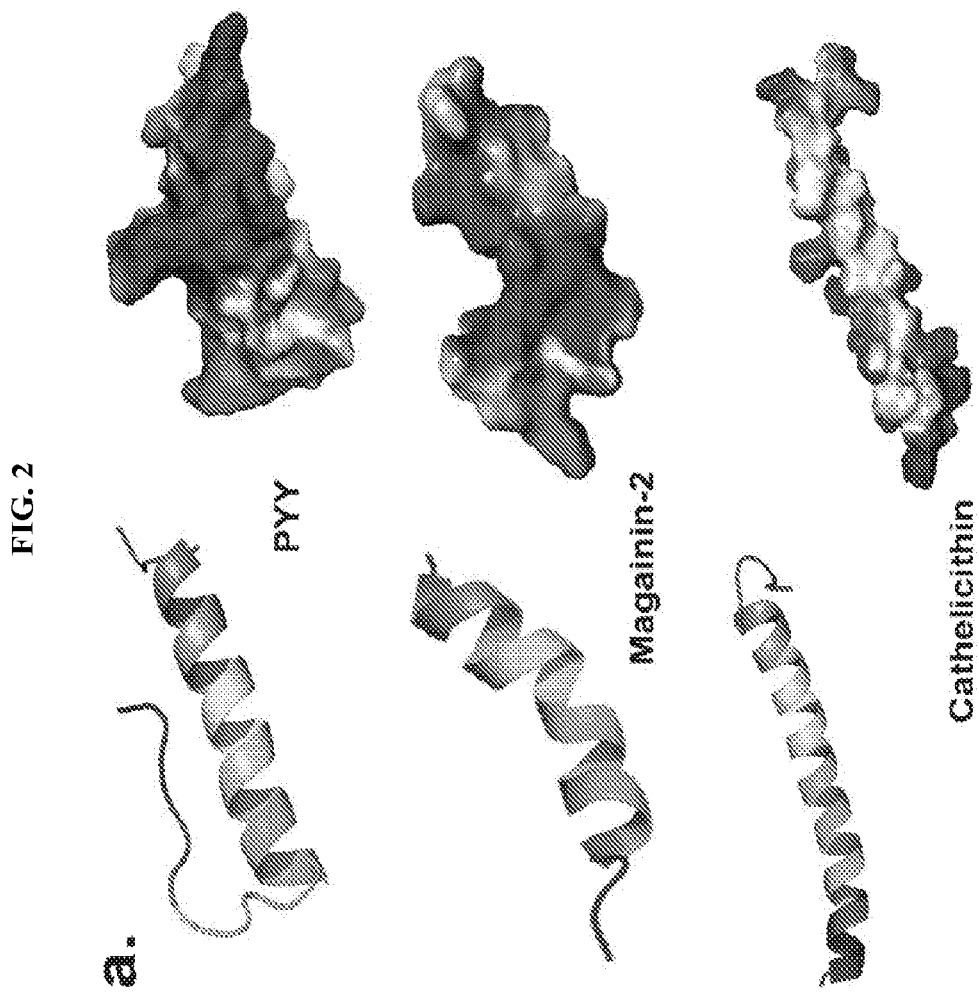
FIG. 2. (A) Peptide structure (left) and electrostatic surface (right) of PYY, Magainin-2, and Cathelicithin. PYY shares structural and charge characteristics with Magainin-2. (B) Helix projection of PYY (left) and Magainin-2 (right) alpha helix regions shows similarities in hydrophobic vs hydrophilic surface localization and total charges. (C) PYY and the alpha helix $PYY_{13-36}$ had no observable bactericidal effects in growth assays. (B) Under hyphal inducing conditions, Magainin-2, PYY and $PYY_{13-36}$ inhibited culture growth compared with $PYY_{1-12}$ or scrambled peptide. (E) Change in representative 24-hour growth cultures shown compared with scrambled peptide control.
Figure 2:
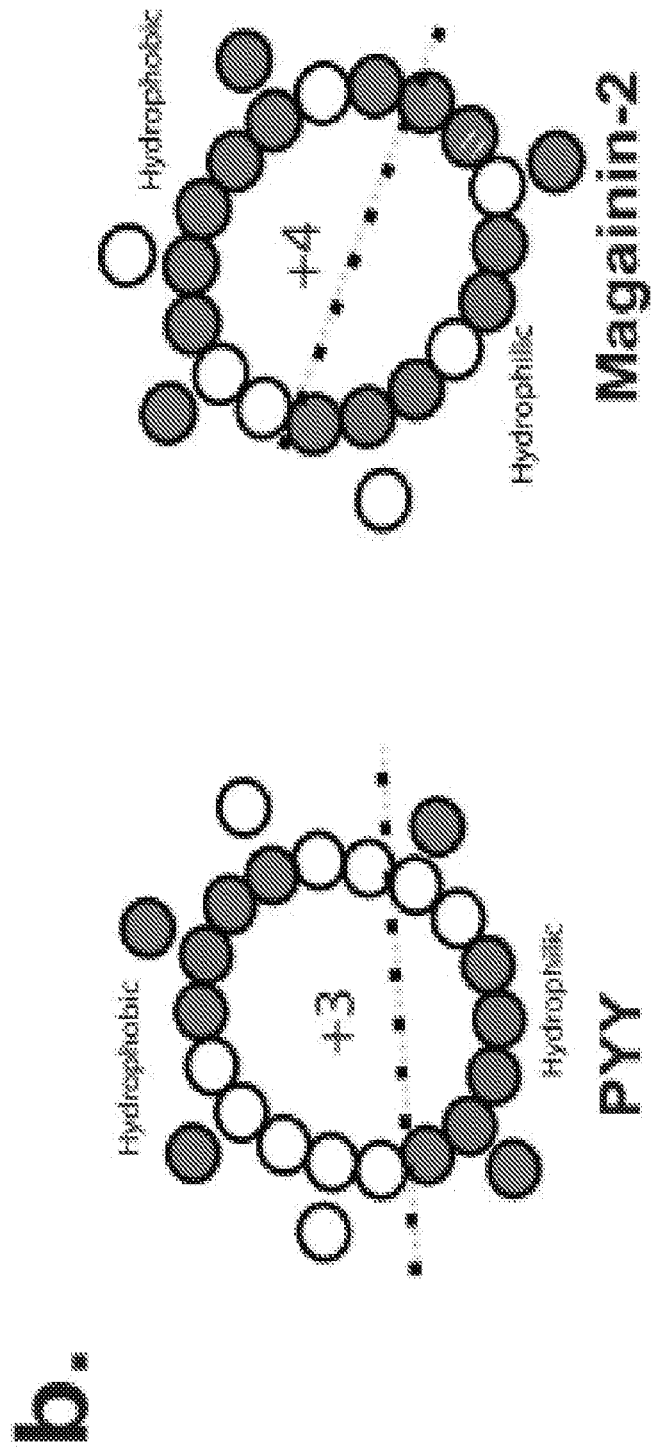
Figure 2:
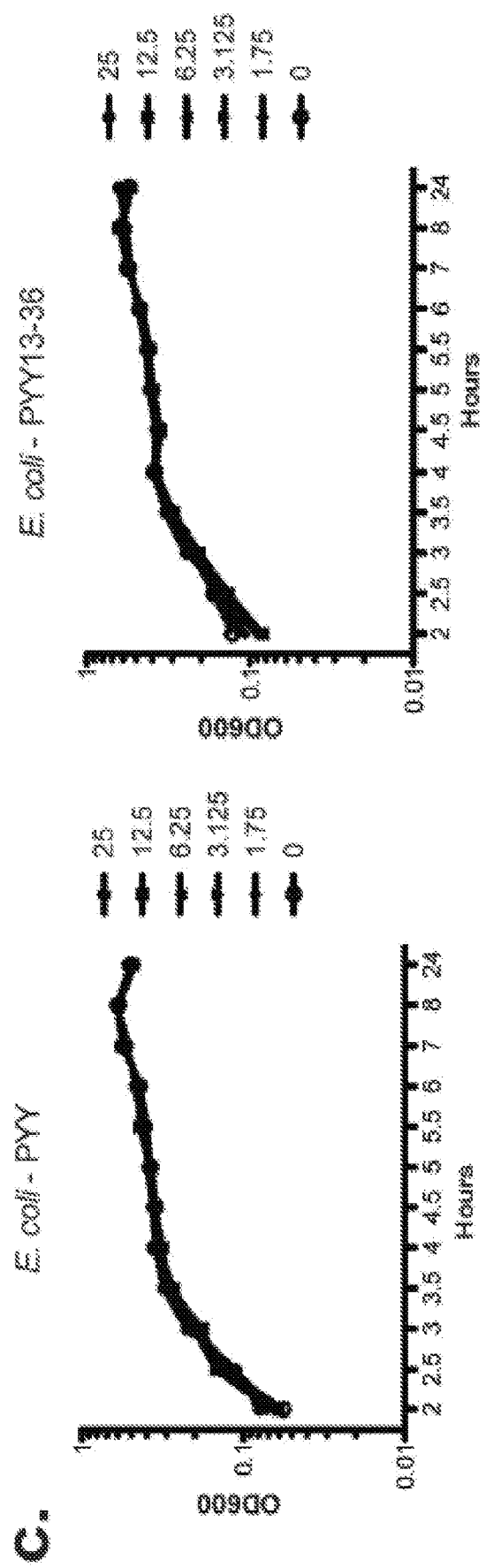
Figure 2:
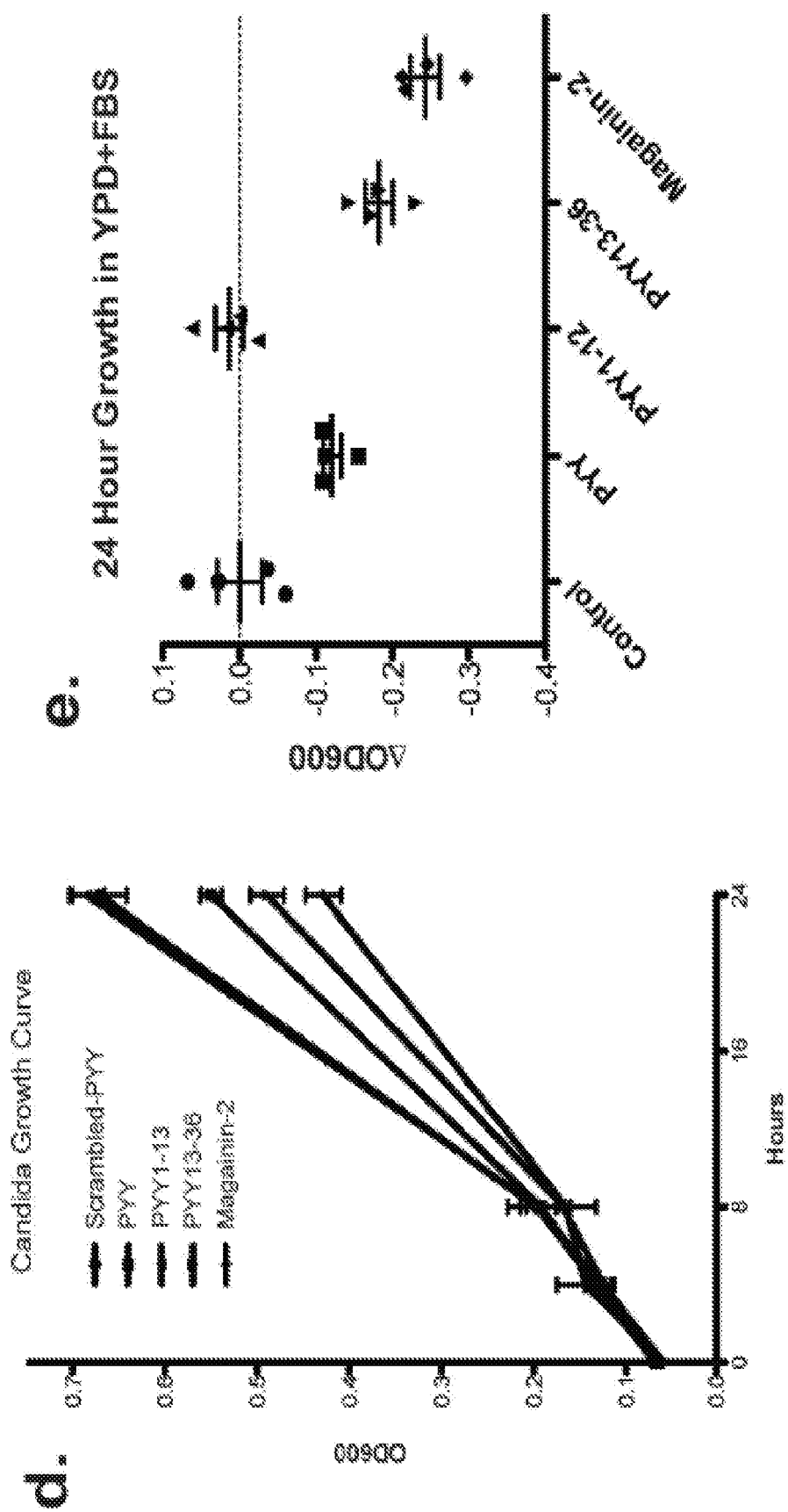

Paneth cells produce many types of AMPs to combat pathogenic microbes and control the commensal gut flora. Finding PYY in discrete secretory granules of Paneth cells and stimulated secretion into the luminal compartment raised the possibility that PYY has additional functions beyond those mediated through enteroendocrine L-cells and involved in regulation of satiety and metabolism. The predicted structure of PYY has an α-helical structure and charge distribution similar to many antimicrobial peptides, including mammalian cathelicidin found in innate immune cells (FIG. 2a). As many AMPs have a broad activity against bacterial species, in vitro bacterial growth assays were performed with the addition of PYY to the growth medium. Surprisingly, PYY did not inhibit the growth of *Escherichia coli* when added at a range of concentrations (FIG. 2c). When tested further with a variety of Gram-positive and Gram-negative bacteria, PYY had no effects on their proliferation (FIG. 5).

Experiments conducted during development of embodiments herein to reexamine the predicted structure of PYY and revealed that it also closely matched that of magainan-2 (FIG. 2a,b), an amphibian peptide reported as having potent antifungal as well as antibacterial properties. To determine its potential anti-fungal properties, PYY peptide was added to the growth medium of *Candida albicans*, a common member of human gut microbiota that is detectable in the gastrointestinal tract of many healthy adults. As shown in FIGS. 2d, e, PYY significantly decreased fungal growth. Two PYY peptides were generated, one composed of amino acids 1-13 ($PYY_{1-13}$) and one composed of amino acids 13-36 ($PYY_{13-36}$). It was found that $PYY_{1-13}$ displayed no antifungal properties, whereas $PYY_{13-36}$ was sufficient to inhibit growth of *C. albicans* (FIG. 2d,e).

PYY Specifically Targets the Terminal Hyphal Cells of the Virulent Form of *C. albicans*

Figure 3:
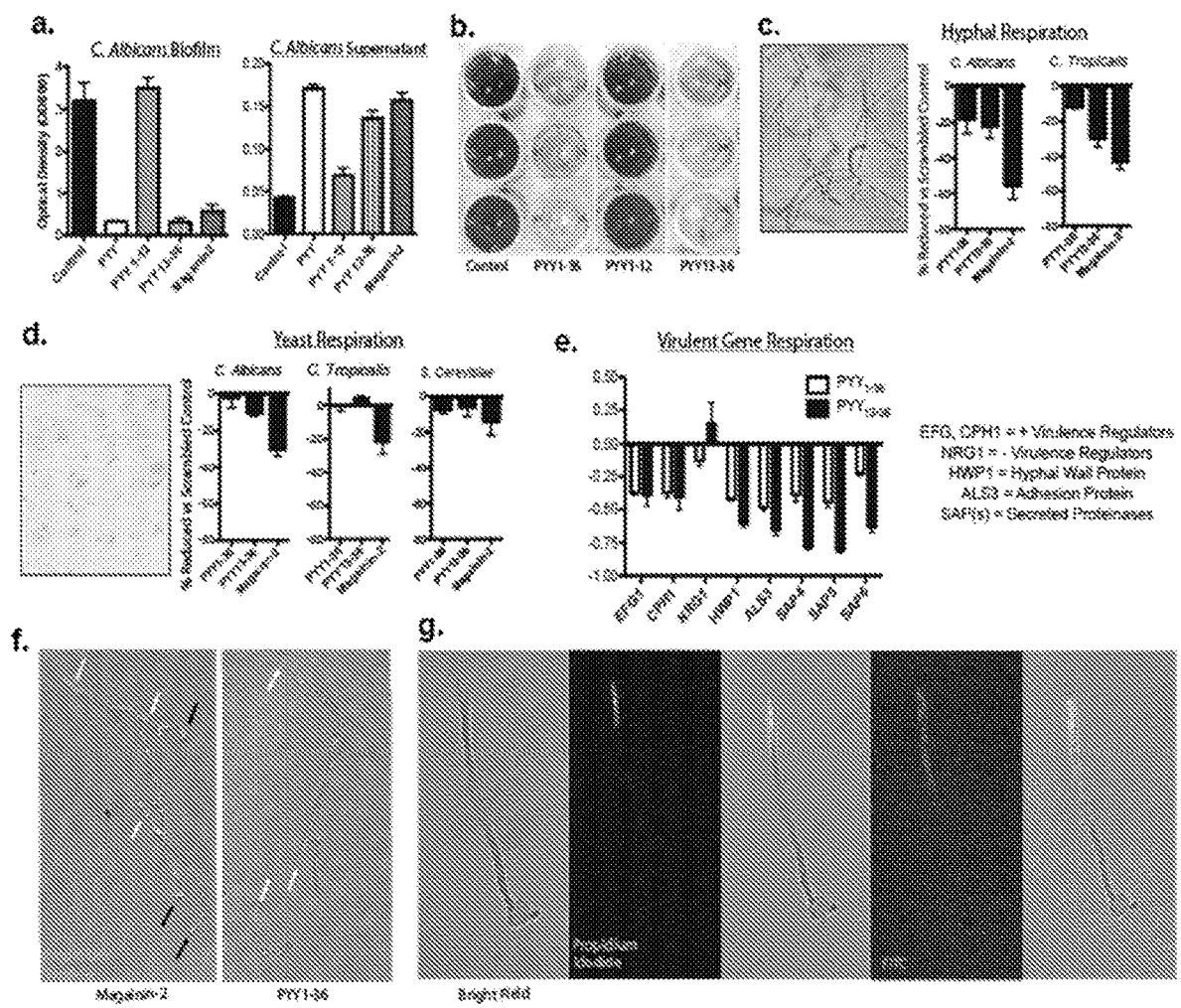
FIG. 3. (A) Representative results of Candida albicans (SC3514) biofilm growth and resulting supernatant suspension following respective peptide treatments. This assay was repeated with similar results in multiple strains of C. albicans and C. tropicalis. Results Demonstrate PYY, $PYY_{13-36}$, and Magainin-2 inhibit biofilm formation compared with control peptide or $PYY_{1-12}$. (B) Representative staining of C. albicans biolfilm with crystal violet. (C) Treatment of hyphal forms of C. albicans or tropicalis with PYY, $PYY_{13-36}$, or Magainin-2 suppressed respiration compared with peptide controls. (D) Treatment of yeast forms of C. albicans or tropicalis were largely unaffected by PYY or $PYY_{13-36}$, while Magainin-2 suppressed activity. The obligate yeast, Saccharomyces cerevisae, was equally susceptible to peptide treatment. (E) Treatment of the hyphal form of Candida albicans with PYY or $PYY_{13-36}$ demonstrates down regulation of many virulent genes compared with scrambled peptide controls. (F) In contrast to the pan permeability observed with Magainin-2 (12 uM), visualized with propidium iodide, PYY (12 uM) compromised only permeability at hyphal tips in Candida albicans. (G) Labeling of the PYY peptide with FITC at the N terminus demonstrated hyphal permeability was associated with labeled peptide accumulation.
Figure 6:
FIG. 6. Modification of PYY charge by replacing Arginine with Alanine. (A) No major structural differences were observed between PYY and PYY modified (PYY Mod) with alanine replacement. (B) Peptide sequences with alanine replacements. $PYY_{1-36}$ (SEQ ID NO: 1), PYY 1-36 Modified (SEQ ID NO: 47), $PYY_{1-13}$ (SEQ ID NO: 48), $PYY_{14-36}$ (SEQ ID NO: 2), and PYY$_{14-36}$ Modified (SEQ ID NO: 49). (C) Representative changes in biofilm formation with native and modified peptides. Modification of charge at arginine residues reduced the inhibitory effect of PYY and PYY$_{13-36}$ upon biofilm inhibition, suggesting the importance of charge interactions in mediating the anti-biofilm activity.
Figure 6:
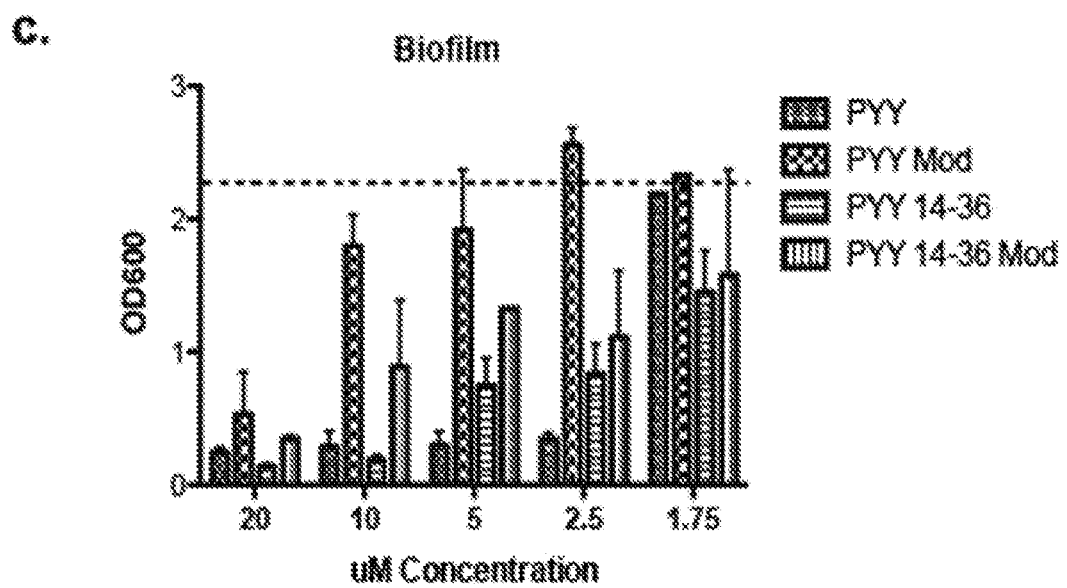

Although PYY inhibited the growth of *C. albicans* in broth culture containing serum (FIG. 2d,e), it had no effects on *C. albicans* growth in serum-free media. Addition of serum to the growth media of *C. albicans* induces growth of the virulent hyphal form, whereas *C. albicans* in serum-free growth media grows in a non-virulent yeast form. Experiments were conducted during development of embodiments herein to examined whether PYY might be specifically targeting the virulent form of *C. albicans*. Hyphal growth of *C. albicans* is necessary for the formation of biofilms. It was determined whether PYY was capable of inhibiting biofilm formation through a crystal violet biofilm staining assay. PYY and $PYY_{13-36}$, but not a scrambled peptide control or $PYY_{1-12}$, were capable of blocking biofilm formation by *C. albicans* (FIG. 3a,b). The ability of PYY to inhibit biofilm formation is dependent on its charged state, as mutation of the positively charged amino acid arginine to the neutral amino acid alanine abrogated the ability of PYY to block *C. albicans* biofilm formation (FIG. 6).

Figure 7:
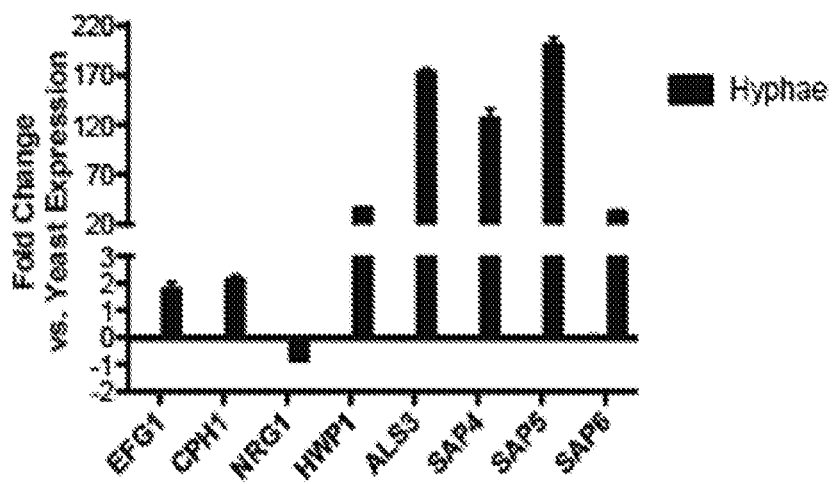
FIG. 7. (A) Induction of virulence genes found in hyphae vs. yeast controls for Candida albicans (strain SC3514). (B) Virulence gene expression in Hyphae treated with PYY, PYY$_{13-36}$, or Magainin-2, demonstrating that, compared with controls, PYY and PYY$_{13-36}$ down regulate virulence, while the amphibian peptide that is not native the mammalian intestine, Magainin-2, induced expression of several virulence genes.
Figure 7:
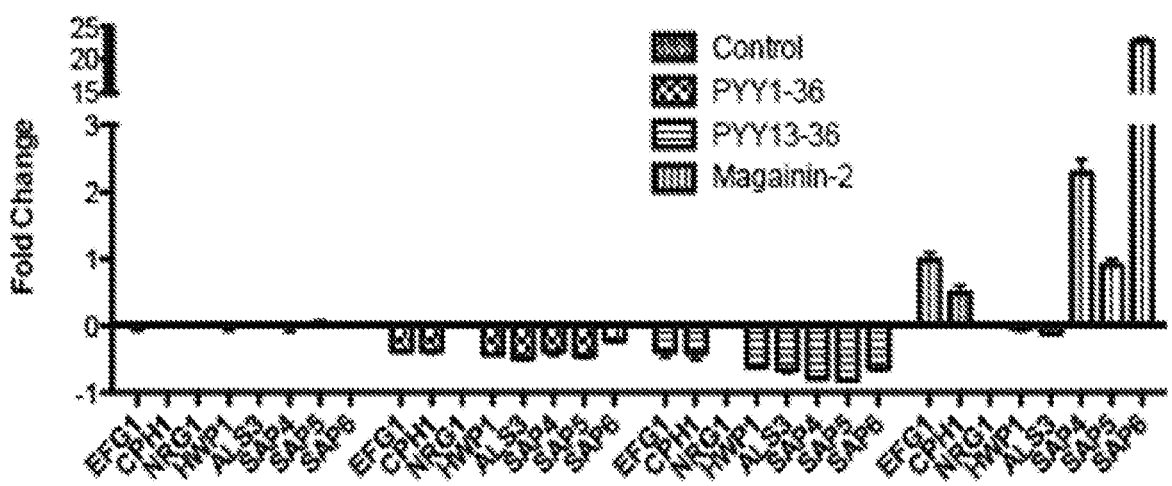

Experiments conducted during development of embodiments herein to directly test the effect of PYY on the viability of *C. albicans* by measuring respiration. It was found that PYY and $PYY_{13-36}$ inhibited respiration of *C. albicans* grown in the hyphal form, but not grown in the yeast form (FIG. 3c,d). This effect was not specific to *C. albicans* as respiration of the *Candida* species ('. *tropicalis* was also inhibited by PYY and $PYY_{13-36}$ during hyphal growth (FIG. 3c,d). Moreover, PYY had no effect on the non-hyphae forming, aerobic fungus *Aspergillus fumigatus*. Experiments conducted during development of embodiments herein to determine PYY's effects on *C. albicans* virulence genes, by growing in RPMI media at 37° C., which are unregulated upon sensing of certain environmental cues and contribute to pathogenesis resulting from *C. albicans* infections. Transcript levels were examined by qRT-PCR of the genes in *C. albicans* grown in vitro in the presence or absence of PYY and $PYY_{13-36}$. It was found that both peptides resulted in the downregulation of these virulence genes (FIG. 3e, FIG. 7).

Figure 8:
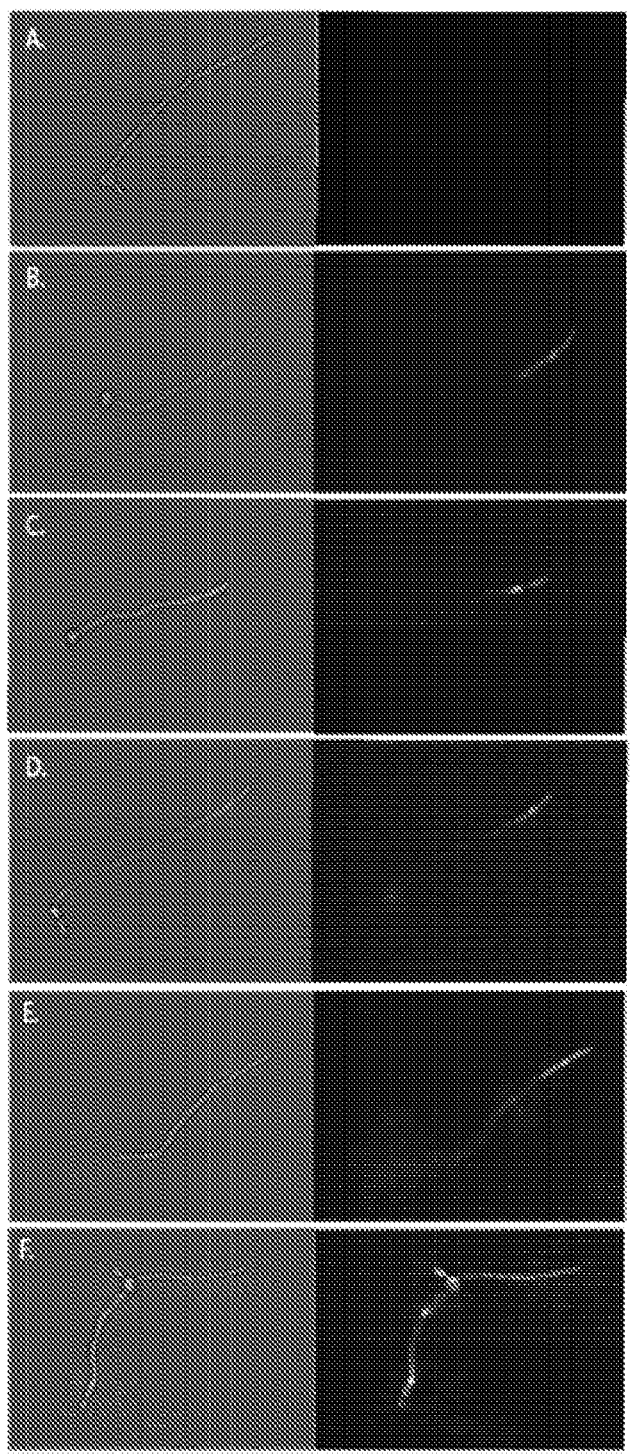
FIG. 8. Dose response of PYY$_{13-36}$ upon Candida albicans hyphal permeability at (A) 1.75, (B) 3, (C) 6.25, (D) 12.5, (E) 25 and (F) 50 uM, within 5 minutes of exposure, where =/>3 uM was sufficient for visual impairment at this time point.
Figure 9:
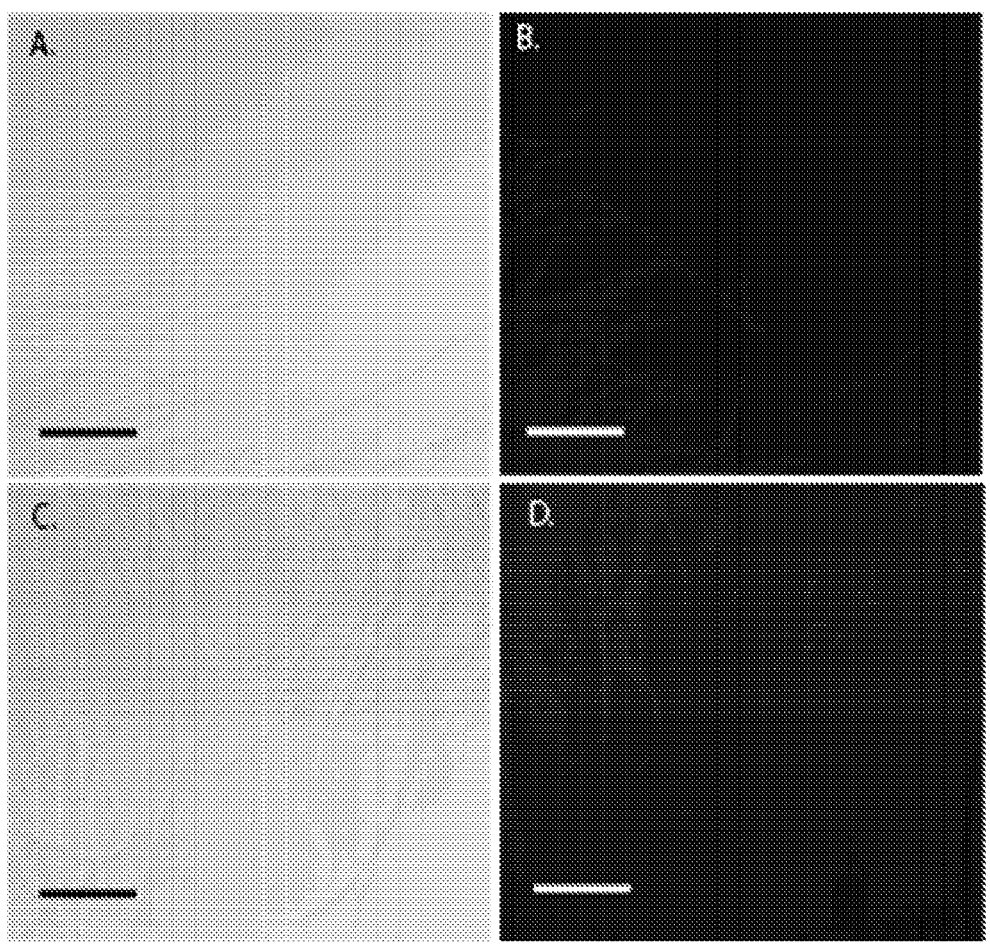
FIG. 9. The respiratory fungal pathogen, Aspergillus, showed no permeability susceptibility to PYY (A, B) or Magainin-2 (C, D) at 50 uM concentrations.
Figure 10:
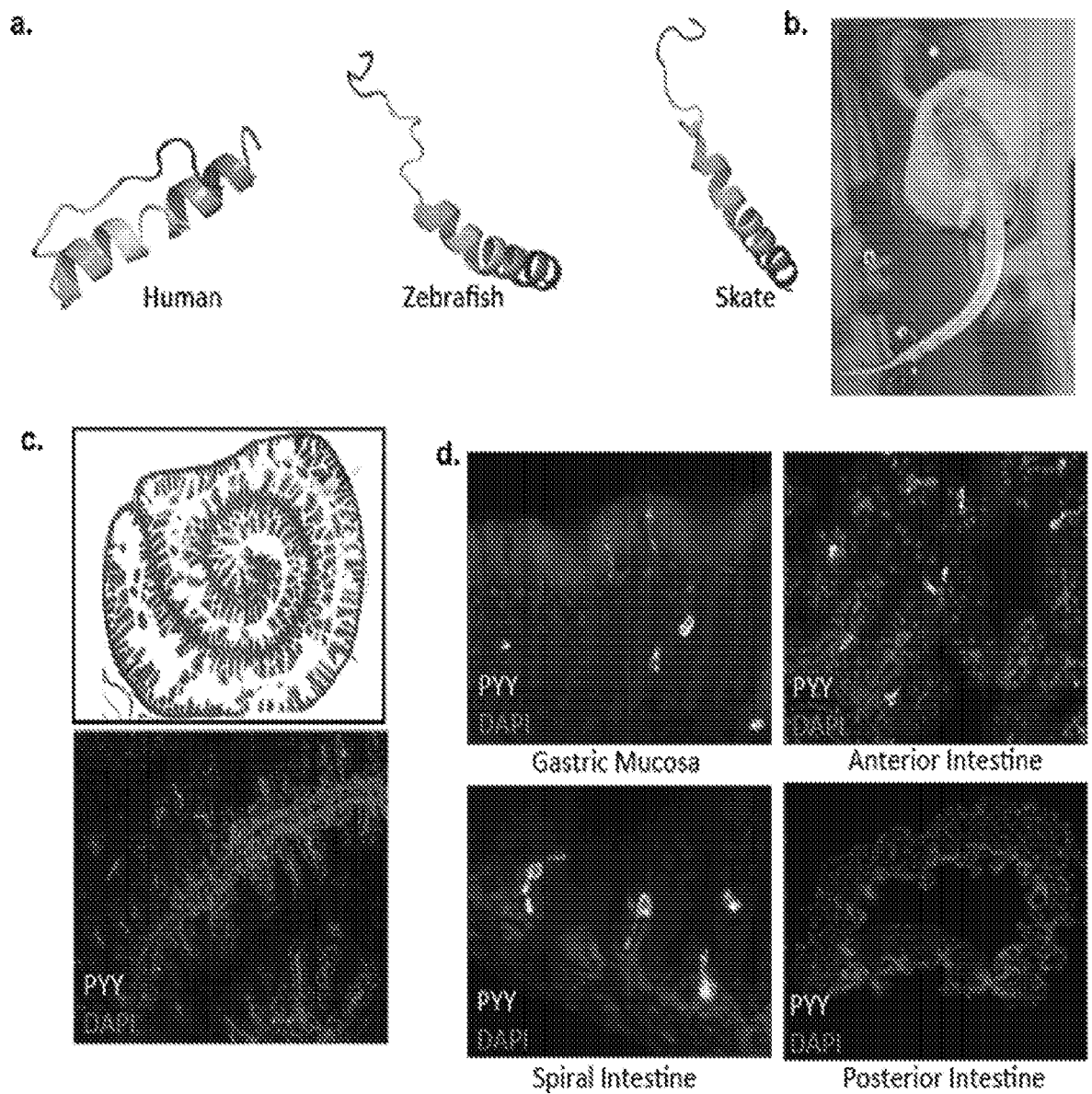
FIG. 10. Conservation of peptide sequence of structure across vertebrate evolution. (A) Peptide structure of PYY in humans, zebrafish, and skates. (B) The Little Skate, Leucoraja erinacea. (C) Histology of small intestine from L. erinacea with H&E (top) and PYY immunofluorescence (bottom). (D) PYY positive cells are found throughout the gastrointestinal tract of L. erinacea, including the stomach, anterior intestine, spiral intestine, but are devoid in the posterior intestine.
Figure 11:
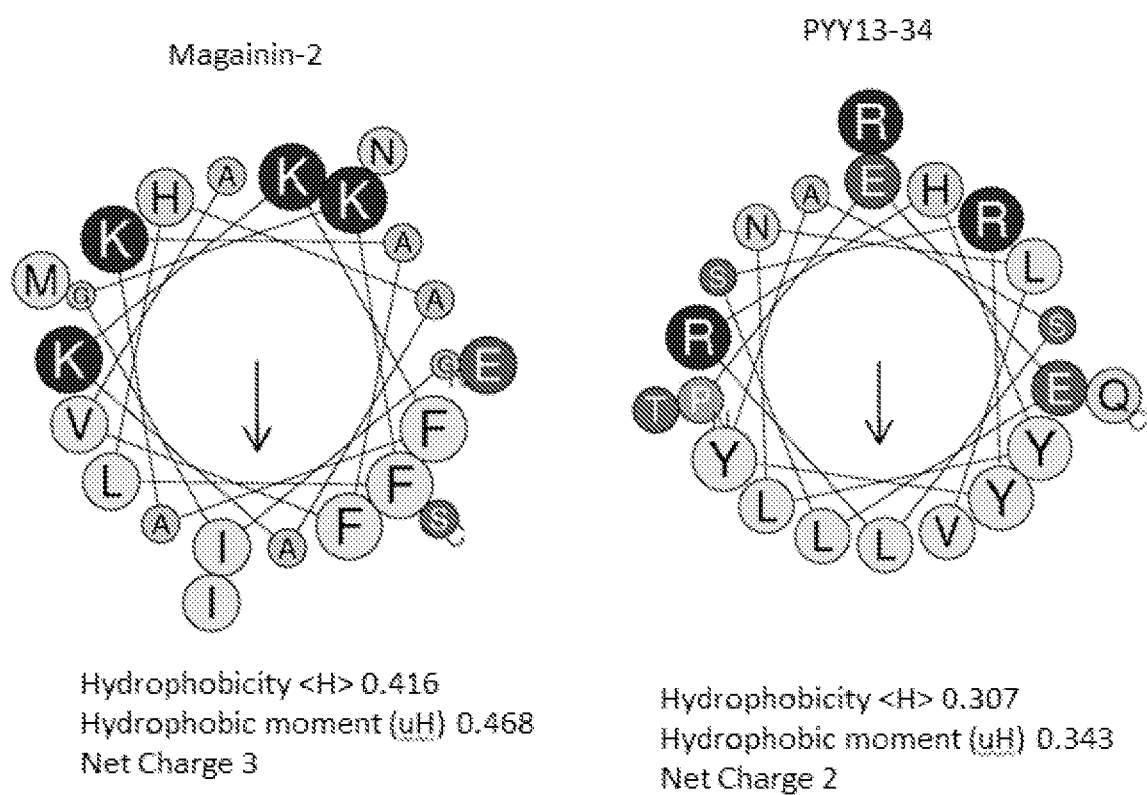
FIG. 11. Helical wheel representation of Magainin 2 (left) and PYY$_{13-34}$ (generated using HeliQuest; Gautier et al. Bioinformatics. 2008 Sep. 15; 24 (18): 2101-2.; herein incorporated by reference in its entirety).

Magainin-2 compromises fungal growth by inserting into and permeabilizing the fungal cell wall. To determine whether PYY functioned in the same way, *C. albicans* grown in a hyphal state were treated with magainin-2 or PYY. Permeabilization of the fungal cell wall was determined by uptake of propidium iodide (PI), a dye that is excluded by intact viable cells. With magainin-2 treatment, PI uptake indicative of cell wall permeabilization was observed along the entire length of the hyphae (FIG. 3f, panel 1). In contrast, PYY treatment specifically targeted terminal hyphal cells (FIG. 3f, panel 2), permeabilizing them in dose-dependent manner (FIG. 8). More proximal cells of the hyphae and the yeast body remained intact. Utilizing a FITC-labeled PYY, it was also observed that PYY localized exclusively to the same terminal hyphal cells that take up PI (FIG. 3g). These data thus indicated a different and selective action of PYY where only the terminal cells of virulent *C. albicans* hyphae are targeted, an action that is associated with impaired biofilm formation, down regulation of virulence genes, and cell death. The terminal hyphal cells of *C. albicans* differ from those more proximal, because they are metabolically more active, functionally diverse (attachment and biofilm formation), and have a different cell wall composition.

PYY Inhibits *C. albicans* Virulence and Colonization In Vivo

Figure 4:
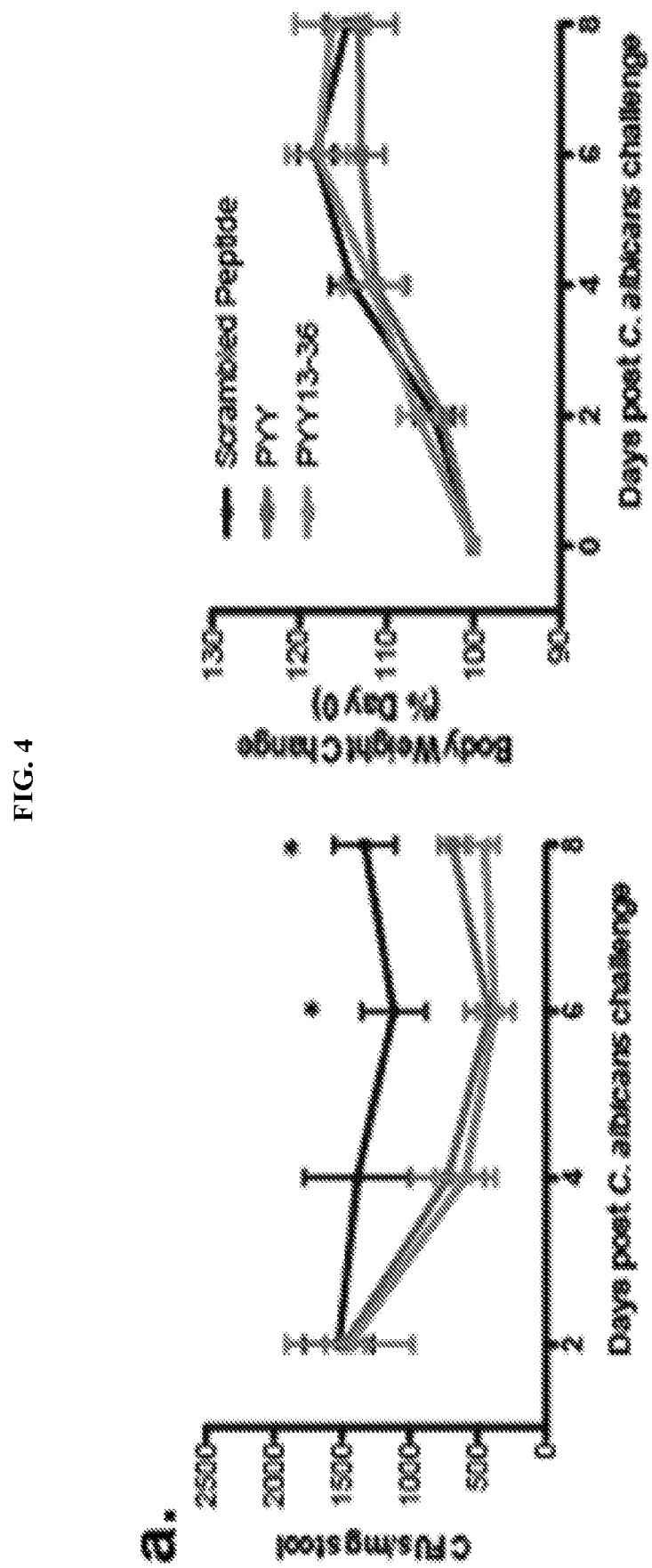
FIG. 4. In vivo testing of exogenous PYY administration or endogenous expression upon gastrointestinal colonization by Candida albicans in a chronic antibiotic susceptibility model. (A) Total fecal Candida albicans colony forming units (CFUs/mg stool) in wild-type mice administered 200 ug scrambled peptide, PYY, or $PYY_{13-36}$ during chronic colonization. Body weights were unchanged between treatment groups. (B) Total fecal Candida albicans CFUs in PYY deficient and wild type animals during chronic colonization. Body weights were unchanged between groups. Fecal output was unchanged between genotypes, eliminating transit time as a driver of differences in intestinal colonization.
Figure 4:
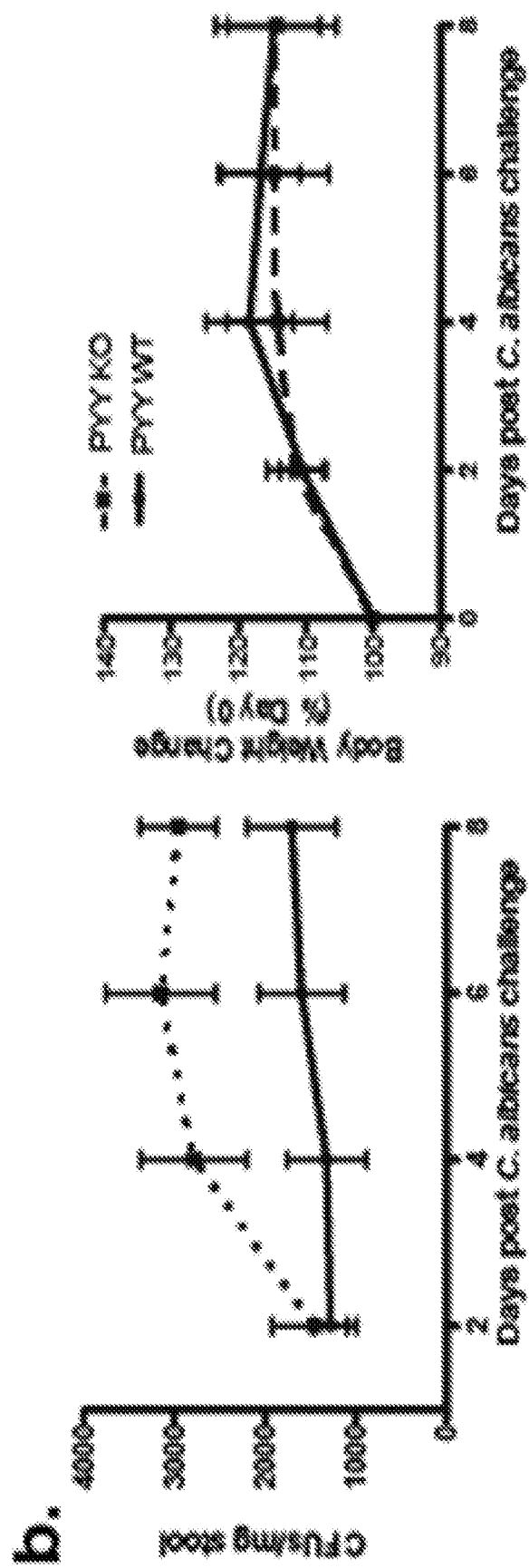
Figure 4:
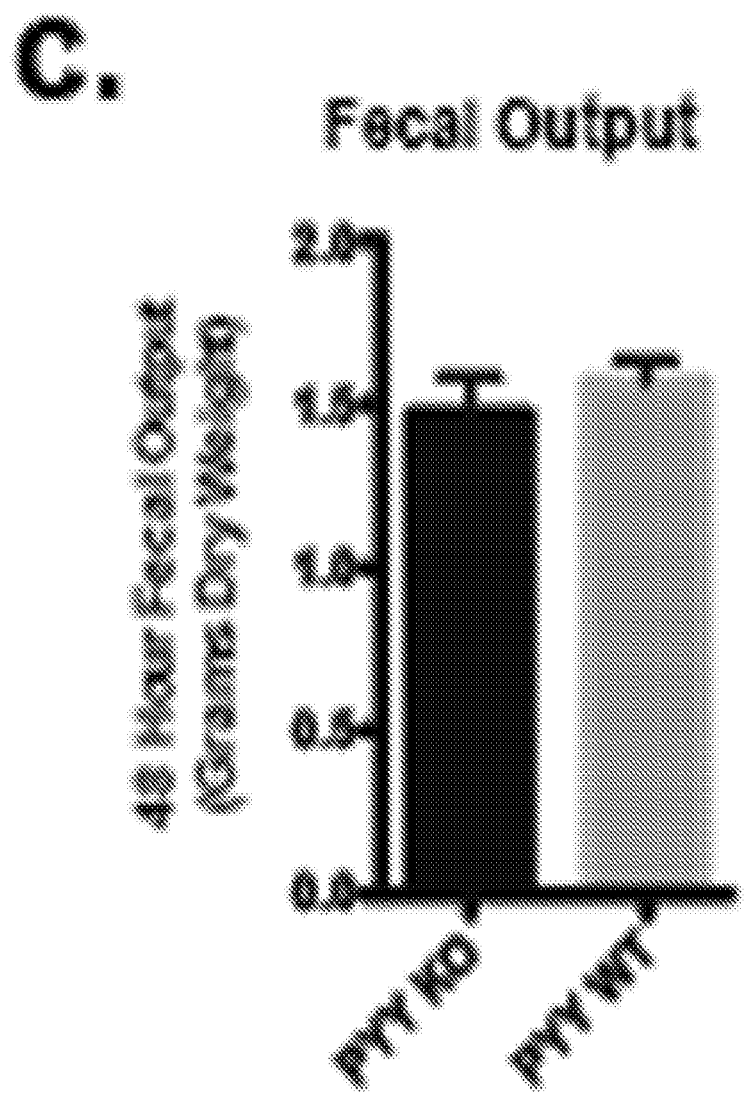

Experiments were conducted during development of embodiments herein to determine whether PYY given orally impacts fungal populations in vivo by utilizing a mouse model of chronic intestinal *C. albicans* colonization. It was found that oral administration of PYY or $PYY_{13-36}$ to these mice significantly reduced *C. albicans* fungal load in their fecal pellets without changing their body weight (FIG. 4a). Additionally, utilizing this same model of chronic intestinal *C. albicans* colonization in PYY-deficient mice (PYY-KO), much higher burden of *C. albicans* was observed compared to their wild-type counterparts (FIG. 4b). Total fecal output were not changed between PYY-KO and wild type mice, indicating that the differences in *C. albicans* colonization between the study groups are not likely a result of altered intestinal transit (FIG. 4c). Together, these data indicate that PYY inhibits *C. albicans* colonization in vivo, serving as a mechanism of fungal control in the intestinal microbiota.

Example 2

Figure 12:
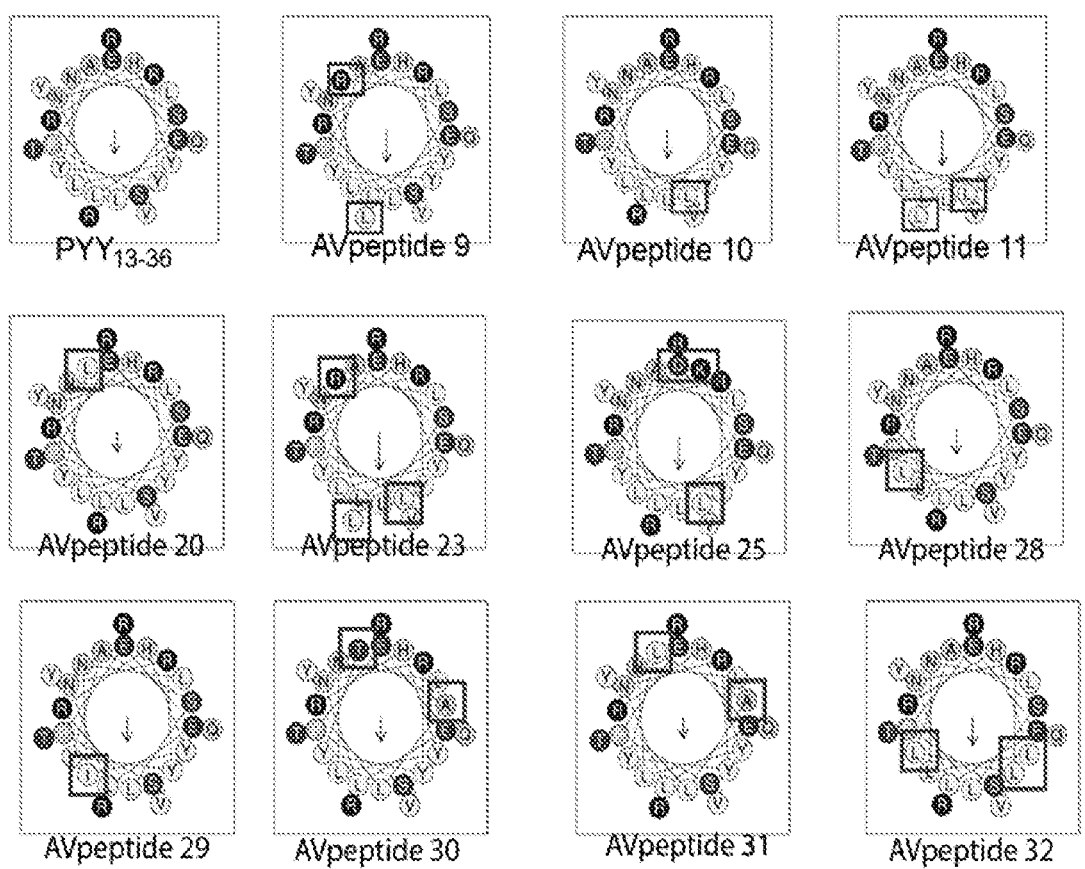
FIG. 12. Helical wheel diagrams of native PYY$_{13-36}$ and modified sequences with enhanced antifungal activity. Boxes indicate altered amino acid residues, arrows represent direction and magnitude of hydrophobic moment (generated using HeliQuest).
Figure 13:
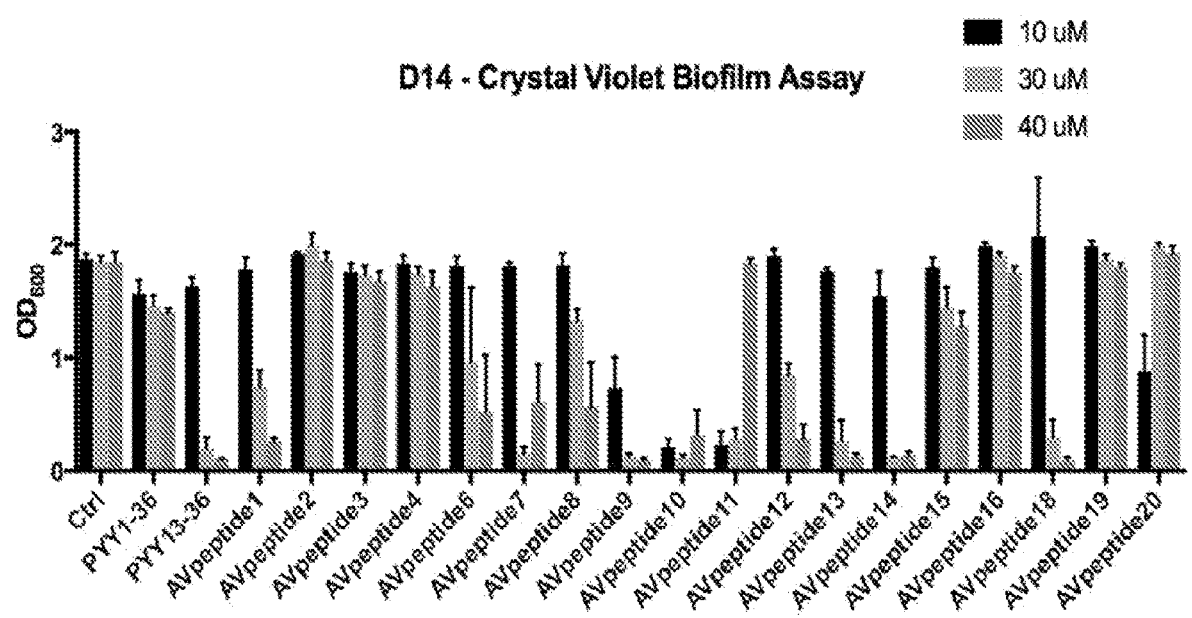
FIG. 13. Effect of AVpeptides in inhibiting biofilm formation by C. albicans strain SC5314. Biofilm formation was measured in an assay that quantitates biofilms by staining with a crystal violet dye. The amount of dye absorbed by the biofilm positively correlates with amount of biofilm present. Amount of dye is measured via an optical density reading at a wavelength of 600 nm (OD600). Biofilm formation is measured over 24 hours in the presence or absence of peptides at 10, 30, or 40 uM concentrations.

It is contemplated that PYY prevents formation of *C. albicans* biofilms through insertion into the membrane of the hyphal tip of *C. albicans* and subsequent permeabilization of those membranes through formation of a pore, and that the amphipathic nature of the α-helix is important for the formation of this pore. Therefore, AVpeptides 9-11, 23, and 25 (SEQ ID NOs: 15-17, 29, and 31) were designed to increase the hydrophobic moment of the α-helix by removing polar or charged amino acid residues from the hydrophobic face and replacing them with nonpolar residues (FIG. 12). Experiments conducted during development of embodiments herein demonstrated that that these peptides greatly inhibited biofilm formation by *C. albicans* at concentrations lower than $PYY_{13-36}$. Antifungal activity of peptides described in this application was tested by performing a crystal violet based biofilm assay. In this assay, *Candida albicans* is induced to form a biofilm in a 96-well plate for 24 hours in the presence or absence of peptide. Biofilm formation is quantitated through crystal violet staining and solubilization followed by optical density reading. The attached data table describes the results of these assays at a range of peptide concentrations. Data are OD600 values normalized to appropriate within experiment vehicle control. Statistical analysis was performed via 2-Way ANOVA with multiple comparisons post-test. Significance is denoted by: *=p<0.05; =p<0.01; *-p<0.001; ****=p<0.0001. ns=not significant. Other peptides tested resulted in reduced efficacy or did not substantially change the efficacy relative to $PYY_{13-36}$. FIG. 13 and Tables 1A-C demonstrates the effects of substitutions on inhibition of biofilm formation by *C. albicans* for exemplary peptides. AVpeptide 25 has had additional mutations introduced on the hydrophilic face to increase peptide stability. AVpeptides 28, 29, 30, and 31 (SEQ ID NOs: 34-37) were designed based on a sequence alignment between PYY from *Homo sapiens* and an evolutionarily related peptide, skinPYY, produced by the frog *Phyllomedusa bicolor*. Amphibian skinPYY also has antifungal properties and a high degree of sequence homology with PYY. Mutations in AVpeptides 28, 29, 30, and 31 were based on this similarity. Each of AVpeptides 9-11, 23, 25, and 28-31, as well as AVpeptides 20 and 32 (SEQ ID NOs: 26 and 38), exhibited increased inhibition of biofilm formation by *Candida albicans* relative to $PYY_{13-36}$ (SEQ ID NO: 6).

TABLE 1A

AVpeptide inhibition of biofilm formation (10 μM peptide)

| - | Mean Normalized to vehicle control | Significance from vehicle | Significance from Native PYY |
|---|---|---|---|
| PYY13-36 | 0.87 | ns | NA |
| " | 0.81 | * | NA |
| " | 0.94 | ns | NA |
| " | 0.83 | ns | NA |
| " | 0.71 | *** | NA |
| AVpeptide 1 | 0.96 | ns | Not tested |
| AVpeptide 1 | 0.95 | ns | ns |
| AVpeptide 2 | 1.05 | ns | Not tested |
| " | 1.02 | ns | ns |
| AVpeptide 3 | 1.00 | ns | Not tested |
| " | 0.94 | ns | ns |
| AVpeptide 4 | 1.04 | ns | Not tested |
| " | 0.98 | ns | ns |
| AVpeptide 5 | 0.64 | **** | +++ |
| " | 0.76 | * | ns |
| AVpeptide 6 | 0.97 | ns | ns |
| AVpeptide 7 | 0.97 | ns | ns |
| AVpeptide 8 | 0.97 | ns | ns |
| AVpeptide 9 | 0.39 | **** | ++++ |
| " | 0.08 | **** | ++++ |
| " | 0.51 | **** | ++++ |
| AVpeptide 10 | 0.11 | **** | ++++ |
| " | 0.00 | **** | ++++ |
| " | 0.09 | **** | ++++ |
| AVpeptide 11 | 0.12 | **** | ++++ |
| " | 0.16 | **** | ++++ |
| " | 0.01 | **** | ++++ |
| AVpeptide 12 | 1.01 | ns | ns |
| AVpeptide 13 | 0.95 | ns | ns |
| AVpeptide 14 | 0.82 | ns | ns |
| AVpeptide 15 | 0.96 | ns | ns |
| AVpeptide 16 | 1.06 | ns | ns |
| AVpeptide 17 | 0.91 | ns | ns |
| AVpeptide 18 | 1.11 | ns | -- |
| AVpeptide 19 | 1.06 | ns | ns |
| AVpeptide 20 | 0.47 | **** | ++++ |
| " | 0.52 | **** | ++++ |
| " | 0.62 | **** | +++ |
| AVpeptide 21 | 0.92 | ns | |
| AVpeptide 22 | 0.84 | ns | ns |
| AVpeptide 23 | 0.03 | **** | ++++ |
| " | 0.03 | **** | ++++ |
| AVpeptide 24 | 0.83 | ns | ns |
| AVpeptide 25 | 0.01 | **** | ++++ |
| " | 0.03 | **** | ++++ |
| AVpeptide 26 | | | -- |
| AVpeptide 27 | 0.66 | **** | ns |
| AVpeptide 28 | 0.22 | **** | ++++ |
| " | 0.58 | **** | ++ |
| AVpeptide 29 | 0.58 | **** | ++ |
| AVpeptide 30 | 0.16 | **** | ++++ |
| " | 0.10 | **** | ++++ |
| AVpeptide 31 | 0.05 | **** | ++++ |
| AVpeptide 32 | 0.00 | **** | ++++ |
| " | 0.01 | **** | ++++ |

"*" indicates degree of significance
"+" indicates degree of positive change in inhibition of biofilm formation
"-" indicates degree of negative change in inhibition of biofilm formation
"ns" not significant
"NA" not applicable

TABLE 1B

AVpeptide inhibition of biofilm formation (30 μM peptide)

| - | Mean Normalized to vehicle control | Significance from vehicle | Significance from Native PYY |
|---|---|---|---|
| PYY13-36 | 0.48 | **** | NA |
| " | 0.11 | **** | NA |
| " | 0.17 | **** | NA |
| " | 0.19 | **** | NA |
| " | 0.12 | **** | NA |
| " | 0.13 | **** | NA |
| AVpeptide 1 | 0.74 | **** | ++++ |
| AVpeptide 1 | 0.40 | **** | +++ |
| AVpeptide 2 | 0.91 | ns | ++++ |
| " | 1.08 | ns | ++++ |
| AVpeptide 3 | 0.90 | ns | ++++ |
| " | 0.93 | ns | ++++ |
| AVpeptide 4 | 0.89 | ns | ++++ |
| " | 0.94 | ns | ++++ |
| AVpeptide 5 | 0.28 | **** | ns |
| " | 0.53 | **** | ++++ |
| AVpeptide 6 | 0.52 | **** | ++++ |
| AVpeptide 7 | 0.08 | **** | ns |
| AVpeptide 8 | 0.71 | *** | ++++ |
| AVpeptide 9 | 0.07 | **** | ns |
| " | 0.00 | **** | ns |
| " | 0.09 | **** | ns |
| AVpeptide 10 | 0.06 | **** | ns |
| " | 0.07 | **** | ns |
| " | 0.03 | **** | ns |
| AVpeptide 11 | 0.15 | **** | ns |
| " | 0.09 | **** | ns |
| " | 0.69 | *** | ++++ |
| AVpeptide 12 | 0.46 | **** | ++++ |
| AVpeptide 13 | 0.14 | **** | ns |
| AVpeptide 14 | 0.07 | **** | ns |
| AVpeptide 15 | 0.78 | * | ++++ |
| AVpeptide 16 | 1.02 | ns | ++++ |
| AVpeptide 17 | 0.94 | ns | ++++ |
| AVpeptide 18 | 0.16 | **** | ns |
| AVpeptide 19 | 1.01 | ns | ++++ |
| AVpeptide 20 | 1.07 | ns | ++++ |
| " | 1.25 | * | ++++ |
| " | 1.03 | ns | ++++ |
| AVpeptide 21 | 0.02 | **** | ns |
| AVpeptide 22 | 0.37 | **** | ns |
| AVpeptide 23 | 0.19 | **** | ns |
| " | 0.75 | * | ++++ |
| AVpeptide 24 | 0.71 | *** | ++++ |

TABLE 1B-continued

AVpeptide inhibition of biofilm formation (30 μM peptide)

| - | Mean Normalized to vehicle control | Significance from vehicle | Significance from Native PYY |
|---|---|---|---|
| AVpeptide 25 | 0.01 | **** | ns |
| " | 0.02 | **** | ns |
| AVpeptide 26 | | | |
| AVpeptide 27 | 0.08 | **** | ns |
| AVpeptide 28 | 0.09 | **** | ns |
| " | 0.17 | **** | ns |
| AVpeptide 29 | 0.04 | **** | ns |
| AVpeptide 30 | 0.02 | **** | ns |
| " | 0.02 | **** | ns |
| AVpeptide 31 | 1.00 | ns | ++++ |
| AVpeptide 32 | 0.00 | **** | ns |
| " | 0.02 | **** | ns |

"*" indicates degree of significance
"+" indicates degree of positive change in inhibition of biofilm formation
"−" indicates degree of negative change in inhibition of biofilm formation
"ns" not significant
"NA" not applicable

TABLE 1C

AVpeptide inhibition of biofilm formation (40 μM peptide)

| - | Mean Normalized to vehicle control | Significance from vehicle | Significance from Native PYY |
|---|---|---|---|
| PYY13-36 | 0.05 | **** | NA |
| AVpeptide 1 | 0.14 | **** | ns |
| AVpeptide 2 | 1.01 | ns | ++++ |
| AVpeptide 3 | 0.91 | ns | ++++ |
| AVpeptide 4 | 0.88 | ns | ++++ |
| AVpeptide 6 | 0.28 | **** | + |
| AVpeptide 7 | 0.33 | **** | ++ |
| AVpeptide 8 | 0.31 | **** | ++ |
| AVpeptide 9 | 0.05 | **** | ns |
| AVpeptide 10 | 0.17 | **** | ns |
| AVpeptide 11 | 0.99 | ns | ++++ |
| AVpeptide 12 | 0.15 | **** | ns |
| AVpeptide 13 | 0.07 | **** | ns |
| AVpeptide 14 | 0.07 | **** | ns |
| AVpeptide 15 | 0.69 | *** | ++++ |
| AVpeptide 16 | 0.95 | ns | ++++ |
| AVpeptide 18 | 0.05 | **** | ns |
| AVpeptide 19 | 0.97 | ns | ++++ |
| AVpeptide 20 | 1.04 | ns | ++++ |

"*" indicates degree of significance
"+" indicates degree of positive change in inhibition of biofilm formation
"−" indicates degree of negative change in inhibition of biofilm formation
"ns" not significant
"NA" not applicable PYY variants that exhibited reduced efficacy in inhibiting formation of biofilm in vitro by *Candida albicans*, relative to PYY$_{13-36}$, included AVpeptides 2-4, 6, 8, 15-17, 19, and 24. However, these variants and/or the substitutions they contain may confer other desirable traits and may appear in PYY variants in some embodiments herein.

PYY variants that exhibited similar efficacy in inhibiting formation of biofilm in vitro by *Candida albicans*, relative to PYY$_{13-36}$, included AVpeptides 1, 5, 7, 12-14, 18, 21, 22, and 27. However, these variants and/or the substitutions they contain may confer other desirable traits and may appear in PYY variants in some embodiments herein.

Example 3

Figure 14:
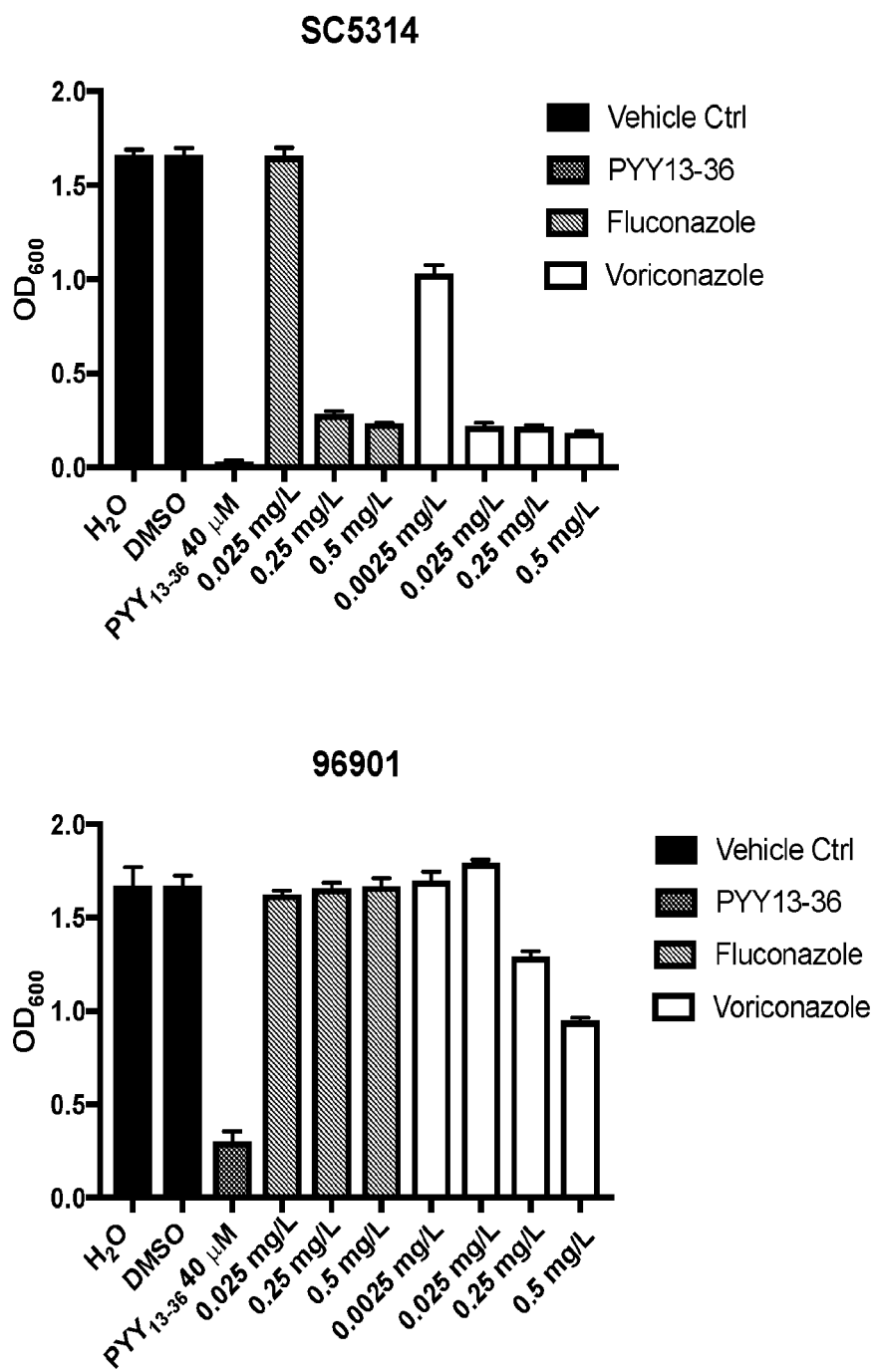
FIG. 14. PYY$_{13-36}$ prevents biofilm formation by a fluconazole resistant strain of Candida albicans. Biofilm formation is measured here in an assay that quantitates biofilms by staining with a crystal violet dye. The amount of dye absorbed by the biofilm positively correlates with amount of biofilm present. Amount of dye is measured via an optical density reading at a wavelength of 600 nm (OD600). Biofilm formation by a fluconazole sensitive (SC5314) or resistant (ATCC96901, 321182) strain of C. albicans is measured over 24 hours in the presence or absence of peptides or antifungal drugs at indicated concentrations.
Figure 16:
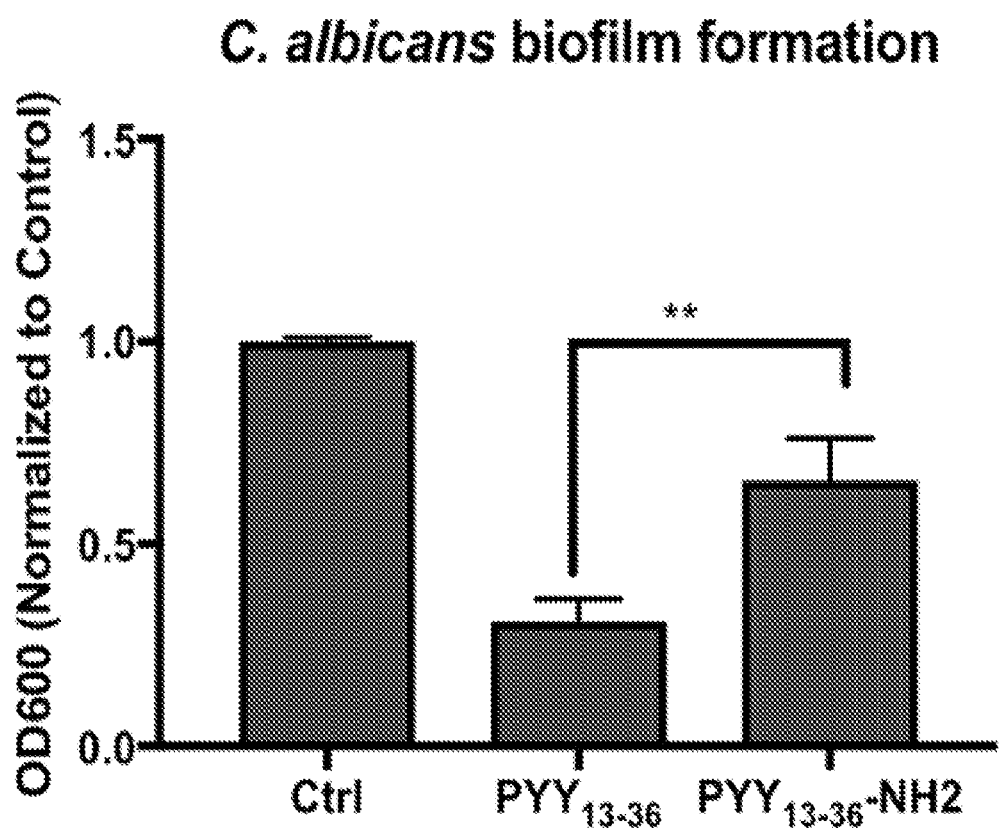
FIG. 16. PYY$_{13-36}$ is more effective than PYY$_{13-36}$ with an amidated C-terminus (PYY$_{13-36}$-NH2) at inhibiting C. albicans biofilm formation. Biofilm formation is measured here in an assay that quantitates biofilms by staining with a crystal violet dye. The amount of dye absorbed by the biofilm positively correlates with amount of biofilm present. Amount of dye is measured via an optical density reading at a wavelength of 600 nm (OD600). Data presented is an average of 3 independent biological replicates measuring biofilm formation over 24 hours in the presence or absence of peptides at 30 or 40 uM concentrations.

Experiments were conducted during development of embodiments herein to demonstrate the use of PYY based peptides as prophylactics for or therapeutics against drug resistant strains of *C. albicans* (FIG. 14).

REFERENCES

The following references, some of which are cited above by number, are herein incorporated by reference in their entireties.

1. Conlon J M. The origin and evolution of peptide Y Y (PYY) and pancreatic polypeptide (PP). Peptides. 2002; 23 (2): 269-78. PubMed PMID: 11825642.
2. Batterham R L, ffytche D H, Rosenthal J M, Zelaya F O, Barker G J, Withers D J, Williams S C. PYY modulation of cortical and hypothalamic brain areas predicts feeding behaviour in humans. Nature. 2007; 450 (7166): 106-9. doi: 10.1038/nature06212. PubMed PMID: 17934448.
3. Glavas M M, Grayson B E, Allen S E, Copp D R, Smith M S, Cowley M A, Grove K L. Characterization of brainstem peptide YY (PYY) neurons. J Comp Neurol. 2008; 506 (2): 194-210. doi: 10.1002/cne.21543. PubMed PMID: 18022952.
4. Hill B R, De Souza M J, Williams N I. Characterization of the diurnal rhythm of peptide YY and its association with energy balance parameters in normal-weight pre-menopausal women. Am J Physiol Endocrinol Metab. 2011; 301 (2): E409-15. doi: 10.1152/ajpendo.00171.2011. PubMed PMID: 21610227; PMCID: PMC3154533.
5. Holzer P, Reichmann F, Farzi A. Neuropeptide Y, peptide YY and pancreatic polypeptide in the gut-brain axis. Neuropeptides. 2012; 46 (6): 261-74. doi: 10.1016/j.npep.2012.08.005. PubMed PMID: 22979996; PMCID: PMC3516703.
6. Tatemoto K. Isolation and characterization of peptide YY (PYY), a candidate gut hormone that inhibits pancreatic exocrine secretion. Proc Natl Acad Sci USA. 1982; 79 (8): 2514-8. PubMed PMID: 6953409; PMCID: PMC346229.
7. Gunawardene A R, Corfe B M, Staton C A. Classification and functions of enteroendocrine cells of the lower gastrointestinal tract. Int J Exp Pathol. 2011; 92 (4): 219-31. doi: 10.1111/j.1365-2613.2011.00767.x. PubMed PMID: 21518048; PMCID: PMC3144510.
8. Lambert R W, Campton K, Ding W, Ozawa H, Granstein R D. Langerhans cell expression of neuropeptide Y and peptide YY. Neuropeptides. 2002; 36 (4): 246-51. PubMed PMID: 12372697.
9. Clevers H C, Bevins C L. Paneth cells: maestros of the small intestinal crypts. Annu Rev Physiol. 2013; 75:289-311. doi: 10.1146/annurev-physiol-030212-183744. PubMed PMID: 23398152.
10. Vouldoukis I, Shai Y, Nicolas P, Mor A. Broad spectrum antibiotic activity of the skin-PYY. FEBS Lett. 1996; 380 (3): 237-40. PubMed PMID: 8601432.

SEQUENCES

SEQ ID NO: 1    (PYY) - YPIKPEAPGEDASPEELNRYYASLRHYLNLVTRQRY

SEQ ID NO: 2    (PYY$_{14-36}$) - PEELNRYYASLRHYLNLVTRQRY

| SEQUENCES |
|---|
| SEQ ID NO: 3      PX$_1$ELNRYYASLRX$_2$YLNX$_3$VTRQX$_4$X$_5$ (wherein each Xx is independently selected from any natural or unnatural amino acid) |
| SEQ ID NO: 4      PDELNRYYASLRKYLNAVTRQLA |
| SEQ ID NO: 5      PDELNRYYASLRKYLNAVTRQLR |
| SEQ ID NO: 6      (PYY$_{13-36}$) - SPEELNRYYASLRHYLNLVTRQRY |
| SEQ ID NO: 7      AVpeptide 1 - PEELNRYYASLRHYLNLVTRQLY (14-36; R35L) |
| SEQ ID NO: 8      AVpeptide 2 - PEELNRYYASLRHYLNAVTRQRY ($_{14-36}$, L30A) |
| SEQ ID NO: 9      AVpeptide 3 - PEELNRYYASLRHYLNLVTRQRA ($_{14-36}$, Y36A) |
| SEQ ID NO: 10     AVpeptide 4 - PEELNRYYASLRHYLNAVTRQLA ($_{14-36}$, L30A; R35L; Y36A) |
| SEQ ID NO: 11     AVpeptide 5 - SPEELNRYYASLRHYLNLVTRQRR (Y36R) |
| SEQ ID NO: 12     AVpeptide 6 - SPEELNRYYASLRHYLNLVTRQLR |
| SEQ ID NO: 13     AVpeptide 7 - SPEELNRYYASLRHYLNLVTRQYY (R35Y) |
| SEQ ID NO: 14     AVpeptide 8 - SPEELNRYYASLRHYLNLVTRQVY (R35V) |
| SEQ ID NO: 15     AVpeptide 9 (N29R; R35L): SPEELNRYYASLRHYLRLVTRQLY |
| SEQ ID NO: 16     AVpeptide 10 (S13L): LPEELNRYYASLRHYLNLVTRQRY |
| SEQ ID NO: 17     AVpeptide 11 (S13L; R35L): LPEELNRYYASLRHYLNLVTRQLY |
| SEQ ID NO: 18     AVpeptide 12 - SPEELNRYYASLRHYYNLVTRQRY (L28Y) |
| SEQ ID NO: 19     AVpeptide 13 - SPEQLNRYYASLRHYLNLVTRERY (E16Q, Q34A) |
| SEQ ID NO: 20     AVpeptide 14 - SPDELNRYYASLRKYLNLVTRQRY (E15D, H26K) |
| SEQ ID NO: 21     AVpeptide 15 - SPEELNRYYASLRHYLNLVTRQ (13-34) |
| SEQ ID NO: 22     AVpeptide 16 - YPEEYNRYYASYRHYLNHVTRQRY (S13Y L17Y L24Y L30H) |
| SEQ ID NO: 23     AVpeptide 17 - YPEEYNRYYASYRHYLNLVTRQRY (S13Y L17Y L24Y) |
| SEQ ID NO: 24     AVpeptide 18 - ASPEELNRYYASLRHYLNLVTRQRY ($_{12-36}$) |
| SEQ ID NO: 25     AVpeptide 19 - SPEELNRYYASSRHYLNLVTRQRY (L24S) |
| SEQ ID NO: 26     AVpeptide 20 - SPEELNRYYLSLRHYLNLVTRQRY (A22L) |
| SEQ ID NO: 27     AVpeptide 21 - SPEELNRYYASLRHYLNLVTRQLY (R35L) |
| SEQ ID NO: 28     AVpeptide 22 - SPEELNRYYASLRHYLRLVTRQRY (N29R) |
| SEQ ID NO: 29     AVpeptide 23 - LPEELNRYYASLRHYLRLVTRQLY (S13L, N29R, R35L) |
| SEQ ID NO: 30     AVpeptide 24 - SPEELNRYYASLRHYLNLVTRQR (PYY13-35) |
| SEQ ID NO: 31     AVpeptide 25 - LPDELNRYYASLRKYLNLVTRQRY (S13L, E15D, H26K) |
| SEQ ID NO: 32     AVpeptide 26 - SPEEMNRYYASLRHYLNLVTRQRY (L17M) |
| SEQ ID NO: 33     AVpeptide 27 - SPEELNKYYASLRHYLNLVTRQRY (R19K) |
| SEQ ID NO: 34     AVpeptide 28 - SPEELNRYLASLRHYLNLVTRQRY (Y21L) |
| SEQ ID NO: 35     AVpeptide 29 - SPEELNRYYASLRHYINLVTRQRY (L28I) |
| SEQ ID NO: 36     AVpeptide 30 - SPEELNRYYTALRHYLNLVTRQRY (A22T, S23A) |

| SEQUENCES | |
|---|---|
| SEQ ID NO: 37 | AVpeptide 31 - SPEELNRYYLALRHYLNLVTRQRY (A22L, S23A) |
| SEQ ID NO: 38 | AVpeptide 32 - SPEELNRLLASLRHLLNLVTRQRY (Y20L, Y21L, Y27L) |
| SEQ ID NO: 39 | $X_1PX_2ELNRYYASLRX_3YLX_4X_5VTRQX_6X_7$ (wherein each Xx is independently selected from any natural or unnatural amino acid) |
| SEQ ID NO: 40 | $X_1PX_2ELNRX_3X_4X_5X_6LRX_7X_8X_9NLVTRQX_{10}Y$ (wherein each Xx is independently selected from any natural or unnatural amino acid) |
| SEQ ID NO: 41 | $X_1PX_2ELNRX_3X_4X_5X_6LRX_7X_8X_9NLVTRQRY$ (wherein each Xx is independently selected from any natural or unnatural amino acid) |
| SEQ ID NO: 42 | LP(E/D)ELNRLLLALRKL(R/I)NLVTRQLY |
| SEQ ID NO: 43 | $X_1X_2E(D/E)(M/L)X_3RYY(S/A)(S/A)LRHY(I/L)NL(IN)TRQRY$ (wherein each Xx is independently selected from any natural or unnatural amino acid) |
| SEQ

```
      occurring amino acid
<220> FEATURE:
<221> NAME/KEY: misc_feature
<222> LOCATION: (13)..(13)
<223> OTHER INFORMATION: Xaa can be any naturally or unnaturally
      occurring amino acid
<220> FEATURE:
<221> NAME/KEY: misc_feature
<222> LOCATION: (17)..(17)
<223> OTHER INFORMATION: Xaa can be any naturally or unnaturally
      occurring amino acid
<220> FEATURE:
<221> NAME/KEY: misc_feature
<222> LOCATION: (22)..(23)
<223> OTHER INFORMATION: Xaa can be any naturally or unnaturally
      occurring amino acid

<400> SEQUENCE: 3

Pro Xaa Glu Leu Asn Arg Tyr Tyr Ala Ser Leu Arg Xaa Tyr Leu Asn
1               5                   10                  15

Xaa Val Thr Arg Gln Xaa Xaa
            20

<210> SEQ ID NO 4
<211> LENGTH: 23
<212> TYPE: PRT
<213> ORGANISM: Artificial sequence
<220> FEATURE:
<223> OTHER INFORMATION: Synthetic peptide

<400> SEQUENCE: 4

Pro Asp Glu Leu Asn Arg Tyr Tyr Ala Ser Leu Arg Lys Tyr Leu Asn
1               5                   10                  15

Ala Val Thr Arg Gln Leu Ala
            20

<210> SEQ ID NO 5
<211> LENGTH: 23
<212> TYPE: PRT
<213> ORGANISM: Artificial sequence
<220> FEATURE:
<223> OTHER INFORMATION: Synthetic peptide

<400> SEQUENCE: 5

Pro Asp Glu Leu Asn Arg Tyr Tyr Ala Ser Leu Arg Lys Tyr Leu Asn
1               5                   10                  15

Ala Val Thr Arg Gln Leu Arg
            20

<210> SEQ ID NO 6
<211> LENGTH: 24
<212> TYPE: PRT
<213> ORGANISM: Homo sapiens

<400> SEQUENCE: 6

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 7
<211> LENGTH: 23
<212> TYPE: PRT
<213> ORGANISM: Artificial sequence
<220> FEATURE:
<223> OTHER INFORMATION: Synthetic peptide
```

-continued

```
<400> SEQUENCE: 7

Pro Glu Glu Leu Asn Arg Tyr Tyr Ala Ser Leu Arg His Tyr Leu Asn
1               5                   10                  15

Leu Val Thr Arg Gln Leu Tyr
            20

<210> SEQ ID NO 8
<211> LENGTH: 23
<212> TYPE: PRT
<213> ORGANISM: Artificial sequence
<220> FEATURE:
<223> OTHER INFORMATION: Synthetic peptide

<400> SEQUENCE: 8

Pro Glu Glu Leu Asn Arg Tyr Tyr Ala Ser Leu Arg His Tyr Leu Asn
1               5                   10                  15

Ala Val Thr Arg Gln Arg Tyr
            20

<210> SEQ ID NO 9
<211> LENGTH: 23
<212> TYPE: PRT
<213> ORGANISM: Artificial sequence
<220> FEATURE:
<223> OTHER INFORMATION: Synthetic peptide

<400> SEQUENCE: 9

Pro Glu Glu Leu Asn Arg Tyr Tyr Ala Ser Leu Arg His Tyr Leu Asn
1               5                   10                  15

Leu Val Thr Arg Gln Arg Ala
            20

<210> SEQ ID NO 10
<211> LENGTH: 23
<212> TYPE: PRT
<213> ORGANISM: Artificial sequence
<220> FEATURE:
<223> OTHER INFORMATION: Synthetic peptide

<400> SEQUENCE: 10

Pro Glu Glu Leu Asn Arg Tyr Tyr Ala Ser Leu Arg His Tyr Leu Asn
1               5                   10                  15

Ala Val Thr Arg Gln Leu Ala
            20

<210> SEQ ID NO 11
<211> LENGTH: 24
<212> TYPE: PRT
<213> ORGANISM: Artificial sequence
<220> FEATURE:
<223> OTHER INFORMATION: Synthetic peptide

<400> SEQUENCE: 11

Ser Pro Glu Glu Leu Asn Arg Tyr Tyr Ala Ser Leu Arg His Tyr Leu
1               5                   10                  15

Asn Leu Val Thr Arg Gln Arg Arg
            20

<210> SEQ ID NO 12
<211> LENGTH: 24
<212> TYPE: PRT
<213> ORGANISM: Artificial sequence
<220> FEATURE:
<223> OTHER INFORMATION: Synthetic peptide
```

<400> SEQUENCE: 12

Ser Pro Glu Glu Leu Asn Arg Tyr Tyr Ala Ser Leu Arg His Tyr Leu
1               5                   10                  15

Asn Leu Val Thr Arg Gln Leu Arg
            20

<210> SEQ ID NO 13
<211> LENGTH: 24
<212> TYPE: PRT
<213> ORGANISM: Artificial sequence
<220> FEATURE:
<223> OTHER INFORMATION: Synthetic peptide

<400> SEQUENCE: 13

Ser Pro Glu Glu Leu Asn Arg Tyr Tyr Ala Ser Leu Arg His Tyr Leu
1               5                   10                  15

Asn Leu Val Thr Arg Gln Tyr Tyr
            20

<210> SEQ ID NO 14
<211> LENGTH: 24
<212> TYPE: PRT
<213> ORGANISM: Artificial sequence
<220> FEATURE:
<223> OTHER INFORMATION: Synthetic peptide

<400> SEQUENCE: 14

Ser Pro Glu Glu Leu Asn Arg Tyr Tyr Ala Ser Leu Arg His Tyr Leu
1               5                   10                  15

Asn Leu Val Thr Arg Gln Val Tyr
            20

<210> SEQ ID NO 15
<211> LENGTH: 24
<212> TYPE: PRT
<213> ORGANISM: Artificial sequence
<220> FEATURE:
<223> OTHER INFORMATION: Synthetic peptide

<400> SEQUENCE: 15

Ser Pro Glu Glu Leu Asn Arg Tyr Tyr Ala Ser Leu Arg His Tyr Leu
1               5                   10                  15

Arg Leu Val Thr Arg Gln Leu Tyr
            20

<210> SEQ ID NO 16
<211> LENGTH: 24
<212> TYPE: PRT
<213> ORGANISM: Artificial sequence
<220> FEATURE:
<223> OTHER INFORMATION: Synthetic peptide

<400> SEQUENCE: 16

Leu Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 17
<211> LENGTH: 24
<212> TYPE: PRT
<213> ORGANISM: Artificial sequence
<220> FEATURE:

<223> OTHER INFORMATION: Synthetic peptide

<400> SEQUENCE: 17

Leu Pro Glu Glu Leu Asn Arg Tyr Tyr Ala Ser Leu Arg His Tyr Leu
1               5                   10                  15

Asn Leu Val Thr Arg Gln Leu Tyr
            20

<210> SEQ ID NO 18
<211> LENGTH: 24
<212> TYPE: PRT
<213> ORGANISM: Artificial sequence
<220> FEATURE:
<223> OTHER INFORMATION: Synthetic peptide

<400> SEQUENCE: 18

Ser Pro Glu Glu Leu Asn Arg Tyr Tyr Ala Ser Leu Arg His Tyr Tyr
1               5                   10                  15

Asn Leu Val Thr Arg Gln Arg Tyr
            20

<210> SEQ ID NO 19
<211> LENGTH: 24
<212> TYPE: PRT
<213> ORGANISM: Artificial sequence
<220> FEATURE:
<223> OTHER INFORMATION: Synthetic peptide

<400> SEQUENCE: 19

Ser Pro Glu Gln Leu Asn Arg Tyr Tyr Ala Ser Leu Arg His Tyr Leu
1               5                   10                  15

Asn Leu Val Thr Arg Glu Arg Tyr
            20

<210> SEQ ID NO 20
<211> LENGTH: 24
<212> TYPE: PRT
<213> ORGANISM: Artificial sequence
<220> FEATURE:
<223> OTHER INFORMATION: Synthetic peptide

<400> SEQUENCE: 20

Ser Pro Asp Glu Leu Asn Arg Tyr Tyr Ala Ser Leu Arg Lys Tyr Leu
1               5                   10                  15

Asn Leu Val Thr Arg Gln Arg Tyr
            20

<210> SEQ ID NO 21
<211> LENGTH: 22
<212> TYPE: PRT
<213> ORGANISM: Artificial sequence
<220> FEATURE:
<223> OTHER INFORMATION: Synthetic peptide

<400> SEQUENCE: 21

Ser Pro Glu Glu Leu Asn Arg Tyr Tyr Ala Ser Leu Arg His Tyr Leu
1               5                   10                  15

Asn Leu Val Thr Arg Gln
            20

<210> SEQ ID NO 22
<211> LENGTH: 24
<212> TYPE: PRT
<213> ORGANISM: Artificial sequence

```
<220> FEATURE:
<223> OTHER INFORMATION: Synthetic peptide

<400> SEQUENCE: 22

Tyr Pro Glu Glu Tyr Asn Arg Tyr Tyr Ala Ser Tyr Arg His Tyr Leu
1               5                   10                  15
Asn His Val Thr Arg Gln Arg Tyr
            20

<210> SEQ ID NO 23
<211> LENGTH: 24
<212> TYPE: PRT
<213> ORGANISM: Artificial sequence
<220> FEATURE:
<223> OTHER INFORMATION: Synthetic peptide

<400> SEQUENCE: 23

Tyr Pro Glu Glu Tyr Asn Arg Tyr Tyr Ala Ser Tyr Arg His Tyr Leu
1               5                   10                  15
Asn Leu Val Thr Arg Gln Arg Tyr
            20

<210> SEQ ID NO 24
<211> LENGTH: 25
<212> TYPE: PRT
<213> ORGANISM: Artificial sequence
<220> FEATURE:
<223> OTHER INFORMATION: Synthetic peptide

<400> SEQUENCE: 24

Ala Ser Pro Glu Glu Leu Asn Arg Tyr Tyr Ala Ser Leu Arg His Tyr
1               5                   10                  15
Leu Asn Leu Val Thr Arg Gln Arg Tyr
            20                  25

<210> SEQ ID NO 25
<211> LENGTH: 24
<212> TYPE: PRT
<213> ORGANISM: Artificial sequence
<220> FEATURE:
<223> OTHER INFORMATION: Synthetic peptide

<400> SEQUENCE: 25

Ser Pro Glu Glu Leu Asn Arg Tyr Tyr Ala Ser Ser Arg His Tyr Leu
1               5                   10                  15
Asn Leu Val Thr Arg Gln Arg Tyr
            20

<210> SEQ ID NO 26
<211> LENGTH: 24
<212> TYPE: PRT
<213> ORGANISM: Artificial sequence
<220> FEATURE:
<223> OTHER INFORMATION: Synthetic peptide

<400> SEQUENCE: 26

Ser Pro Glu Glu Leu Asn Arg Tyr Tyr Leu Ser Leu Arg His Tyr Leu
1               5                   10                  15
Asn Leu Val Thr Arg Gln Arg Tyr
            20

<210> SEQ ID NO 27
<211> LENGTH: 24
<212> TYPE: PRT
```

```
<213> ORGANISM: Artificial sequence
<220> FEATURE:
<223> OTHER INFORMATION: Synthetic peptide

<400> SEQUENCE: 27

Ser Pro Glu Glu Leu Asn Arg Tyr Tyr Ala Ser Leu Arg His Tyr Leu
1               5                   10                  15

Asn Leu Val Thr Arg Gln Leu Tyr
            20

<210> SEQ ID NO 28
<211> LENGTH: 24
<212> TYPE: PRT
<213> ORGANISM: Artificial sequence
<220> FEATURE:
<223> OTHER INFORMATION: Synthetic peptide

<400> SEQUENCE: 28

Ser Pro Glu Glu Leu Asn Arg Tyr Tyr Ala Ser Leu Arg His Tyr Leu
1               5                   10                  15

Arg Leu Val Thr Arg Gln Arg Tyr
            20

<210> SEQ ID NO 29
<211> LENGTH: 24
<212> TYPE: PRT
<213> ORGANISM: Artificial sequence
<220> FEATURE:
<223> OTHER INFORMATION: Synthetic peptide

<400> SEQUENCE: 29

Leu Pro Glu Glu Leu Asn Arg Tyr Tyr Ala Ser Leu Arg His Tyr Leu
1               5                   10                  15

Arg Leu Val Thr Arg Gln Leu Tyr
            20

<210> SEQ ID NO 30
<211> LENGTH: 23
<212> TYPE: PRT
<213> ORGANISM: Artificial sequence
<220> FEATURE:
<223> OTHER INFORMATION: Synthetic peptide

<400> SEQUENCE: 30

Ser Pro Glu Glu Leu Asn Arg Tyr Tyr Ala Ser Leu Arg His Tyr Leu
1               5                   10                  15

Asn Leu Val Thr Arg Gln Arg
            20

<210> SEQ ID NO 31
<211> LENGTH: 24
<212> TYPE: PRT
<213> ORGANISM: Artificial sequence
<220> FEATURE:
<223> OTHER INFORMATION: Synthetic peptide

<400> SEQUENCE: 31

Leu Pro Asp Glu Leu Asn Arg Tyr Tyr Ala Ser Leu Arg Lys Tyr Leu
1               5                   10                  15

Asn Leu Val Thr Arg Gln Arg Tyr
            20

<210> SEQ ID NO 32
<211> LENGTH: 24
```

```
<212> TYPE: PRT
<213> ORGANISM: Artificial sequence
<220> FEATURE:
<223> OTHER INFORMATION: Synthetic peptide

<400> SEQUENCE: 32

Ser Pro Glu Glu Met Asn Arg Tyr Tyr Ala Ser Leu Arg His Tyr Leu
1               5                   10                  15

Asn Leu Val Thr Arg Gln Arg Tyr
            20

<210> SEQ ID NO 33
<211> LENGTH: 24
<212> TYPE: PRT
<213> ORGANISM: Artificial sequence
<220> FEATURE:
<223> OTHER INFORMATION: Synthetic peptide

<400> SEQUENCE: 33

Ser Pro Glu Glu Leu Asn Lys Tyr Tyr Ala Ser Leu Arg His Tyr Leu
1               5                   10                  15

Asn Leu Val Thr Arg Gln Arg Tyr
            20

<210> SEQ ID NO 34
<211> LENGTH: 24
<212> TYPE: PRT
<213> ORGANISM: Artificial sequence
<220> FEATURE:
<223> OTHER INFORMATION: Synthetic peptide

<400> SEQUENCE: 34

Ser Pro Glu Glu Leu Asn Arg Tyr Leu Ala Ser Leu Arg His Tyr Leu
1               5                   10                  15

Asn Leu Val Thr Arg Gln Arg Tyr
            20

<210> SEQ ID NO 35
<211> LENGTH: 24
<212> TYPE: PRT
<213> ORGANISM: Artificial sequence
<220> FEATURE:
<223> OTHER INFORMATION: Synthetic peptide

<400> SEQUENCE: 35

Ser Pro Glu Glu Leu Asn Arg Tyr Tyr Ala Ser Leu Arg His Tyr Ile
1               5                   10                  15

Asn Leu Val Thr Arg Gln Arg Tyr
            20

<210> SEQ ID NO 36
<211> LENGTH: 24
<212> TYPE: PRT
<213> ORGANISM: Artificial sequence
<220> FEATURE:
<223> OTHER INFORMATION: Synthetic peptide

<400> SEQUENCE: 36

Ser Pro Glu Glu Leu Asn Arg Tyr Tyr Thr Ala Leu Arg His Tyr Leu
1               5                   10                  15

Asn Leu Val Thr Arg Gln Arg Tyr
            20

<210> SEQ ID NO 37
```

```
<211> LENGTH: 24
<212> TYPE: PRT
<213> ORGANISM: Artificial sequence
<220> FEATURE:
<223> OTHER INFORMATION: Synthetic peptide

<400> SEQUENCE: 37

Ser Pro Glu Glu Leu Asn Arg Tyr Tyr Leu Ala Leu Arg His Tyr Leu
1               5                   10                  15

Asn Leu Val Thr Arg Gln Arg Tyr
            20

<210> SEQ ID NO 38
<211> LENGTH: 24
<212> TYPE: PRT
<213> ORGANISM: Artificial sequence
<220> FEATURE:
<223> OTHER INFORMATION: Synthetic peptide

<400> SEQUENCE: 38

Ser Pro Glu Glu Leu Asn Arg Leu Leu Ala Ser Leu Arg His Leu Leu
1               5                   10                  15

Asn Leu Val Thr Arg Gln Arg Tyr
            20

<210> SEQ ID NO 39
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally or unnaturally
      occurring amino acid
<220> FEATURE:
<221> NAME/KEY: misc_feature
<222> LOCATION: (3)..(3)
<223> OTHER INFORMATION: Xaa can be any naturally or unnaturally
      occurring amino acid
<220> FEATURE:
<221> NAME/KEY: misc_feature
<222> LOCATION: (14)..(14)
<223> OTHER INFORMATION: Xaa can be any naturally or unnaturally
      occurring amino acid
<220> FEATURE:
<221> NAME/KEY: misc_feature
<222> LOCATION: (17)..(18)
<223> OTHER INFORMATION: Xaa can be any naturally or unnaturally
      occurring amino acid
<220> FEATURE:
<221> NAME/KEY: misc_feature
<222> LOCATION: (23)..(24)
<223> OTHER INFORMATION: Xaa can be any naturally or unnaturally
      occurring amino acid

<400> SEQUENCE: 39

Xaa Pro Xaa Glu Leu Asn Arg Tyr Tyr Ala Ser Leu Arg Xaa Tyr Leu
1               5                   10                  15

Xaa Xaa Val Thr Arg Gln Xaa Xaa
            20

<210> SEQ ID NO 40
<211> LENGTH: 24
<212> TYPE: PRT
<213> ORGANISM: Artificial sequence
<220> FEATURE:
<223> OTHER INFORMATION: Synthetic peptide
<220> FEATURE:
```

<221> NAME/KEY: misc_feature
<222> LOCATION: (1)..(1)
<223> OTHER INFORMATION: Xaa can be any naturally or unnaturally
      occurring amino acid
<220> FEATURE:
<221> NAME/KEY: misc_feature
<222> LOCATION: (3)..(3)
<223> OTHER INFORMATION: Xaa can be any naturally or unnaturally
      occurring amino acid
<220> FEATURE:
<221> NAME/KEY: misc_feature
<222> LOCATION: (8)..(11)
<223> OTHER INFORMATION: Xaa can be any naturally or unnaturally
      occurring amino acid
<220> FEATURE:
<221> NAME/KEY: misc_feature
<222> LOCATION: (14)..(16)
<223> OTHER INFORMATION: Xaa can be any naturally or unnaturally
      occurring amino acid
<220> FEATURE:
<221> NAME/KEY: misc_feature
<222> LOCATION: (23)..(23)
<223> OTHER INFORMATION: Xaa can be any naturally or unnaturally
      occurring amino acid

<400> SEQUENCE: 40

Xaa Pro Xaa Glu Leu Asn Arg Xaa Xaa Xaa Xaa Leu Arg Xaa Xaa Xaa
1               5                   10                  15

Asn Leu Val Thr Arg Gln Xaa Tyr
            20

<210> SEQ ID NO 41
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally or unnaturally
      occurring amino acid
<220> FEATURE:
<221> NAME/KEY: misc_feature
<222> LOCATION: (3)..(3)
<223> OTHER INFORMATION: Xaa can be any naturally or unnaturally
      occurring amino acid
<220> FEATURE:
<221> NAME/KEY: misc_feature
<222> LOCATION: (8)..(11)
<223> OTHER INFORMATION: Xaa can be any naturally or unnaturally
      occurring amino acid
<220> FEATURE:
<221> NAME/KEY: misc_feature
<222> LOCATION: (14)..(16)
<223> OTHER INFORMATION: Xaa can be any naturally or unnaturally
      occurring amino acid

<400> SEQUENCE: 41

Xaa Pro Xaa Glu Leu Asn Arg Xaa Xaa Xaa Xaa Leu Arg Xaa Xaa Xaa
1               5                   10                  15

Asn Leu Val Thr Arg Gln Arg Tyr
            20

<210> SEQ ID NO 42
<211> LENGTH: 48
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)

```
<223> OTHER INFORMATION: Xaa = Glu or Asp
<220> FEATURE:
<221> NAME/KEY: MISC_FEATURE
<222> LOCATION: (16)..(16)
<223> OTHER INFORMATION: Xaa = Arg or Ile
<220> FEATURE:
<221> NAME/KEY: misc_feature
<222> LOCATION: (25)..(26)
<223> OTHER INFORMATION: Xaa can be any naturally or unnaturally
      occurring amino acid
<220> FEATURE:
<221> NAME/KEY: misc_feature
<222> LOCATION: (28)..(30)
<223> OTHER INFORMATION: Xaa can be any naturally or unnaturally
      occurring amino acid
<220> FEATURE:
<221> NAME/KEY: misc_feature
<222> LOCATION: (34)..(35)
<223> OTHER INFORMATION: Xaa can be any naturally or unnaturally
      occurring amino acid
<220> FEATURE:
<221> NAME/KEY: misc_feature
<222> LOCATION: (40)..(40)
<223> OTHER INFORMATION: Xaa can be any naturally or unnaturally
      occurring amino acid
<220> FEATURE:
<221> NAME/KEY: misc_feature
<222> LOCATION: (43)..(43)
<223> OTHER INFORMATION: Xaa can be any naturally or unnaturally
      occurring amino acid

<400> SEQUENCE: 42

Leu Pro Xaa Glu Leu Asn Arg Leu Leu Leu Ala Leu Arg Lys Leu Xaa
1               5                   10                  15

Asn Leu Val Thr Arg Gln Leu Tyr Xaa Xaa Glu Xaa Xaa Xaa Arg Tyr
            20                  25                  30

Tyr Xaa Xaa Leu Arg His Tyr Xaa Asn Leu Xaa Thr Arg Gln Arg Tyr
        35                  40                  45

<210> SEQ ID NO 43
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally or unnaturally
      occurring amino acid
<220> FEATURE:
<221> NAME/KEY: MISC_FEATURE
<222> LOCATION: (4)..(4)
<223> OTHER INFORMATION: Xaa = Asp or Glu
<220> FEATURE:
<221> NAME/KEY: MISC_FEATURE
<222> LOCATION: (5)..(5)
<223> OTHER INFORMATION: Xaa = Met or Leu
<220> FEATURE:
<221> NAME/KEY: misc_feature
<222> LOCATION: (6)..(6)
<223> OTHER INFORMATION: Xaa can be any naturally or unnaturally
      occurring amino acid
<220> FEATURE:
<221> NAME/KEY: MISC_FEATURE
<222> LOCATION: (10)..(11)
<223> OTHER INFORMATION: Xaa = Ser or Ala
<220> FEATURE:
<221> NAME/KEY: MISC_FEATURE
<222> LOCATION: (16)..(16)
<223> OTHER INFORMATION: Xaa = Ile or Leu
<220> FEATURE:
<221> NAME/KEY: MISC_FEATURE
<222> LOCATION: (19)..(19)
<223> OTHER INFORMATION: Xaa = Ile or Val
```

<400> SEQUENCE: 43

Xaa Xaa Glu Xaa Xaa Xaa Arg Tyr Tyr Xaa Xaa Leu Arg His Tyr Xaa
1               5                   10                  15

Asn Leu Xaa Thr Arg Gln Arg Tyr
            20

<210> SEQ ID NO 44
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = Met or Leu
<220> FEATURE:
<221> NAME/KEY: MISC_FEATURE
<222> LOCATION: (7)..(7)
<223> OTHER INFORMATION: Xaa = Lys or Arg
<220> FEATURE:
<221> NAME/KEY: misc_feature
<222> LOCATION: (9)..(10)
<223> OTHER INFORMATION: Xaa can be any naturally or unnaturally
      occurring amino acid
<220> FEATURE:
<221> NAME/KEY: MISC_FEATURE
<222> LOCATION: (11)..(11)
<223> OTHER INFORMATION: Xaa = Ser or Ala
<220> FEATURE:
<221> NAME/KEY: MISC_FEATURE
<222> LOCATION: (16)..(16)
<223> OTHER INFORMATION: Xaa = Ile or Leu

<400> SEQUENCE: 44

Ser Pro Glu Glu Xaa Asn Xaa Tyr Xaa Xaa Xaa Leu Arg His Tyr Xaa
1               5                   10                  15

Asn Leu Val Thr Arg Gln Arg Tyr
            20

<210> SEQ ID NO 45
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally or unnaturally
      occurring amino acid
<220> FEATURE:
<221> NAME/KEY: MISC_FEATURE
<222> LOCATION: (4)..(4)
<223> OTHER INFORMATION: Xaa = Asp or Glu
<220> FEATURE:
<221> NAME/KEY: MISC_FEATURE
<222> LOCATION: (5)..(5)
<223> OTHER INFORMATION: Xaa = Met or Leu
<220> FEATURE:
<221> NAME/KEY: misc_feature
<222> LOCATION: (6)..(6)
<223> OTHER INFORMATION: Xaa can be any naturally or unnaturally
      occurring amino acid
<220> FEATURE:
<221> NAME/KEY: MISC_FEATURE
<222> LOCATION: (7)..(7)
<223> OTHER INFORMATION: Xaa = Lys or Arg
<220> FEATURE:
<221> NAME/KEY: misc_feature
<222> LOCATION: (9)..(10)
<223> OTHER INFORMATION: Xaa can be any naturally or unnaturally

```
                      occurring amino acid
<220> FEATURE:
<221> NAME/KEY: MISC_FEATURE
<222> LOCATION: (11)..(11)
<223> OTHER INFORMATION: Xaa = Ser or Ala
<220> FEATURE:
<221> NAME/KEY: MISC_FEATURE
<222> LOCATION: (16)..(16)
<223> OTHER INFORMATION: Xaa = Ile or Leu
<220> FEATURE:
<221> NAME/KEY: MISC_FEATURE
<222> LOCATION: (19)..(19)
<223> OTHER INFORMATION: Xaa = Ile or Val

<400> SEQUENCE: 45

Xaa Xaa Glu Xaa Xaa Xaa Xaa Tyr Xaa Xaa Xaa Leu Arg His Tyr Xaa
1               5                   10                  15

Asn Leu Xaa Thr Arg Gln Arg Tyr
            20

<210> SEQ ID NO 46
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Xaa = Glu or Asp
<220> FEATURE:
<221> NAME/KEY: MISC_FEATURE
<222> LOCATION: (5)..(5)
<223> OTHER INFORMATION: Xaa = Met or Leu
<220> FEATURE:
<221> NAME/KEY: MISC_FEATURE
<222> LOCATION: (7)..(7)
<223> OTHER INFORMATION: Xaa = Lys or Arg
<220> FEATURE:
<221> NAME/KEY: MISC_FEATURE
<222> LOCATION: (11)..(11)
<223> OTHER INFORMATION: Xaa = Ser or Ala
<220> FEATURE:
<221> NAME/KEY: MISC_FEATURE
<222> LOCATION: (16)..(16)
<223> OTHER INFORMATION: Xaa = Arg, Ile, or Leu
<220> FEATURE:
<221> NAME/KEY: MISC_FEATURE
<222> LOCATION: (19)..(19)
<223> OTHER INFORMATION: Xaa = Ile or Val

<400> SEQUENCE: 46

Leu Pro Xaa Xaa Xaa Asn Xaa Leu Leu Leu Xaa Leu Arg Lys Leu Xaa
1               5                   10                  15

Asn Leu Xaa Thr Arg Gln Leu Tyr
            20

<210> SEQ ID NO 47
<211> LENGTH: 36
<212> TYPE: PRT
<213> ORGANISM: Artificial sequence
<220> FEATURE:
<223> OTHER INFORMATION: Synthetic peptide

<400> SEQUENCE: 47

Tyr Pro Ile Lys Pro Glu Ala Pro Gly Glu Asp Ala Ser Pro Glu Glu
1               5                   10                  15

Leu Asn Ala Tyr Tyr Ala Ser Leu Ala His Tyr Leu Asn Leu Val Thr
            20                  25                  30

Ala Gln Ala Tyr
```

```
                                  35
<210> SEQ ID NO 48
<211> LENGTH: 13
<212> TYPE: PRT
<213> ORGANISM: Artificial sequence
<220> FEATURE:
<223> OTHER INFORMATION: Synthetic peptide

<400> SEQUENCE: 48

Tyr Pro Ile Lys Pro Glu Ala Pro Gly Glu Asp Ala Ser
1               5                   10

<210> SEQ ID NO 49
<211> LENGTH: 23
<212> TYPE: PRT
<213> ORGANISM: Artificial sequence
<220> FEATURE:
<223> OTHER INFORMATION: Synthetic peptide

<400> SEQUENCE: 49

Pro Glu Glu Leu Asn Ala Tyr Tyr Ala Ser Leu Ala His Tyr Leu Asn
1               5                   10                  15

Leu Val Thr Ala Gln Ala Tyr
            20

<210> SEQ ID NO 50
<211> LENGTH: 24
<212> TYPE: PRT
<213> ORGANISM: Artificial sequence
<220> FEATURE:
<223> OTHER INFORMATION: Synthetic peptide

<400> SEQUENCE: 50

Ser Pro Asp Glu Leu Asn Arg Tyr Tyr Ala Ser Leu Arg His Tyr Leu
1               5                   10                  15

Asn Leu Val Thr Arg Gln Arg Tyr
            20
```

The invention claimed is:

1. A composition comprising a peptide consisting of SEQ ID NO: 34.

2. A pharmaceutical composition comprising the composition of claim 1 and a pharmaceutically acceptable carrier.

3. The pharmaceutical composition of claim 2, further comprising one or more additional therapeutic agents.

4. The pharmaceutical composition of claim 3, wherein the one or more additional therapeutic agents are selected from the group consisting of an antibiotic agent, an antiparasitic agent, an antiviral agent, an antimycotic agent, and commensal microbes.

5. The pharmaceutical composition of claim 2, formulated for oral or rectal administration.

6. A device comprising one or more surfaces coated with a composition of claim 1.

7. A method for reducing the growth of *Candida albicans* on or within a subject comprising administering a pharmaceutical composition of claim 2 to the subject.

8. The method of claim 7, wherein the growth of *Candida albicans* is reduced on the skin, in the gut, in the oral cavity, or in the vaginal cavity.

9. A method of treating a *Candida albicans* infection in or on a subject comprising administering a pharmaceutical composition of claim 2 to the subject.

10. A method of treating ulcerative colitis or Crohn's disease in a subject comprising administering a pharmaceutical composition of claim 2 to the subject.

11. The method of claim 10, wherein the Crohn's disease is ileal Crohn's Disease (iCD).

* * * * *